US006801859B1

(12) United States Patent
Friend et al.

(10) Patent No.: US 6,801,859 B1
(45) Date of Patent: Oct. 5, 2004

(54) METHODS OF CHARACTERIZING DRUG ACTIVITIES USING CONSENSUS PROFILES

(75) Inventors: Stephen H. Friend, Philadelphia, PA (US); Roland Stoughton, San Diego, CA (US); Yudong He, Kirkland, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 0 days.

(21) Appl. No.: 09/220,142

(22) Filed: Dec. 23, 1998

(51) Int. Cl.[7] .................. G01N 33/48; G01N 33/53; C12Q 1/68; G06G 7/48; C12P 21/06
(52) U.S. Cl. .................. 702/19; 435/6; 435/7.1; 435/7.2; 435/69.1; 703/11
(58) Field of Search ............... 435/6, 7.1, 7.2, 435/69.1; 702/19; 703/11; 436/501

(56) References Cited

U.S. PATENT DOCUMENTS

| | | | |
|---|---|---|---|
| 4,946,778 A | 8/1990 | Ladner et al. | 435/69.1 |
| 5,445,934 A | 8/1995 | Fodor et al. | 435/6 |
| 5,510,270 A | 4/1996 | Fodor et al. | 436/518 |
| 5,539,083 A | 7/1996 | Cook et al. | 536/333 |
| 5,556,752 A | 9/1996 | Lockhart et al. | 435/6 |
| 5,564,433 A | 10/1996 | Thornton | 128/731 |
| 5,569,588 A | 10/1996 | Ashby et al. | 435/6 |
| 5,578,832 A | 11/1996 | Trulson et al. | 296/48.1 |
| 5,645,988 A | 7/1997 | Vande Woude et al. | 435/6 |
| 5,686,114 A * | 11/1997 | Welsh | 424/601 |
| 5,744,305 A | 4/1998 | Fodor et al. | 435/6 |
| 5,769,074 A | 6/1998 | Barnhill et al. | 128/631 |
| 5,777,888 A | 7/1998 | Rine et al. | 364/196 |
| 5,800,992 A | 9/1998 | Fodor et al. | 435/6 |
| 5,811,231 A | 9/1998 | Farr et al. | 435/6 |
| 6,203,987 B1 * | 3/2001 | Friend et al. | 435/6 |

FOREIGN PATENT DOCUMENTS

| | | |
|---|---|---|
| EP | 0 534 858 A1 | 9/1992 |
| EP | 0 816 511 A1 | 1/1996 |
| WO | WO 88/09810 | 12/1988 |
| WO | WO 90/11364 | 10/1990 |
| WO | WO 94/17208 | 8/1994 |
| WO | WO 97/10365 | 3/1997 |
| WO | WO 97/27317 | 7/1997 |
| WO | WO 98/06874 | 2/1998 |
| WO | WO 98/38329 | 9/1998 |
| WO | WO 98/41531 | 9/1998 |
| WO | WO 99/58720 | 11/1999 |

OTHER PUBLICATIONS

Anderson et al., 1994, "Involvement of the protein tyrosine kinase p56lck in T cell signaling and thymocyte development", Adv Immunol 56:151–178.

(List continued on next page.)

Primary Examiner—Ardin H. Marschel
(74) Attorney, Agent, or Firm—Jones Day

(57) ABSTRACT

The present invention provides methods for enhanced detection of biological response profiles. In particular, the methods of this invention allow for the detection of biological response patterns, such as gene expression patterns, in response to different drug treatments. The methods of the invention also allow the determination of a "consensus profile" which describes a particular class or type of biological response. In certain embodiments the consensus profile may describe the biological response of a particular group or class of drugs. In other embodiments, the consensus profile may describe an "ideal" biological response such as one associated with a desired therapeutic effect. The methods of the present invention also allow for the comparison of different biological responses. Thus, the methods of the invention may be used, e.g., to identify and/or study new drugs.

13 Claims, 15 Drawing Sheets

OTHER PUBLICATIONS

Anderson, 1995, "Mutagenesis", Methods Cell. Biol. 48:31.

Arnone and Davidson, 1997, "The hardwiring of development: organization and function of genomic regulatory systems", Development 124:1851–1864.

Baudin et al., 1993, "A simple and efficient method for direct gene deletion in *Saccharomyces cerevisiae*," Nucl. Acids Res. 21:3329–3330.

Belshaw et al., 1996, "Controlling protein association and subcellular localization with a synthetic ligand that induces heterodimerization of proteins", Proc Natl Acad Sci USA 93:4604–4607.

Benoist and Chambon, 1981, "In vivo sequence requirements of the SV40 early promoter region", Nature 290:304–310.

Biocca and Cattaneo, 1995, "Intracellular immunization: antibody targeting to subcellular compartments", Trends Cell Biology 5:248–252.

Blanchard and Hood, 1996, "Sequence to array: probing the genome's secrets", Nat Biotechnol 14:1649.

Blanchard and Hood, 1996, "High–density oligonucleotide arrays", Biosensors and Bioelectronics 11:687–690.

Bradbury et al., 1995, "The cloning of Hybridoma V regions for their ectopic expression in intracellular and intercellular immunization" in *Antibody Engineering*, vol. 2, Borrebaeck (ed.) Oxford University Press, pp. 295–361.

Brinster et al., 1982, "Regulation of metallothionein—thymidine kinase fusion plasmids injected into mouse eggs", Nature 296:39–42.

Brown and Hartwell, 1998, "Genomics and human disease–variations on variation", Nature Genetics 18:91–93.

Brunel and Nadal, 1998, "Mutual information, Fisher information, and population coding", Neural Comput 10:1731–1757.

Bryant et al., (1998), "Gene Expression and Genetic Networks," Pacific Symposium on Biocomputing 3:3–5.

Burke and Warren, 1984, "Microinjection of mRNA coding for an anti–Golgi antibody inhibits intracellular transport of a viral membrane protein", Cell 36:847–858.

Burnette, 1981, "Western blotting": electropheretic transfer of proteins from sodium dodecyl sulphate–polyacrylamide gels to unmodifed nitrocellulose and radiographic detection with antibody and radioiodinated protein A, A. Anal. Biochem. 112:195–203.

Cannon–Albright and Skolnick, 1996, "The genetics of familial breast cancer", Seminars in Oncology 23:1–5.

Cardenas et al., 1994, "Yeast as model T cells", Perspectives in Drug Discovery and Design 2:103–126.

Carr et al., 1997, "Templates for Looking at Gene Expression Clustering," Statistical Computing & Statistical Graphics Newsletter pp. 20–29.

Cech, 1987, "The chemistry of self–splicing RNA and RNA enzymes", Science 236:1532–1539.

Chait, 1996, "Trawling for proteins in the post–genome era", Nature Biotechnol 14:1544.

Chee et al., 1996, "Accessing genetic information with high–density DNA arrays", Science 274:610–614.

Chirgwin et al., 1979, "Isolation of biologically active ribonucleic acid from sources enriched in ribonuclease", Biochemistry 18:5294–5299.

Chowdhury et al., 1997, "Lack of association of angiotensin II Type 1 receptor gene polymorphism with diabetic neuropathy in insulin–dependent Diabetes mellitus", Diabet. Med. 14:837–840.

Cole et al., 1985, "The EBV–Hybridoma technique and its application to human lung cancer" in *Monoclonal Antibodies and Cancer Therapy*, Alan R. Liss, Inc., pp. 77–96.

Cote et al., 1983, "Generation of human monoclonal antibodies reactive with cellular antigens", Proc Natl Acad Sci USA 80:2026–2030.

Cotten and Birnstiel, 1989, "Ribozyme mediated destruction of RNA in vivo", EMBO J 8:3861–3866.

Cunningham and Dunlop, 1996, "Molecular genetic basis of colorectal cancer susceptibility", British Journal of Surgery 83:321–329.

Cyert et al., 1992, "Regulator subunit (CNB1 gene product) of yeast Ca2+/calmodulin–dependent phosphoprotein phosphatases is required for adaptation to pheromone", Mol. Cell. Biol. 12:3460–3469.

D'haeseleer et al., (1998), "Mining the Gene Expression Matrix: Inferring Gene Relationships From Large Scale Gene Expression Data" Available Web Site: www.cs.unm.edu/~patrik/networks/IPCAT/ipcat.html Accessed on: Nov. 18, 1998 6:16 p.m.

DeRisi et al., 1997, "Exploring the metabolic and genetic control of gene expression on a genomic scale," Science 278:680–686.

DeRisi et al., 1996, "Use of a cDNA microarray to analyse gene expression patterns in human cancer", Nat Genet 14:457–460.

Deshaies et al., 1988, "A subfamily of stress proteins facilitates translocation of secretory and mitochondrial precursor polypeptides", Nature 332:800–805.

Dohmen et al., 1994, "Heat–inducible degron: a method for constructing temperature–sensitive mutants", Science 263:1273–1276.

Egholm et al., 1993, "PNA hybridizes to complementary olignucleotides obeying the Watson–Crick hydrogen–bonding rules", Nature 365:566–568.

Ferguson et al, 1996, "A fiber–optic DNA biosensor microarray for the analysis of gene expression", Nature Biotechnol 14:1681–1684.

Fodor et al., 1991, "Light–directed, spatially addressable parallele chemical synthesis", Science 251:767–773.

Frebourg and Friend, 1992, "Cancer risks for germline p53 mutations", J. Clin. Invest. 90:1637–1641.

Friend, 1994,"p53: A glimpse at the puppet behind the shadow play", Science 265:334–335.

Froehler et al., 1987, "Synthesis of DNA via deoxynucleoside H–phosphonate intermediates", Nucleic Acids Res 14:5399–5407.

Fuhrman et al., (1997), "Genetic Network Inference," *Proceedings of the International Conference on Complex Systems*, Nashua, NH, 21–26. Available Web Site: http://rsb.info.nih.gov/mol–physiol/ICCS/inference/ICCS.html Accessed on: Nov. 18, 1998 6:14 p.m.

Gari et al., 1997, "A set of vectors with a tetracycline–regulatable promoter system for modulated gene expression in *Saccharomyces cerevisiae*", Yeast 12:837–848.

Gautier et al., 1987, "Alpha–DNA. IV: Alpa–anomeric and beta–anomeric tetrathymidylates covalently linked to intercalating oxazolopyridocarbazole. Synthesis, physicochemical properties and poly (rA) binding", Nucleic Acids Res 15:6625–6641.

Gibson, 1996, "Antisense approaches to the gene therapy of cancer—'Recnac'", Cancer Metastasis Rev 15:287–299.

Goffeau et al., 1996, "Life with 6000 genes", Science 274:546, 563–567.

Good et al., 1997, "Expression of small, therapeutic RNAs in human cell nuclei", Gene Ther 4:45–54.

Gossen et al., 1995, "Transcriptional activation by tetracyclines in mammalian cells," Science 268:1766–1769.

Gossen and Bujard, 1995, "Tight control of gene expression in mammalian cells by tetracycline–responsive promoters", Proc Natl Acad Sci USA 89:5547–5551.

Grassi and Marini, 1996, "Ribozymes: structure, function and potential therapy for dominant genetic disorders", Annals Medicine 28: 499–510.

Griffiths et al, 1994, "Isolation of high affinity human antibodies directly from large synthetic repertoires", EMBO J 13:3245–3260.

Guo et al., 1994, "Direct fluorescence analysis of genetic polymorphisms by hybridization with oligonucleotide arrays on glass supports," Nucl. Acids Res. 22:5456–5465.

Haluska and Hodi, 1998, "Molecular genetics of familial cutaneous melanoma", Journal of Clinical Oncology 16:670–682.

Hanke et al., 1996, "Discovery of a novel, potent, and Src family–selective tyrosine kinase inhibitor. Study of Lck– and FynT–dependent T cell activation", J Biol Chem 271:695–701.

Hartwell et al., 1997, "Integrating genetic approaches into the discovery of anticancer drugs," Science 278:1064–1068.

Haseloff and Gerlach, 1988, "Simple RNA enzymes with new and highly specific endoribonuclease activities", Nature 334:585–591.

Hayden et al., 1997, "Antibody engineering", Curr Opin Immunol 9:201–212.

Herskowitz, 1987, "Functional inactivation of genes by dominant negative mutations", Nature 329:219–222.

Hertz and Stormo, 1995, "Identification of consensus patterns in unaligned DNA and protein sequences: a large deviation statistical basis for penalizing gaps", in *Proceedings of 3rd International Conference on Bioinformatics and Genome Research*, Lim and Cantor, eds., World Scientific Publishing Co., Ltd., Singapore, pp. 201–216.

Hoffmann et al., 1997, "A novel tetracycline–dependent expression vector with low basal expression and potent regulatory properties in various mammalian cell lines.", Nucleic Acids Res 25:1078–1079.

Hoffmann JS, et al., "Fork–like DNA templates support bypass replication of lesions that block DNA synthesis on single–stranded templates", Proc Natl Acad Sci U S A. Nov. 26, 1996;93(24):13766–13769.

Huse et al., 1989, "Generation of a large combinatorial library of the immunoglobulin repertoire in phage lambda", Science 246:1275–1281.

Inoue et al., 1987, "Sequence–dependent hydrolysis of RNA using modified oligonucleotide splints and RNase H", FEBS Lett 215:327–330.

Inoue et al., 1987, "Synthesis and hybridization studies on two complementary nona(2'–O–methyl)ribonucleotides", Nucleic Acids Res 15:6131–6148.

Izumi, R. et al., 1992, "Alpha–fetoprotein production by hepatocellular carcinoma is prognostic of poor patient survival", Journal of Surgical Oncology 49:151–155.

Johnston and Davis, 1984, "Sequences that regulate the divergent GAL1–GAL10 promoter in *Saccharomyces cerevisiae*", Mol Cell Biol 8:1440–1448.

Kohler and Milstein, 1975, "Continuous cultures of fused cells secreting antibody of predefined specificity", Nature 256:495–497.

Koizumi et al., 1988, "Construction of a series of several self–cleaving RNA duplexes using synthetic 21–mers", FEBS Lett 228:228–230.

Koizumi et al., 1988, "Cleavage of specific sites of RNA by designed ribozymes", FEBS Lett 239:285–288.

Kozbor and Roder, 1983, "The production of monoclonal antibodies from human lymphocytes", Immunol Today 4:72.

Kricka, 1992, *Nonisotopic DNA Probe Techniques*, Academic Press, San Diego, CA.

Krol et al., 1988, "Modulation of eukaryotic gene expression by complementary RNA or DNA sequences", BioTechniques 6: 958–976.

Krug and Berger, 1987, "First–strand cDNA synthesis primed with oligo(dT)", Methods Enzymol 152:316–325.

Lander, 1996, "The new genomics: global views of biology", Science 274:536–539.

Lemaitre et al., "Specific antiviral activity of a poly(L–lysine)–conjugated oligodeoxyribonucleotide sequence complementary to vesicular stomatitis virus N protein mRNA initiation site", Proc Natl Acad Sci USA 84:648–652.

Lennon and Lehrach, 1991, "Hybridization analyses of arrayed cDNA libraries" *Trends Genet.* 7:314–317.

Letsinger et al., 1989, "Cholesteryl–conjugated oligonucleotides: synthesis, properties, and activity as inhibitors of replication of human immunodeficiency virus in cell culture", Proc Natl Acad Sci USA 86:6553–6556.

Li et al., 1992, "Recommendations on predictive testing for germ–line p53 mutations among cancer–prone individuals", J. Natl. Cancer Inst. 84:1156–1160.

Lockhart et al., 1996, "Expression monitoring by hybridization to high–density oligonucleotide arrays", Nat Biotechnol 14:1675–1680.

Madhani and Fink, 1998, "The riddle of MAP kinase signaling specificity", Trends Genet 14:151–155.

Marks et al., 1992, "Molecular evolution of proteins on filamentous phage. Mimicking the strategy of the immune system", J Biol Chem 267:16007–16010.

Marnellos et al., (1998) "A Gene Network Approach to Modeling Early Neurogenesis in Drosophila," *Pacific Symposium on Biocumputing* 3:30–41. Available Web Site: http://www–smi.stanford.edu/projects/helix/psb98/.

Marton et al., 1998, "Drug target validation and identification of secondary drug target effects using DNA microarrays", Nature Medicine 4:1293–1301.

Mascorro–Gallardo et al., 1996, "Construction of a CUP1 promoter–based vector to modulate gene expression in *Saccharomyces cerevisiae*", Gene 172:169–170.

Maskos and Southern, 1992, "Oligonucleotide hybridizations on glass supports: a novel linker for oligonucleotide synthesis and hybridization properties of oligonucleotides synthesised in situ", Nucleic Acids Res 20:1679–1684.

Matheos et al., 1997, "Tcn1p/Crz1p, a calcineurin–dependent transcription factor that differentially regulates gene expression in *Saccharomyces cerevisiae*," Genes & Dev. 11:3445–3458.

McAdams and Shapiro, 1995, "Circuit simulation of genetic networks," Science 269:650–656.

McBride and Caruthers, 1983, "An investigation of several deoxynucleoside phosphoramidites useful for synthesizing deoxyoligonucleotides", Tetrahedron Lett 24:245–248.

McCormack et al., 1997, "Direct analysis and identification of proteins in mixtures by LC/MS/MS and database searching at the low–femtomole level", Anal Chem 69:767–776.

Michaels et al., (1998), "Cluster Analysis and Data Visualization of Large–Scale Gene Expression Data," *Pacific Symposium on Biocomputing* 3:42–53. Available Web Site: http://www–smi.stanford.edu/projects/helix/psb98/ Assessed on: Nov. 24, 1998 3:48 p.m.

Mikulecy, 1990, "Modeling intestinal absorption and other nutrition–related processes using PSPICE and STELLA," J. Ped. Gastroenterol. Nutr. 11:7–20.

Morgan and Roth, 1988, "Analysis of intracellular protein function by antibody injection", Immunol Today 9:84–88.

Morrison et al., 1984, "Chimeric human antibody molecules: mouse antigen–binding domains with human constant region domains", Proc Natl Acad Sci USA 81:6851–6855.

Mounts and Liebman, 1997, "Qualitative modeling of normal blood coagulation and its pathological states using stochastic activity networks," Int. J. Biol. Macromolecules 20:265–281.

Mumberg et al., 1994, "Regulatable promoters of *Saccharomyces cerevisiae*: comparison of transcriptional activity and their use for heterologous expression", Nucleic Acids Res 22:5767–5768.

Neuberger et al., 1984, "Recombinant antibodies possessing novel effector functions", Nature 312:604–608.

Neumann et al., 1996, "Monogenetic hypertension and pheochromocytoma", American Journal of Kidney Diseases 28:329–333.

Nguyen et al., 1995, "Differential gene expression in the murine thymus assayed by quantitative hybridization of arrayed cDNA clones", Genomics 29:207–216.

No et al., 1996, "Ecdysone–inducible gene expression in mammalian cells and transgenic mice", Proc Natl Acad Sci USA 93:3346–3351.

Nocka et al., 1990, "Molecular bases of dominant negative and loss of function mutations at the murine c–kit/white spotting locus: W37, Wv, W41 and W", EMBO J 9:1805–1813.

Paulus et al., 1996, "Self–contained, tetracycline–regulated retroviral vector system for gene delivery to mammalian cells", J Virol 70:62–67.

Pease et al., 1994, "Light–generated oligonucleotide arrays for rapid DNA sequence analysis", Proc Natl Acad Sci USA 91:5022–5026.

Perlmutter and Alberola–lla, 1996, "The use of dominant–negative mutations to elucidate signal transduction pathways in lymphocytes", Curr Opin Immunol 8:285–290.

Pettitt et al., 1996, "cdh–3, a gene encoding a member of the cadherin superfamily, functions epithelial cell morphogenesis in *Caenorhabditis elegans*", Development 122:4149–4157.

Pietu et al., 1996, "Novel gene transcripts preferentially expressed in human muscles revealed by quantitative hybridization of a high density cDNA array," Genome Res. 6:492.

Polyak et al., 1997, "A model for p53–induced apoptosis," Nature 389:300–306.

Prashar and Weissman, 1996, "Analysis of differential gene expression by display of 3'end restriction fragments of cDNAs", Proc Natl Acad Sci USA 93:659–663.

Press et al., 1996, *Numerical Recipes in C*, 2nd Ed. Cambridge Univ. Press, Ch. 10.

Ramirez–Solis et al., 1993, "Gene targeting in embryonic stem cells", Methods Enzymol 225:855–878.

Reinitz and Sharp, 1995, "Mechanism of eve stripe formation," Mech. Dev. 49:133–158.

Ross, 1996, "Pharmacodynamics: mechanism of drug action and the relationship between drug concentration and effect," in *The Pharmacological Basis of Therapeutics*, Gilman et al,. ed., McGraw Hill, New York.

Rothstein, 1991, "Targeting, disruption, replacement, and allele rescue: integrative DNA transformation in yeast", Methods Enzymol. 194:281.

Sagliocco et al., 1996, "Identification of proteins of the yeast protein map using genetically manipulated strains and peptide–mass fingerprinting", Yeast 12:1519–1533.

Sarin et al., 1988, "Inhibition of acquired immunodeficiency syndrome virus by oligodeoxynucleoside methylphosphonates", Proc Natl Acad Sci USA 85:7448–7451.

Sarver et al., 1990, "Ribozymes as potential anti–HIV–1 therapeutic agents", Science 247:1222–1225.

Schena et al., 1995, "Quantitative monitoring of gene expression patterns with a complementary DNA microarray", Science 270:467–470.

Schena, 1996, "Genome analysis with gene expression microarrays," BioEssays 18:427.

Schena et al., 1996, "Parallel human genome analysis: microarray–based expression monitoring of 1000 genes", Proc Natl Acad Sci USA 93:10614–10619.

Shalon et al., 1996, "A DNA microarray system for analyzing complex DNA samples using two–color fluorescent probe hybridization", Genome Res 6:639–645.

Shevchenko et al., 1996, "Linking genome and proteome by mass spectrometry: large–scale identification of yeast proteins from two dimensional gels", Proc Natl Acad Sci USA 93:14440–14445.

Shiue, 1997, "Identification of candidate genes for drug discovery by differential display," Drug Dev. Res. 41:142–159.

Shoemaker et al., 1996, "Quantitative phenotypic analysis of yeast deletion mutants using a highly parallel molecular bar–coding strategy," Nature Genetics 14:450–456.

Sikorski and Hieter, 1989, "A system of shuttle vectors and yeast host strains designed for efficient manipulation of DNA in *Saccharomyces cerevisiae*", Genetics 122:19–27.

Somogyi, R., (1997), "Level–by–Level Interference From Large–Scale Gene Expression Data," *Functional Genomics* pp. 1–16. Available Web Site: http://rsb.info.nih.gov/mol–physiol/FG/FGpresentation.html.

Southern, 1996, "DNA chips: analysing sequence by hybridization to oligonucleotides on a large scale", Trends Genet. 12:110–115.

Spencer, 1996, "Creating conditional mutations in mammals", Trends Genet 12:181–187.

Spradling et al., 1995, "Gene disruptions using P transposable elements: an integral component of the Drosophila genome project", Proc Natl Acad Sci USA 92:10824–10830.

Stathopoulos and Cyert, 1997, "Calcineurin acts through the CRZ1/TCN1–encoded transcription factor to regulate gene expression in yeast," Genes & Dev. 11:3432–3444.

Stein et al., 1988, "Physicochemical properties of phosphorothioate oligodeoxynucleotides", Nucleic Acids Res 16:3209–3221.

Stern et al., 1996, "Evidence for a major gene for type II Diabetes and linkage analyses with selected candidate genes in Mexican–Americans", diabetes 45:563–568.

Stormo and Hartzell, 1989, "Identifying protein–binding sites from unaligned DNA fragments", Proc Natl Acad Sci USA 86:1183–1187.

Straus and Weiss, "Genetic evidence for the involvement of the lck tyrosine kinase in signal transduction through the T cell antigen receptor", Cell 70:585–593.

Takeda et al., 1985, "Construction of chimaeric processed imunoglobulin genes containing mouse variable and human constant region sequences", Nature 314:452–454.

Thomas et al., 1995, "Dynamical behavior of biological regulatory networks – I. Biological role of feedback loops and practical use of the concept of the loop–characteristic state," Bull. Math. Biol. 57:247–276.

Thomas and Capecchi, 1987, "Site–directed mutagenesis by gene targeting in mouse embryo–derived stem cells", Cell 51:503–512.

Thorsness et al, 1989, "Positive and negative transcriptional control by heme of genes encoding 3–hydroxy–3–methylglutaryl coenzyme A reductase in S.cerevisiae", Mol. Cell. Biol. 9:5702–5712.

Tijessen, 1993, Laboratory Techniques in Biochemistry and Molecular Biology. Hybridization With Nucleic Acid Probes, Elsevier Science Publishers B.V.

Tomlinson et al., 1997, "Molecular genetics of colon cancer", Cancer and Metastasis Reviews 16:67–79.

van der Krol et al., 1988, Modulation of eukaryotic gene expression by complementary RNA or DNA sequences. Biotechniques 6:958–976.

Velculescu, 1995, "Serial anlaysis of gene expression", Science 270:484–487.

Wach et al., 1994, "New heterologous modules for classical or PCR–based gene disruptions in Saccharomyces cerevisiae," Yeast, 10:1793–808.

Wagner, 1996, "Genetic redundancy caused by gene duplications and its evolution in networks of transcriptional regulators", Biol Cybern 74:557–567.

Wagner, 1981, "Nucleotide sequence of the thymidine kinase gene of herpes simplex virus type 1", Proc Natl Acad Sci USA 78:1441–1445.

Ward, 1963, "Hierarchical grouping to optimize an objective function", J Am Stat Assn 58:236–244.

Weinstein et al., 1997, "An information–intensive approach to the molecular pharmacology of cancer," Science 275:343–349.

Weisgraber and Mahley, 1996, "Human apolipoprotein E: the Alzheimer's disease connection", FASEB J. 10:1485–1494.

Wen et al., (1998), "Large–Scale Temporal Gene Expression Mapping of Central Nervous System Development," Proc. Natl. Acad. Sci. USA 95:334–339.

Yamamoto et al., 1980, "Identificatikon of a functional promoter in the long terminal repeat of Rous sarcoma virus", Cell 22:787–797.

Yatscoff, R.W. et al., 1996, "Pharmacodynamic monitoring of immunosuppressive drugs", Transplantation Proceedings 28:3013–3015.

Yuh et al., 1998, "Genomic cis–regulatory logic: experimental and computational analysis of a sea urchin gene", Science 279:1896–1902.

Zhao et al., 1995, "High–density cDNA filter analysis: a novel approach for large–scale, quantitative analysis of gene expression," Gene 156:207–213.

Zon, 1988, "Oligonucleotide analogues as potential chemotherapeutic agents", Pharm Res 5:539–549.

Garrels et al., 1990, Electrophoresis 11:1114–1130.

Oden, 1992, American Journal of Physical Anthropology 89:257–264.

Macario et al., 1991, Gene 108:133–137.

Reich, 1987, Analytica Chimica Acta 201: 171–188.

Esposito et al., 1985, "Orthopoxvirus DNA: A Comparison of Restriction Profiles and Maps", Virology 143:230–251.

Eisen et al., 1998, "Cluster analysis and display of genome–wide expression patterns" Proc. Natl. Acad. Sci. USA 95:14863–14868.

Hoffmaster et al., Infection and Immunity, vol. 65, No. 8, pp. 3091–3099.*

* cited by examiner

By Experiment. To FIG.2D

METHODS OF CHARACTERIZING DRUG ACTIVITIES USING CONSENSUS PROFILES

1. FIELD OF THE INVENTION

The field of this invention relates to methods of identifying common elements or patterns in biological profiles, such as common elements in gene expression profiles, in response to different drug treatments. The invention also relates to the application of these methods to identify ideal drug profiles as well as undesired drug profiles. Further, the invention also relates to the application of these methods to compare profiles from existing drugs to these ideals.

2. BACKGROUND OF THE INVENTION

Within the past decade, several technologies have made it possible to monitor the expression level of a large number of genetic transcripts (see, e.g., Schena et al., 1995, *Science* 270:467–470; Lockhart et al., 1996, *Nature Biotechnology* 14:1675–1680; Blanchard et al., 1996, *Nature Biotechnology* 14:1649; Ashby et al., U.S. Pat. No. 5,569,588, issued Oct. 29, 1996) and proteins (see, e.g., McCormack et al., 1997, *Analytical Chemistry* 69:767–776; Chait-BT, 1996, *Nature Biotechnology* 14:1544) within a cell at any one time. In organisms for which the complete genome is known, it is possible to analyze the transcripts of all genes within the cell. With other organisms such as human, for which there is an increasing knowledge of the genome, it is possible to simultaneously monitor large numbers of the genes within the cell.

Applications of this technology have included, for example, identification of genes which are up regulated or down regulated in various physiological states, particularly diseased states. Additional uses for transcript arrays have included the analyses of members of signaling pathways, and the identification of targets for various drugs. See, e.g., Friend and Hartwell; U.S. Provisional Patent Application Serial No. 60/039,134, filed Feb. 28, 1997; Stoughton, U.S. patent application Ser. No. 09/099,722, filed Jun. 19, 1998; Stoughton and Friend, U.S. patent application Ser. No. 09/074, 983, filed May 8, 1998; Friend and Hartwell, U.S. Provisional Application Serial No. 60/056,109, filed Aug. 20, 1997; Friend and Hartwell, U.S. application Ser. No. 09/031,216, filed Feb. 26, 1998; Friend and Stoughton, U.S. Provisional Application Serial No. 60/084,742 (filed May 8, 1998). 60/090,004 (filed June 19, 1998), and 60/090,046 (filed Jun. 19, 1998). Such applications are based upon the knowledge that abundances and/or activity levels of cellular constituents (e.g., mRNA species, proteins, and other molecular species within a cell) change in response to perturbations in a cell's biological state, including drug treatment or changes in a protein's activity. Thus, a measurement of such cellular constituents, referred to herein as a "biological profile," or "profile," contains a wealth of information about the action of the perturbing agent.

The ability to measure and compare such biological profiles has the potential to be of great human and commercial benefit. For example, it would be of great benefit if an "ideal" or "consensus" response profile could be identified across a large set of cellular constituents, for example all or substantially all of the genetic transcripts of a cell or organism, which characterizes a desired drug activity (e.g., a desired clinical effect). Likewise, it would also be of great benefit, e.g., during the process of drug discovery and design, to provide and compare response profiles of known or existing drugs to such a consensus profile, e.g., to identify promising drug candidates with a particular, desired, therapeutic effect, or to develop theories of why particular individual compounds have clinically superior toxicity profiles. Indeed the basic concept of generating and comparing response profiles to known profiles for the purpose of predicting drug effectiveness and toxicity has been proposed (see, in particular, Fodor, U.S. Pat. No. 5,800,992; Rine and Ashby, 1998, U.S. Pat. No. 5,777,888)

However, the biological profile of any real cell or organism is of tremendously high complexity. Any one perturbing agent may cause a small or large number of cellular constituents to change their abundances and/or activities. Thus, to completely or even mostly characterize the biological response to a particular perturbation it is generally necessary to measure independently the responses of all, or at least most, of the cellular constituents in a cell. Yet, the number of cellular constituents, e.g., for a mammalian cell, is typically on the order of $10^5$. Further, current techniques for quantifying changes in cellular constituents suffer from high rates of measurement errors, including false detections, failures to detect, or inaccurate quantitative determinations. Thus, in practice such analyses of biological profiles is too cumbersome and fraught with technical problems to be practical.

Accordingly, there is a need for methods of analyzing biological profile data which overcome the above limitations in the prior art, and, in particular, which reduce error rates and simplify the structure of changes in the profile data. In particular, there is a need for methods of analyzing biological profile data to derive a simplified "consensus profile," e.g., for a drug, drug family, or group of related compounds, which characterizes a desired (i.e., ideal) biological effect. Further, there is a need for methods to compare such consensus profiles to the biological profiles of individual drugs or drug candidates.

Discussion or citation of a reference herein shall not be construed as an admission that such reference is prior art to the present invention.

3. SUMMARY OF THE INVENTION

The present invention provides methods for determining a "consensus" profile for a biological response, such as the response of an organism to a group or family of drugs and/or drug candidates. The consensus profile obtained by the methods of this invention represents an ideal, desired activity profile across some standard measurement set such as the cellular constituents of a cell or model organism, or of an organism destined for treatment, e.g., by drug therapy. As such, the consensus profiles of this invention indicate those elements or patterns in a biological profile which the individual compounds have in common. Preferably, such elements or patterns are associated with a particular biological effect—most preferably a particular, desired, therapeutic effect, or "ideal" effect. Accordingly, the present invention also provides methods for obtaining a response profile for a particular compound, such as for a particular drug or drug candidate, and for comparing the response profile of the particular compound to the consensus profile to determine the extent to which the particular compound exhibits a particular, i.e., "ideal," effect as opposed to "non-ideal" or toxic effects.

Such methods are useful, e.g., in the process of drug discovery or design, for identifying compounds which best meet or satisfy a desired activity profile, as well as for identifying compounds which fall short of a desired activity profile. The methods of the present invention are also useful for analyzing further chemical modifications to lead compounds, or for developing theories of why certain individual compounds have superior toxicity profiles. Finally, because the biological response to a particular compound or compounds will frequently vary between individual organisms, the methods of the present invention are also useful during treatment of an individual, e.g., in a clinical setting, to determine the best compound or combination of compounds to produce a desired therapeutic effect.

The invention is based, at least in part, on the discovery that for any finite set of conditions, including, for example, treatments with different concentrations of related compounds, individual cellular constituents will not vary independently from one another. Rather, sets of cellular constituents will tend to change together, or "co-vary," under a given set of conditions. Accordingly, the structure of biological profiles can be greatly reduced, without losing accuracy or completeness, by grouping cellular constituents into sets, referred to herein as co-varying sets, which co-vary under some set of conditions. Preferably, the set of conditions includes the conditions or perturbations under investigations (i.e., graded exposure to the individual drugs or compounds being studied). In fact, because grouping constituents into co-varying sets actually averages experimental errors, error rates are reduced, thereby enabling better detection, classification, and comparison of changes in cell profiles.

The methods of the present invention include: (i) obtaining or providing response profiles for the biological response (or responses) of interest; (ii) defining sets of co-regulated cellular constituents (i.e., genesets) in the response profiles; and (iii) identifying common response motifs among the defined sets of co-regulated cellular constituents which are associated with particular biological responses such as drug effectiveness or toxicity. The common response motifs thereby identified comprise the consensus profiles of the invention. In preferred embodiments, the methods of the invention further include the step (iv) of "projecting" the original response profiles onto the genesets identified in step (ii) above. Simplified, reduced-dimension response profiles are thereby produced which are more simply and robustly related to biological properties such as drug effectiveness and toxicity.

In various embodiments, the response profiles may be obtained, e.g., by measuring gene expression, protein abundances, protein activities, or a combination of such measurements. In various embodiments, the methods of the invention further comprise a step of selecting only those cellular constituents that show significant response in some fraction of the response profiles. In various embodiments, the methods of the invention may further comprise the implementation of a clustering algorithm or other pattern recognition procedure to group the cellular constituents into co-regulated sets. In various embodiments, the methods of the invention may further comprise the implementation of a clustering algorithm or other pattern recognition procedure to group the response profiles according to similarity. In various preferred embodiments, the grouped cellular constituents and response profiles are displayed, e.g., in a false color plot, to facilitate the identification of major sets of cellular constituents and common response motifs in steps (ii) and (iii) above.

In more detail, the present invention provides, in a first embodiment, methods for determining a consensus profile for a particular biological response. Such methods involve identifying common response motifs among sets of co-varying cellular constituents in a plurality of perturbation response profiles, wherein the common response motifs are associated with the particular biological response. The biological response is typically associated with a particular biological effect, such as the effect of a particular class or type of drug, a therapeutic effect, or a toxic effect. In various aspects of this first embodiment, the sets of co-varying cellular constituents comprise sets of cellular constituents that are co-regulated, and/or cellular constituents which are co-varying in the plurality of perturbation response profiles. Such co-varying cellular constituent sets are identified, e.g., by cluster analysis of cellular constituents in the plurality of perturbation response profiles. In still other aspects of this first embodiment, the perturbation response profiles are re-ordered into sets associated with similar biological effect, e.g., by cluster analysis. In other aspects of the first embodiment, the co-varying cellular constituents comprise basis cellular constituent sets, and the perturbation response profiles are projected onto the basis cellular constituent sets to provide projected response profiles.

The consensus profile determined in the first embodiment of this invention is, in particular, the intersection of the sets of co-varying cellular constituents activated or de-activated in the common response motifs. The intersection may be identified, e.g., by visual inspection of the plurality of response profiles, by thresholding the projected response profiles, or arithematically.

In a second embodiment, the present invention also provides methods for comparing a biological response profile to a consensus profile. The methods comprise (a) converting the biological response profile into a projected response profile according to a definition of basis cellular constituent sets, and (b) determining the value of a similarity metric between the projected response profile and the consensus profile. Preferably, the basis cellular constituent sets comprise cellular constituent sets which co-vary. The similarity metric may be, in certain aspects of the second embodiment, the generalized cosine angle between the projected response profile and the consensus profile.

In a third embodiment, the present invention provides methods for analyzing a biological sample. In particular, the methods of this embodiment comprise (a) grouping cellular constituents from the biological sample into sets of cellular constituents that co-vary in biological profiles obtained from the biological sample, and (b) grouping the biological profiles obtained from the biological sample into sets of biological profiles that effect similar cellular constituents. In a preferred aspect of this embodiment, one or more cellular constituents and/or one or more response profiles associated with a particular biological effect are identified from such sets of cellular constituents and/or biological profiles. For example, in some aspects the cellular constituents comprise genes or gene transcripts so that one or more genes associated with a particular biological effect are identified. The genes identified by the methods of this embodiment may be known or previously unknown genes.

Finally, the methods of this invention are preferably executed on automated systems, e.g., computer system, capable of performing the above methods. Accordingly, this invention also provides, in a third embodiment, computer systems comprising a computer-usable medium having computer readable program code embodied theron for effecting the methods of this invention.

4. BRIEF DESCRIPTION OF THE FIGURES

FIG. 1 illustrates a flow chart of an embodiment of the methods of the invention.

FIGS. 2A–D illustrates an exemplary application of the methods of the invention; FIG. 2A is a gray scale display of 185 genetic transcripts of *S. Cerevisiae* (horizontal axis) measured in 34 different perturbation experiments (vertical axis); FIG. 2B shows the co-regulation tree obtained by clustering the genetic transcripts of FIG. 2A using the hclust algorithm; FIG. 2C is an illustration of the same experimental data in which the transcripts have been re-ordered according to the genesets defined from FIG. 2B; FIG. 2D is another illustration of the experimental data in which the experimental index (vertical axis) has also been reordered according to similarity of the response profiles.

FIG. 3 is another illustration of the data in FIG. 2 in which the genetic transcripts (horizontal axis) and experiments (veritcal axis) are ordered according to similarity; individual genesets are identified above the gray scale image, while the biological pathways and/or responses with which each geneset is associated are indicated below the image; the label on the vertical axis summarizes each experiment.

5. DETAILED DESCRIPTION

Figure 1:
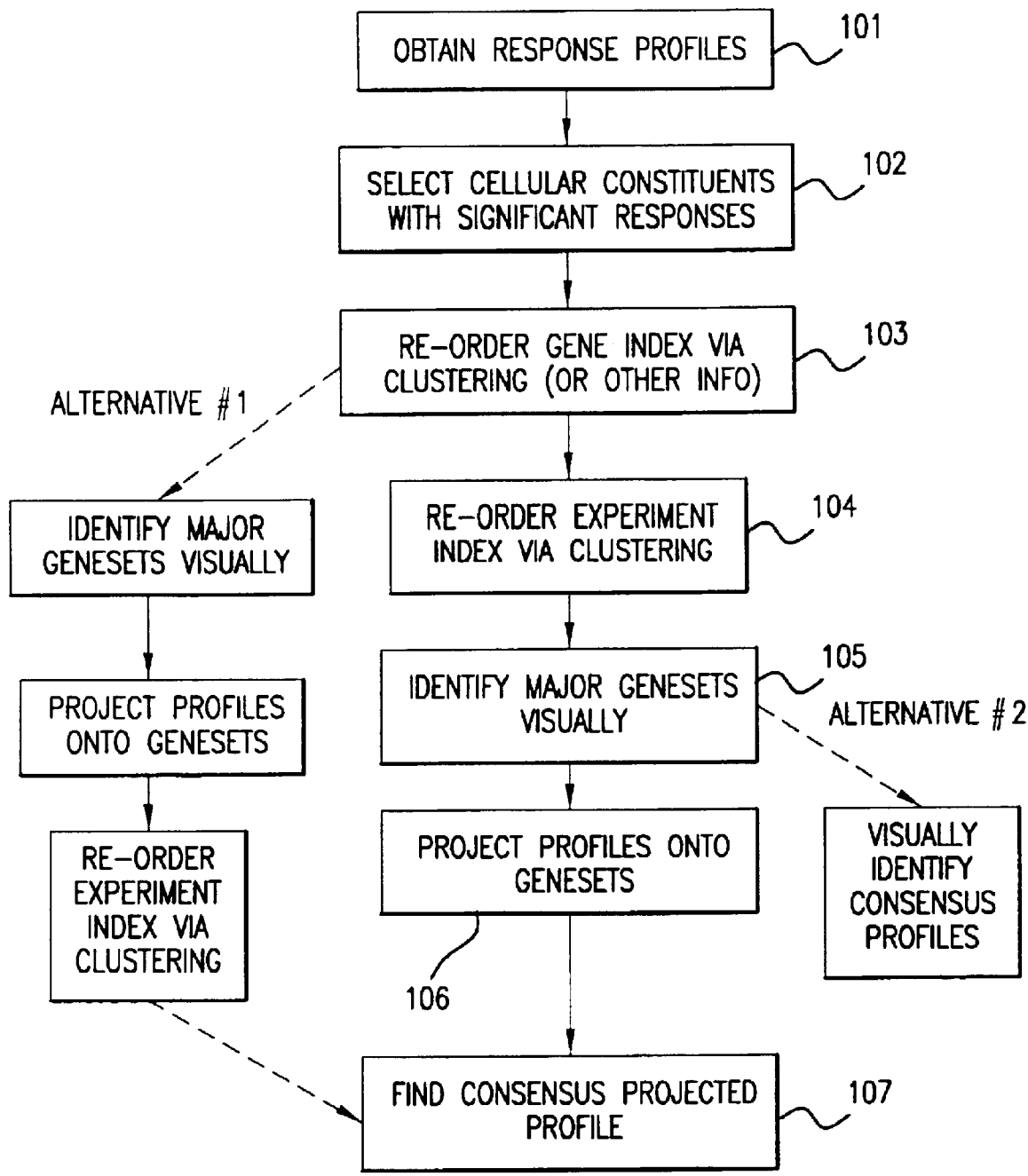

This section presents a detailed description of the invention and its applications. In particular, Section 5.1 describes certain preliminary concepts useful in the further description of this invention. Section 5.2 generally describes the methods of the invention, while Section 5.3 describes preferred analytic embodiments of the methods of the invention. Finally, Section 5.4 describes methods of measuring cellular constituents and Section 5.5. describes various targeted methods of perturbing the biological state of a cell or organism.

The description is by way of several exemplary illustrations, in increasing detail and specificity, of the general methods of the invention. The examples are non-limiting, and related variants that will be apparent to one skilled in the art are intended to be encompassed by the appended claims. Following these examples are descriptions of embodiments of the data gathering steps that accompany the general methods.

5.1. Introduction

The present invention relates to methods and systems for identifying (i.e., characterizing) drug activity using consensus profiles. In particular, the methods and systems of the invention enable one to identify "consensus profiles" comprising common elements in response profiles to different drug treatments which correspond to particular biological effects of the drugs such as drug effectiveness or toxicity. The methods and systems of the invention also enable one to compare different response profiles, e.g., from exposure to different but related drugs, to such consensus profiles, in order to evaluate the biological properties of a particular drug in a cell or organism, such as drug effectiveness or toxicity. The methods of the invention involve analyzing measurements of changes in the biological state of a cell (i.e., "response profiles"), most preferably in response to graded levels of exposure to one or more drugs, (a) to define major sets of co-regulated cellular constituents in the response profiles, and (b) to identify common response motifs among the co-regulated cellular constituents associated with particular biological responses, such as drug effectiveness or toxicity.

This section first presents certain preliminary concepts, including those of drug action, the biological state of a cell, and co-varying sets of cellular constituents. Next, a schematic and non-limiting overview of the methods of this invention is presented. The following sections present the methods of the invention in greater detail.

Although, for simplicity, this disclosure often makes reference to single cells (e.g., "RNA is isolated from a cell exposed to a particular concentration of a drug"), it will be understood by those of skill in the art that more often any particular step of the invention will be carried out using a plurality of genetically similar cells, e.g., from a cultured cell line. Such similar cells are referred to herein as a "cell type." Such cells are either from naturally single celled organisms, or are derived from multi-cellular higher organisms.

5.1.1. Drug Action

According to the current invention, drugs are any compounds of any degree of complexity that perturb a biological system, whether by known or unknown mechanisms and whether or not they are used therapeutically. Drugs thus include: typical small molecules of research or therapeutic interest; naturally-occurring factors, such as endocrine, Paracrine, or autocrine factors or factors interacting with cell receptors of all types; intracellular factors, such as elements of intracellular signaling pathways; factors isolated from other natural sources; pesticides; herbicides; insecticides; and so forth. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their effects by interacting with a protein. Drugs that increase rates or stimulate activities or levels of a protein are called herein "activating drugs", while drugs that decrease rates or inhibit activities or levels of a protein are called herein "inhibiting drugs". As will be clear to the skilled artisan, while the invention is described herein in terms of determining a consensus profile for different drugs, and using them to identify the activity of a "drug," it is equally applicable to determining a consensus profile for different preparations of a particular drug, i.e., compositions which comprise or contain a particular drug but also contain different additional ingredients.

The methods of determining consensus profiles of a group of drugs, and using such profiles to identify drug activity in a cell can be used, e.g., to determine therapeutic efficacy (e.g., if a drug response profile from an individual undergoing a particular drug therapy is identical or similar to a consensus profile representing "ideal" drug effects), to compare different drugs or drug candidates for relative drug effectiveness and relative toxicity, to evaluate new drugs, such as chemical modifications to existing drugs or drug candidates, or to test theories about certain drug interactions (e.g., theories about chemical or structural features of drugs which produce superior toxicity profiles). In all of these aspects, different drugs may include, e.g., different compositions or preparations of the same pharmacophore.

In addition to drugs, this invention is equally applicable to those changes in the aspects of the physical environment that perturb a biological system in targeted manners. Such environmental changes can include moderate changes of temperature (e.g., a temperature elevation of 10° C.) or exposure to moderate doses of radiation. Other environmental aspects include the nutritional environment, such as the presence or absence of particular sugars, amino acids, and so forth.

5.1.2. Biological State

The biological effects of a drug (or a physical environmental change) are measured in the instant invention by observations of changes in the biological state of a cell. The cell may be of any type, e.g., prokaryotic, eukaryotic, mammalian, plant, or animal. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurements relevant to the characterization of drug action. In various embodiments, this invention includes making such measurements and/or observations on different collections of cellular constituents. These different collections of cellular constituents are also called herein aspects of the biological state of the cell. As used herein, the term "cellular constituents" is not intended to refer to known subcellular organelles, such as mitochondria, lysozomes, etc.

One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured to characterize the action of a drug of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and optionally catalytically active nucleic acid species) in the cell under a given set of conditions. As is known to those of skill in the art, the translational state is often representative of the activity state.

The present invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Drug exposure will typically affect many constituents of whatever aspects of the biological state of a cell are being measured and/or observed in a particular embodiment of the invention. For example, as a result of regulatory, homeostatic, and compensatory networks and systems known to be present in cells, even an "ideal drug," i.e., a drug that directly affects only a single constituent in a cell and without direct effects on any other constituent, will have complicated and often unpredictable indirect effects. A drug that specifically and completely inhibits activity of a single hypothetical protein, protein P, is considered here as an example. Although the drug itself will directly change the activity of only protein P, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. Therefore, the direct effect of the drug on its target, protein P, is hidden in the large number of indirect effects downstream from protein P. Such downstream effects of protein P are called herein the biological pathway originating at protein P.

Accordingly, a "non-ideal" drug that directly affects more than one primary molecular target, may have still more complicated downstream effects. In one aspect, according to the present invention, the analysis of these effects provides considerable information about the drug including, for example, identification of biological pathways effected by the drug and which explain its action and side effects of toxicities in the cell. In a related aspect, the present invention provides methods for carrying out this analysis.

Measurement of the transcriptional state of a cell is preferred in this invention, not only because it is relatively easy to measure but also because, although a drug may act through a post-transcriptional mechanism (such as inhibition of the activity of a protein or change in its rate of degradation), the administration of a drug to a cell almost always results in a measurable change, through direct or indirect effects, in the transcriptional state. A reason that drug exposure changes the transcriptional state of a cell is because the previously mentioned feed back systems, or networks, which react in a compensatory manner to infections, genetic modifications, environmental changes (including drug administration), and so forth do so primarily by altering patterns of gene expression or transcription. As a result of internal compensations, many perturbations to a biological system, although having only a muted effect on the external behavior of the system, can nevertheless profoundly influence the internal response of individual elements, e.g., gene expression, in the cell.

5.1.3. Co-varying Sets

In general, for any finite set of conditions, such as treatments with different concentrations of related compounds, cellular constituents will not all vary independently. Rather, there will be simplifying subsets of cellular constituents which typically change together, e.g., by increasing or decreasing their abundances and/or activities, under some set of conditions which preferably include the conditions or perturbations of interest to a user of the present invention (e.g., treatment with different concentrations of related compounds). Such cellular constituents are said to "co-vary," and are therefore referred to herein as co-varying cellular constituent sets, or "co-varying sets."

Further, the abundances and/or activities of individual cellular constituents are not all regulated independently. Rather, individual cellular constituents from a cell will typically share one or more regulatory elements with other cellular constituents from the same cell. For example, and not by way of limitation, in embodiments where the cellular constituents comprise genetic transcripts, the rates of transcription are generally regulated by regulator sequence patterns, i.e., transcription factor binding sites. Typically, several genes within a cell may share one or more transcription factor binding sites. Such cellular constituents are therefore said to be "co-regulated," and comprise co-regulated cellular constituent sets or "co-regulated sets."

As is apparent to one of skill in the art, those sets of cellular constituents which are co-regulated will, at least under certain conditions, co-vary. For example, and not by way of limitation, genes tend to increase or decrease their rates of transcription together when they possess similar transcription factor binding sites. Such a mechanism accounts for the coordinated responses of genes to particular signalling inputs. For example, see Madhani and Fink, 1998, *Transactions in Genetics* 14:151–155; and Arnone and Davidson, 1997, *Development* 124:1851–1864. For instance, individual genes which synthesize different components of a necessary protein or cellular structure are generally co-regulated and tend to co-vary. Also, duplicated genes (see, e.g., Wagner, 1996, *Biol. Cybern.* 74:557–567) are co-regulated and tend to co-vary to the extent that genetic mutations have not led to functional divergence in their regulatory regions. Further, because genetic regulatory sequences are modular (see, e.g., Yuh et al., 1998, *Science* 279:1896–1902), the more regulatory "modules" two genes have in common, the greater the variety of conditions under which they will co-vary in their transcription rates. Physical separation between modules along the chromosome is also an important determinant since co-activators are often involved. Accordingly, and as is also apparent to one of skill in the art, the terms co-regulated set and co-varying set may be used interchangeably in the description of this invention.

In particularly preferred embodiments of the present invention, the cellular constituents in a biological profile comprise genetic transcripts such as mRNA abundances, or abundances of cDNA molecules produced from mRNA transcripts. In such embodiments, the co-varying sets comprise genes which co-vary and are generally co-regulated to some extent. Such co-varying sets are referred to herein as "genesets." Thus, in particularly preferred embodiments of the present invention, the co-varying cellular constituent sets are genesets.

Co-varying sets of cellular constituents are useful in that they form a meaningful and simplified basis for describing biological profiles. In particular, co-varying sets may be used to describe profile differences within a finite set of conditions, such as exposure to different concentrations of related compounds. Further, because descriptions of the biological state in terms of co-varying sets tends to cancel experimental errors from measurements of individual cellular constituents, co-varying sets allow increases and detection sensitivity in classification accuracy.

5.2. Overview of the Methods of the Invention

The methods and systems of the present invention enable a user to identify consensus response profiles or consensus profiles which characterize a particular biological effect. In particular, the consensus profiles of the invention may describe, e.g., the desired activity profile of a particular drug or of a particular class or family of drugs. As such, the consensus profiles of the invention may represent an ideal therapeutic effect or drug efficacy. Likewise, the consensus profiles of the invention may describe and/or represent an undesired activity profile of a particular class or family of drugs, such as an activity profile associated with drug toxicity.

FIG. 1 illustrates a general overview of the methods of the present invention. The methods of the invention analyze response profiles which are obtained or provided (101) from measurements of aspects of the biological state of a cell in response to a particular set or sets of perturbations, such as drug exposure, targeted mutations, or targeted changes in protein activity or expression (see, e.g., Section 5.5 below). Specifically, aspects of the biological state of a cell, for example, the transcriptional state, the translational state, or the activity state, are measured (as described in Section 5.4 below) in response to a plurality perturbations. Preferably, the measurements are differential measurements of the change in cellular constituents in response to the drug at certain concentrations and times of treatment. The collection of these measurements, optionally graphically presented, are called herein the "perturbation response" or "drug response" or "response profile." Preferably, a plurality of drug response profiles are obtained or provided for a plurality of different drugs, specifically for those drugs for which a consensus profile is desired (e.g., for each member of a particular class or family of drugs, or for perturbations in the expression and or activity of primary targets of those drugs). However, response profiles may also be obtained or provided for other drugs or conditions, such as genetic mutations, which are associated with a particular biological effect or effects of interest. In most embodiments, at least five, preferably more than ten, more preferably more than 50, and more preferably more than 100 different perturbations are employed.

In most preferred embodiments of the invention, the cells used for cluster analysis are of the same type and from the same species as the species of interest. For example, human kidney cells are preferably tested to identify consensus profiles to evaluate drugs or therapies that are used to treat disorders involving human kidney cells. However, in some preferred embodiments, the biological samples are not of the same type or are not from the same species as the species of interest. For example, in certain preferred embodiments, yeast cells may be used to define consensus profiles that are useful, e.g., in comparing or evaluating drugs or drug candidates used or intended for human therapies.

In some embodiments, cellular constituents are measured as continuous variables. For example, transcriptional rates are typically measured as numbers of molecules synthesized per unit time. Transcriptional rates may also be measured as percentages of a control rate. In still other embodiments, cellular constituents may be measured as categorical variables. For example, transcriptional rates may be measured as either "on" or "off," where "on" indicates a transcriptional rate that is above or equal to a particular, user-determined threshold, and the value "off" indicates a transcriptional rate that is below that threshold.

In preferred embodiments, the response profiles analyzed by the methods of the invention are optionally screened, before the analysis, to select only those cellular constituents that have a significant response in some fraction of the profiles (102). In particular, although the profiles may cover up to ~$10^5$ cellular constituents, in most drug treatments a large part or even a majority of these constituents will not change significantly in response to treatment, or the changes may be small and dominated by experimental error. In most embodiments, it will be unhelpful and cumbersome to use these constituents in the analysis methods of the invention. Thus they are preferably deleted from all profiles.

In some embodiments, only cellular constituents that have a response greater than or equal to two standard errors in more than N profiles are selected for subsequent analysis, where N may be one or more and is preferably selected by the user. Preferably, N will tend to be larger for larger sets of response profiles. For example, in one preferred embodiment N may be approximately equal to the square root of the number of response profiles being analyzed.

Drug response profiles having been thus provided and, optionally, screened to select cellular constituents with significant responses, the cellular constituents and the individual drug response profiles are each grouped according to their similarities (103 and 104). In particular, the cellular constituents being analyzed according to the methods of the present invention are grouped or re-ordered into co-varying sets (103). Methods for grouping and/or re-ordering cellular constituents into co-varying sets are described in detail in Section 5.3.2 below. Preferably, the cellular constituents are grouped or re-ordered by means of a pattern recognition procedure or algorithm, most preferably by means of a clustering procedure or algorithm. Likewise, a similar operation is performed to group the response profiles according to similarity (104). The steps of grouping or re-ordering the cellular constituents and grouping or re-ordering response profiles may be performed in any order; i.e., the cellular constituents may be grouped in co-varying sets first followed by grouping the response profiles, or the response profiles may be grouped first followed by grouping the cellular constituents. The two orders are equivalent providing, however, that the re-ordering of cellular constituents is applied uniformly to all response profiles.

Preferably, the re-ordered cellular constituents and/or the re-ordered response profiles are visually displayed, e.g., in a false color plot indicating increases and/or decreases in activity levels and/or abundances of each cellular constituent. For example, in preferred embodiments wherein the cellular constituents comprise genetic transcripts, such a visual display would preferably comprise a false color plot of up-regulation and down-regulation of individual transcripts.

Figure 2A:
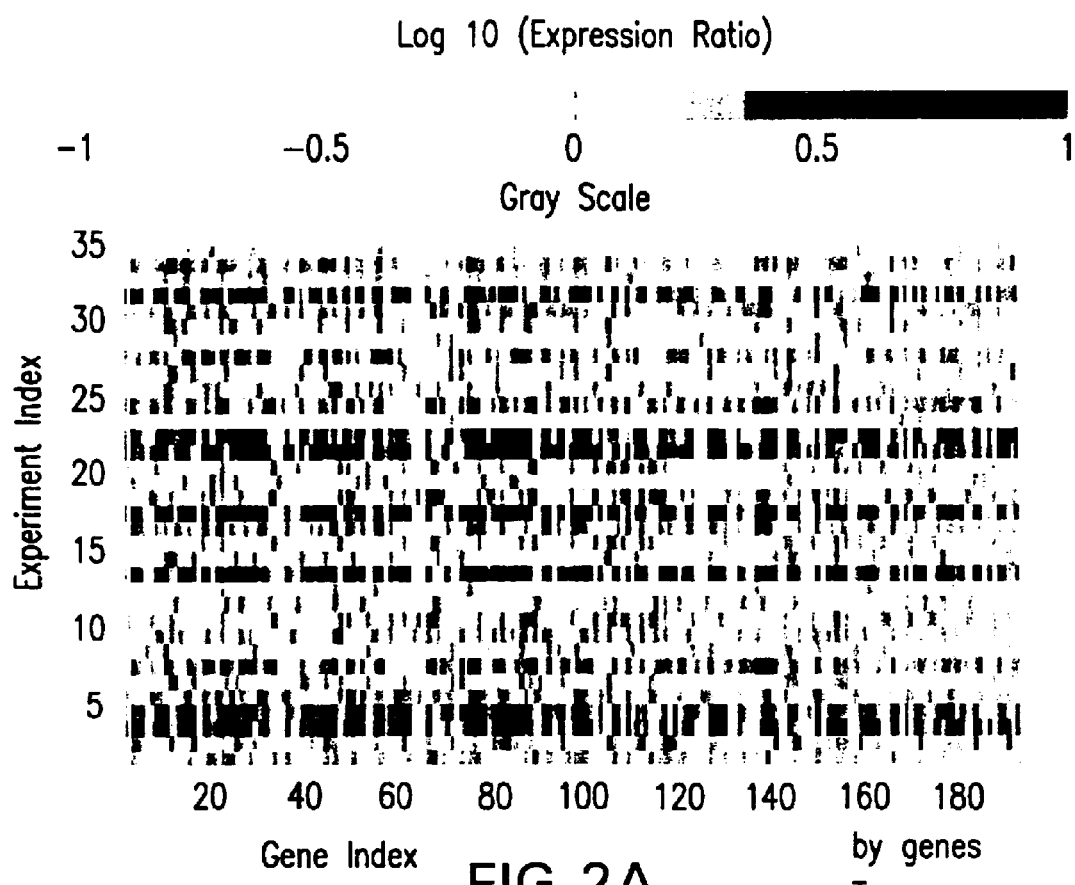
Figure 2B:
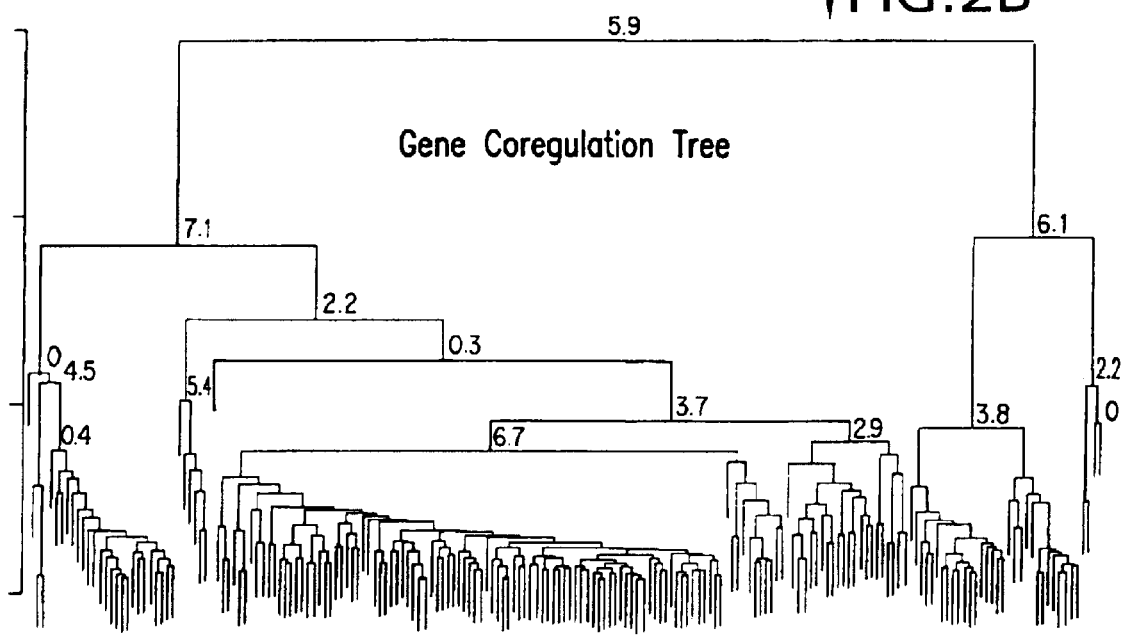
Figure 2C:
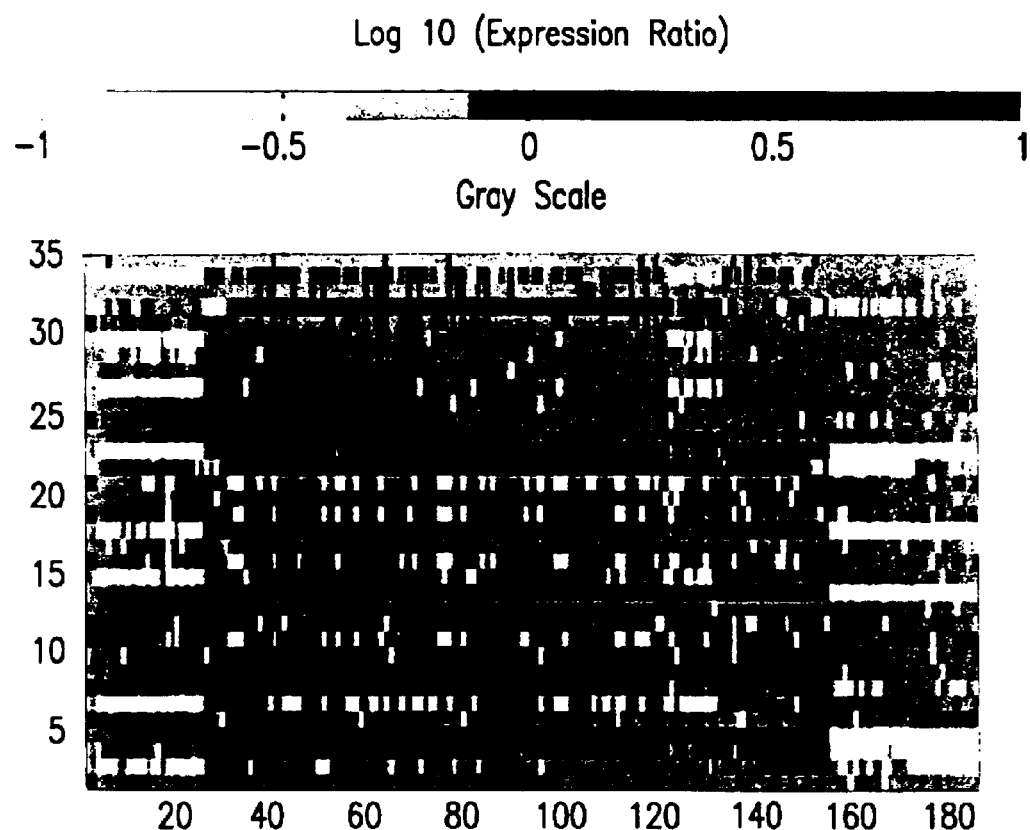
Figure 2D:
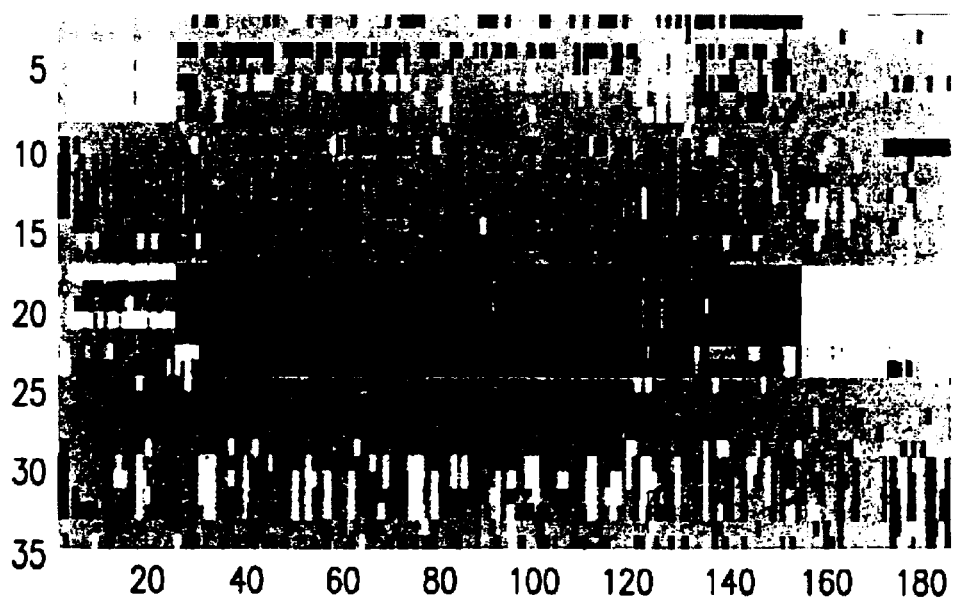
Figure 3:
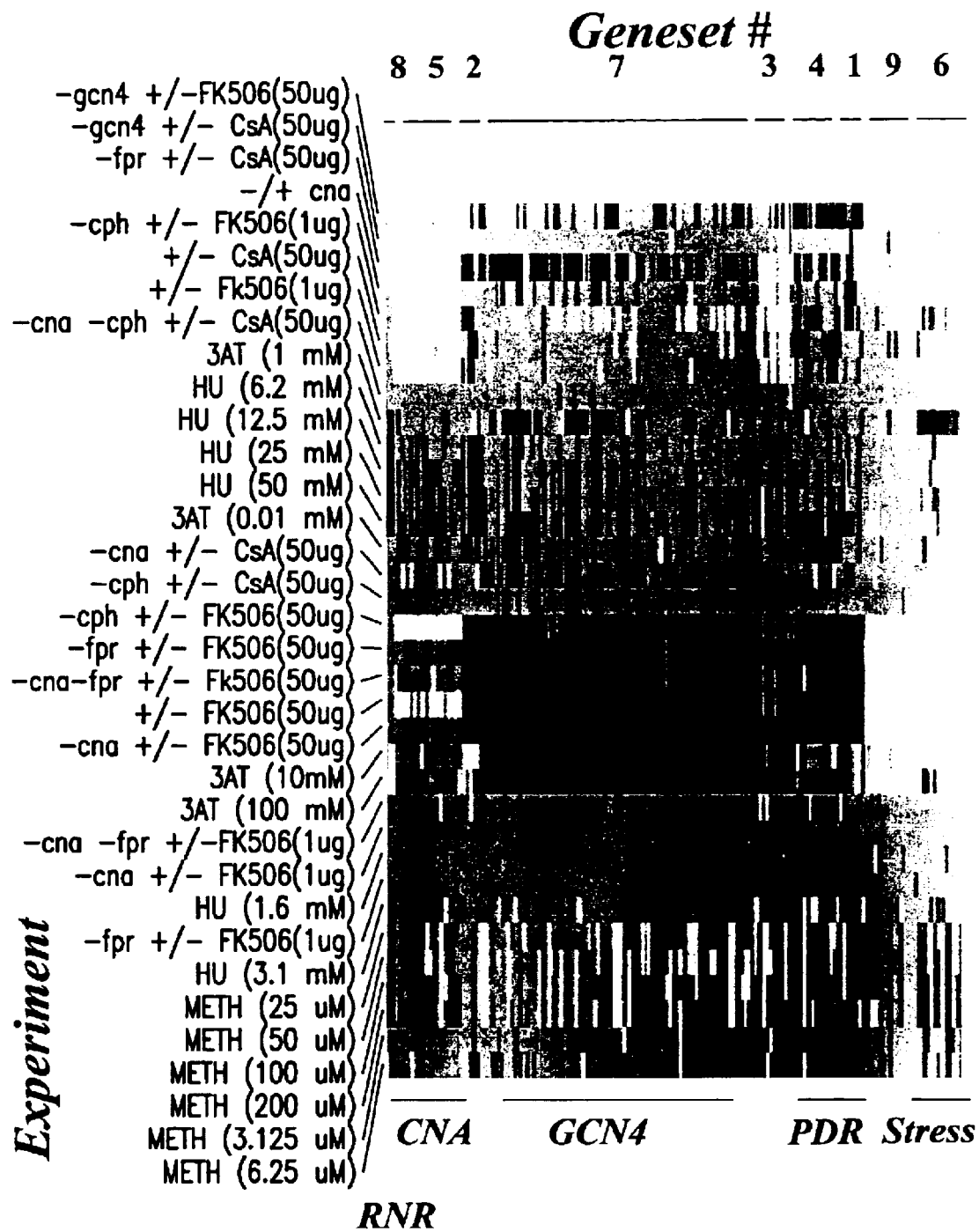

An exemplary display is illustrated in FIGS. 2 and 3. Specifically, FIG. 2A shows a gray scale display of a plurality of genetic transcripts (horizontal axis) measured in a plurality of experiments (vertical axis), i.e., response profiles, wherein cells are exposed to different perturbations (e.g., graded exposure to different drugs). Thus, each row in FIG. 2A indicates the response of genetic transcripts to a particular perturbation (e.g., exposure to a particular drug). Black denotes up regulation of a transcript (+1), whereas white denotes down regulation (−1), and the middle gray scale (0) denotes no change in expression. FIG. 2B illustrates the grouping of genetic transcripts into genesets by means of a coregulation tree (described in Section 5.3.3 below), and FIG. 2C illustrates the visual display of the re-ordered transcripts. FIG. 2D illustrates the visual display of both re-ordered transcripts and re-ordered profiles.

FIG. 3 gives a detailed view of FIG. 2D with labels showing (a) the individual experiments, (b) the individual genesets (top label), and (c) the biological responses or pathways associated with each geneset (bottom label). Specifically, the experiments comprise 34 experiments including different drug treatments and genetic mutations related to the yeast *S. Cerevisiae* biochemical pathway homologous to immunosuppression in humans (described in Marton et al., *Nature Medicine*, in press), as well as experiments with concentrations of the non-immunosuppressant drugs hydroxyurea, Methotrexate, and 3-Aminotriazole. The genesets illustrated in FIGS. 2 and 3 comprise a total of 185 genes. Specifically, ~6,000 yeast genes were measured in each of the 34 experiments. However, only those genes which have responses of two standard errors or more in four or more experiments are displayed or used for subsequent analysis.

Visual displays, such as the visual display shown in FIG. 3, can then be used to facilitate the identification (i.e., definition) of major co-varying sets (105) which infer common response motifs associated with a particular biological response of interest, such as drug effectiveness or toxicity. However, such groupings and/or identification of major co-varying sets and common response motifs may also be done by means of quantitative, preferably objective, methods which are described in Section 5.3.5, below. For example, groups or sets may be defined as statistically significant by means of Monte Carlo generation of empirical probability distributions for measures of compactness.

Finally, once such groups (e.g., major co-varying sets) are defined, they may be used as a basis (106) to describe simplified biological profiles related to known biological properties of interest, such as drug effectiveness or drug toxicity. In preferred embodiments, the major co-varying sets provide a reduced mathematical basis set which may be used to describe biological profiles within the finite set of experimental conditions from which the major co-varying sets have been determined. Specifically, the original profiles are "projected" onto the major co-varying sets, to obtain simplified, reduced-dimension biological profiles. The process of projection is described, in detail, in Section 5.3.4, below. The reduced-dimension biological profiles thus obtained are more simply and robustly related to known properties such as drug effectiveness and toxicity. For example, the group or groups of major co-varying sets in which the average response is significant for each of the compounds or drugs known to be biologically or therapeutically effective may be associated with the desired, primary effects of the drug. The projected profile corresponding to these effects would therefore comprise a consensus profile for that drug (107).

The sections below describe exemplary, non-limiting, embodiments of the methods and systems of the present invention. Specifically, Section 5.3 describes exemplary analytical embodiments of the methods and systems of the invention. The analytical methods of the invention include, methods for grouping and selecting co-varying cellular constituents (Section 5.3.2) and response profiles (Section 5.3.3) according to their similarity, methods for projecting biological response profiles onto basis co-varying cellular constituents (Section 5.3.4), and methods for obtaining consensus profiles from such projected biological response profiles (Section 5.3.5). The analytical embodiments of the invention also include systems, e.g., computer systems, which are capable of implementing the analytical methods of the invention. Exemplary systems are described below in Section 5.3.6.

Finally, Sections 5.4 and 5.5 describe methods by which the biological response profiles used in the analytical methods of the invention may be obtained or provided. Specifically, Section 5.4 describes methods for measuring pluralities of cellular constituents in a cell which are used to determine and/or describe the cell's biological state. Methods and systems for measuring drug response data (Section 5.4.1), and the transcriptional state of cells (Section 5.4.2) are described, as well as methods and systems for measuring other aspects of a cell's biological state (Section 5.4.3), including the translational and activity states. Section 5.5 describes methods for targeted perturbation of the biological state of a cell or organism.

Description of these embodiments is by way of non-limiting examples, and related variants of these embodiments will be apparent to one skilled in the art. Such variants are intended to be encompassed as part of the instant invention. In particular, for simplicity this disclosure often makes reference to gene expression profiles, transcriptional rates, transcript levels, etc. However, it will be understood by those skilled in the art that the methods of the invention are useful for the analysis of any biological response profile. Specifically, one skilled in the art will recognize that the methods of the present invention are equally applicable to biological response profiles which comprise measurements of other cellular constituents such as, but not limited to, measurements of protein abundances or protein activity levels.

Further, because this disclosure often makes reference to embodiments wherein the cellular constituents analyzed by the methods of the invention are gene expression profiles, the disclosure also makes reference to embodiments wherein the co-varying sets of cellular constituents are genesets (i.e., co-varying sets of gene expression profiles). However, one skilled in the art will also recognize that the methods of the present invention are equally applicable to other types of co-varying cellular constituent sets, including co-varying sets comprised, e.g., of the cellular constituents identified in the above paragraph.

5.3. Analytical Embodiments

Analytical embodiments of the methods and systems of the present invention include, first, embodiments for representing measured biological profiles, especially measured response profiles of a biological sample to a perturbation, in terms of "vectors" of cellular constituents. The second aspect of the analytical embodiments of the invention comprises embodiments for grouping cellular constituents from one or more measured response profiles into co-varying sets. Similarly, another aspect of the analytical embodiments comprises embodiments for grouping measured response profiles according to their similarity. A fourth aspect of the analytical embodiments of the invention include methods for projecting response profiles onto co-varying sets of cellular constituents so that the response profiles are described in terms of a reduced basis set of co-varying cellular constituents. Finally, the analytical embodiments of the methods of this invention also include methods for obtaining consensus profiles from the co-varying sets, and for comparing projected profiles to such consensus profiles, as well as to one another. Exemplary embodiments of these analytical methods are described in Sections 5.3.1 through 5.3.5 below.

The embodiments of the analytical methods of the invention are preferably done using automated systems, e.g., computer systems, which perform one or more of the method embodiments of the invention automatically given user input comprising, e.g., response profile data from a biological sample or samples in response to particular perturbations. Such systems are also described below in Section 5.3.6.

5.3.1. Representation of Biological Responses

Figure 4:
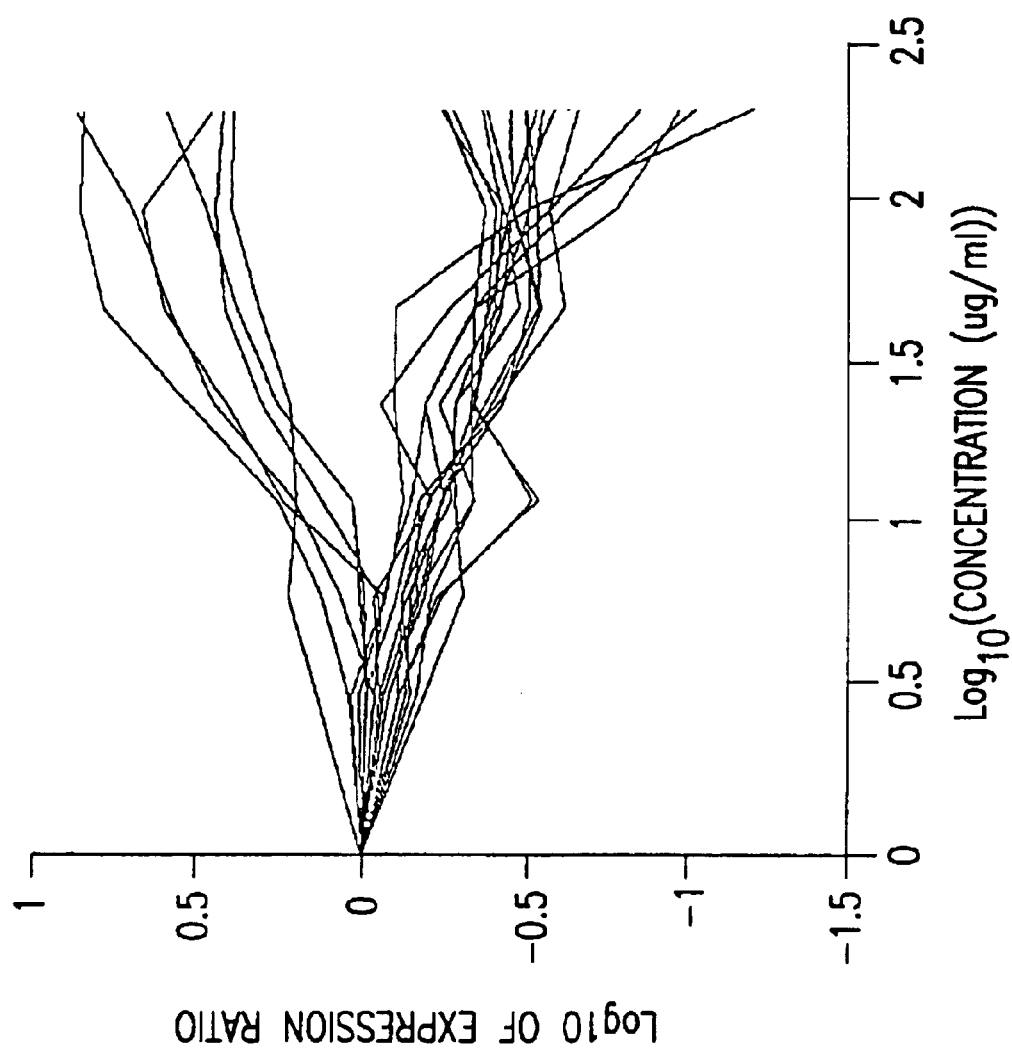
FIG. 4 is a plot of mRNA response to Methotrexate in *S. Cerevisiae*.

The response of a biological sample (e.g., a cell or cell culture) to a perturbation, such as the application of a drug, can be measured by observing changes in the biological state of the sample. In one exemplary embodiment, response data are obtained by a method involving treating a biological sample (e.g., cells) with different concentrations of a drug to produce a characteristic drug response profile involving a well-defined set of cellular constituents, and wherein the response amplitudes of all the cellular constituents increase together with the increasing drug concentration. For example, FIG. 4 illustrates exemplary drug response profile data obtained by titrating cells of S. Cerevisiae with graded concentrations of the drug Methotrexate, and measuring mRNA transcript levels. Only those mRNA transcripts with responses larger than a factor of two at two or more drug concentrations are shown.

Figure 5:
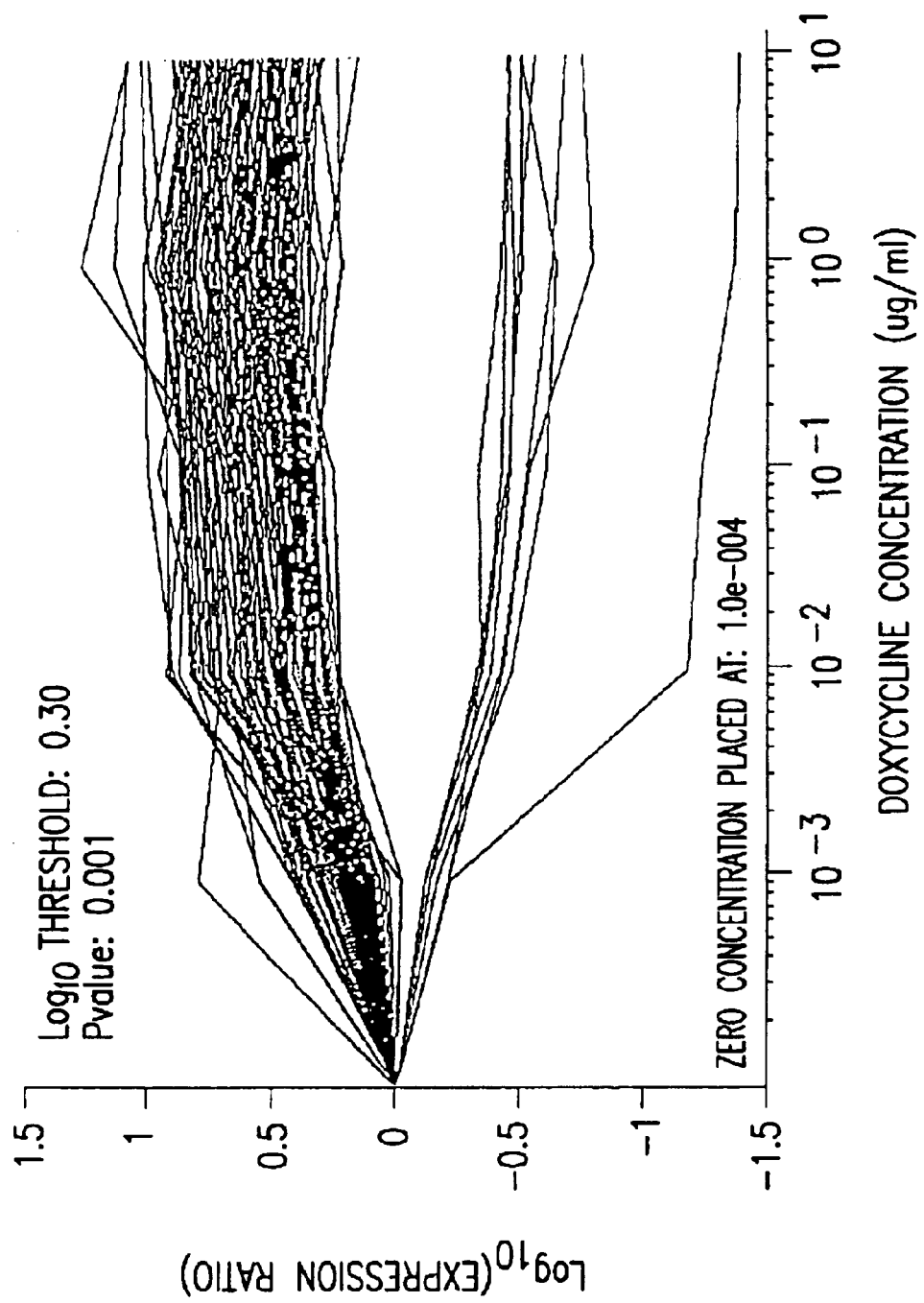
FIG. 5 is a plot of mRNA responses to varying levels of activity of the ERG11 gene, where this activity was controlled with a tet-promoter under control of doxycycline.

Other exemplary perturbations include variation of growth media and/or conditions such as temperature and density, genetic mutations, and use of controllable gene promoters, as well as other methods described in Section 5.5 below. For example, FIG. 5 illustrates exemplary biological response profile data obtained by varying activity levels of the S. Cerevisiae gene ERG11 using a tet-promoter under control of doxycycline (see Section 5.5.4 below).

Such response profile data comprise a collection of measured changes of a plurality k of cellular constituents. Such response profiles can be described for quantitative analysis in terms of the vector v. In particular, the response profile of a biological sample to the perturbation n is defined herein as the vector $v^{(n)}$:

$$v^{(n)} = [v_1^{(n)}, \ldots, v_i^{(n)}, \ldots, v_k^{(n)}] \qquad (1)$$

where $v_i^{(n)}$ is the amplitude of the response of cellular constituent i under the perturbation n. In some embodiments, $v_i^{(n)}$ may be simply the difference between the abundances and/or activity levels of cellular constituent i before and after the perturbation n is applied to the biological sample, or the difference in abundances and/or activity levels of cellular constituent i between a biological sample that is subject to the perturbation n and a sample that is not subject to the perturbation n. In other embodiments, $v_i^{(n)}$ is the ratio (or the logarithm of the ratio) of the abundances and/or activity levels of cellular constituent i before and after the perturbation n is applied to the biological sample, or the ratio (or the logarithm of the ratio) of abundance and/or activity level of cellular constituent i in a sample subject to the perturbation n to a sample that is not subject to the perturbation n.

In preferred embodiments, $v_i^{(n)}$ is set equal to zero for all cellular constituents i whose response is below a threshold amplitude or confidence level which may be determined, e.g., from knowledge of the measurement error behavior. For example, in some embodiments, only cellular constituents that have a response greater than or equal to two standard errors in more than N profiles may be selected for subsequent analysis, where the number of profiles N is preferably selected by a user of the invention.

For those cellular constituents whose responses are above the threshold amplitude, $v_i^{(n)}$ may be equal to the measured value. For example, in embodiments wherein the perturbation n comprises graded levels of exposure to a perturbation such as graded levels of exposure to a drug n, $v_i^{(n)}$ may be made equal to the expression and/or activity of the îth cellular constituent at the highest concentration of the drug n. Alternatively, the response at different levels of perturbations (e.g., different drug concentrations) $u_l$ may be interpolated to a smooth, piece-wise continuous function, e.g., by spline- or model-fitting, and $v_i^{(n)}$ made equal to some parameter of the interpolation. For example, in spline-fitting the response data to various levels of the perturbation n are interpolated by summing products of an appropriate spline interpolation function S multiplied by the measured data values, as illustrated by the equation $$v_i^{(n)}(u) = \sum_l S(u - u_l) v_i^{(n)}(u_l) \quad (2)$$

The variable "u" refers to an arbitrary value of the perturbation (e.g., the drug exposure level or concentration) where the perturbation response of the îth cellular constituent is to be evaluated. In general, S may be any smooth, or at least piece-wise continuous, function of limited support having a width characteristic of the structure expected in the response functions. An exemplary width can be chosen to be the distance over which the response function being interpolated rises from 10% to 90% of its asymptotic value. Exemplary S functions include linear and Gaussian interpolation.

In model-fitting, the response data to various levels $u_1$, of the perturbation n are interpolated by approximating the response by a single parameterized function. An exemplary model-fitting function appropriate for approximating transcriptional state data is the Hill function $$H(u) = \frac{a(u/u_0)^m}{1 + (u/u_0)^m} \quad (3)$$

The Hill function of Equation 3 above comprises the adjustable parameters of: (1) an amplitude parameter a, (2) an exponent m, and (3) an inflection point parameter $u_0$. The adjustable parameters are selected independently for each cellular constituent. Preferably, the adjustable parameters are selected so that for each cellular constituents of the drug response the sum of the squares of the distances of $H(u_1)$ from $v_i^{(n)}(u_1)$ is minimized. This preferable parameters adjustment method is well known in the art as a least squares fit of H( ) to $v_i^{(n)}$( ). Such a fit may be done using any of the many available numerical methods (see, e.g., Press et al., 1996, *Numerical Recipes in C*, 2nd Ed., Cambridge University Press, Chpts. 10 and 14; Branch et al., 1996, *Matlab Optimization Toolbox User's Guide*, Mathworks, Natick, Mass.). The response amplitude $v_i^{(n)}$ may then be selected to be equal to, e.g., the amplitude parameter a in Equation 3.

In an alternative embodiment, the response profile data may be categorical. For example, in a binary approximation the response amplitude $v_i^{(n)}$ is set equal to unity if cellular constituent i has a significant response to perturbation n, and is set equal to zero if there is no significant response. Alternatively, in a trinary approximation the response amplitude is set equal to +1 if cellular constituent i has a significant increase in expression and/or activity to perturbation n, is set equal to zero if there is no significant response, and is set equal to −1 if there is a significant decrease in expression and/or activity. Such embodiments are particularly preferred if it is known or suspected that the responses to which the response profile $v^{(n)}$ is to be compared do not have the same relative amplitudes as in $v^{(n)}$ but do involve the same cellular constituents. In yet other embodiments, it may be desirable to use "Mutual Information," as described and enabled, e.g., by Brunel (1998, *Neural Computation* 10(7):1731–1757).

In all of the above embodiments, it is often preferred to normalize the response profile by scaling all elements of the vector $v^{(n)}$ (i.e., $v_i^{(n)}$ for all i) by the same constant so that the vector length $|v^{(n)}|$ is unity. Generally, the vector length may be defined by $$|v^{(n)}|^2 = \sum_i (v_i^{(n)})^2 \quad (4)$$

In such embodiments, the projection operation described in Section 5.3.4 below yields a quantity which is proportional to the strength of the response component resembling the perturbation n, but does not depend on the over-all magnitude of the responses used to define the vector $v^{(n)}$.

5.3.2. Determining Co-varying Sets

A second aspect of the methods of the present invention involves arranging or grouping cellular constituents in the response profiles according to their tendency to co-vary in response to a perturbation. In particular, this Section describes specific embodiments for arranging the cellular constituents into co-varying sets. More specifically, the co-varying cellular constituent sets identified in the present invention may be used as basis sets as described in Section 5.3.4 below.

Clustering Algorithms

Preferably, the basis or co-varying sets of the present invention are identified by means of a clustering algorithm (i.e., by means of "clustering analysis"). Clustering algorithms of this invention may be generally classified as "model-based" or "model-independent" algorithms. In particular, model-based clustering methods assume that co-varying sets or clusters map to some predefined distribution shape in the cellular constituent "vector space." For example, many model-based clustering algorithms assume ellipsoidal cluster distributions having a particular eccentricity. By contrast, model-independent clustering algorithms make no assumptions about cluster shape. As is recognized by those skilled in the art, such model-independent methods are substantially identical to assuming "hyperspherical" cluster distributions. Hyperspherical cluster distributions are generally preferred in the methods of this invention, e.g., when the perturbation vector elements $v_i^{(n)}$ have similar scales and meanings, such as the abundances of different mRNA species.

The clustering methods and algorithms of the present invention may be further classified as "hierarchical" or "fixed-number-of groups" algorithms (see, e.g., S-Plus Guide to Statistical and Mathematical Analysis v.3.3, 1995, MathSoft, Inc.: StatSci. Division, Seattle, Wash.). Such algorithms are well known in the art (see, e.g., Fukunaga, 1990, *Statistical Pattern Recognition*, 2nd Ed., San Diego:

Academic Press; Everitt, 1974, *Cluster Analysis*, London: Heinemann Educ. Books; Hartigan, 1975, *Clustering Algorithms*, New York: Wiley; Sneath and Sokal, 1973, *Numerical Taxonomy*, Freeman; Anderberg, 1973, *Cluster Analysis for Applications*, New York: Academic Press), and include, e.g., hierarchical agglomerative clustering algorithms, the "k-means" algorithm of Hartigan (supra), and model-based clustering algorithms such as mclust by MathSoft, Inc. Preferably, hierarchical clustering methods and/or algorithms are employed in the methods of this invention. In a particularly preferred embodiment, the clustering analysis of the present invention is done using the hclust routine or algorithm (see, e.g., 'hclust' routine from the software package S-Plus, MathSoft, Inc., Cambridge, Mass.).

The clustering algorithms used in the present invention operate on a table of data containing gene expression measurements such as those described in Section 5.3.1 above. Specifically, the data table analyzed by the clustering methods of the present invention comprise an m×k array or matrix wherein m is the total number of conditions or perturbations and k is the number of cellular constituents measured and/or analyzed.

The clustering algorithms of the present invention analyze such arrays or matrices to determine dissimilarities between cellular constituents. Mathematically, dissimilarities between cellular constituents i and j are expressed as "distances" $I_{ij}$. For example, in one embodiment, the euclidian distance is determined according to the formula $$I_{i,j} = \left( \sum_n |v_i^{(n)} - v_j^{(n)}|^2 \right)^{1/2} \quad (5)$$

where $v_i^{(n)}$ and $v_j^{(n)}$ are the response of cellular constituents i and j respectively to the perturbation n. In other embodiments, the Euclidian distance in Equation 5 above is squared to place progressively greater weight on cellular constituents that are further apart. In alternative embodiments, the distance measure $I_{ij}$ is the Manhattan distance provided by $$I_{i,j} = \sum_n |v_i^{(n)} - v_j^{(n)}| \quad (6)$$

In embodiments wherein the response profile data is categorical (i.e., wherein each element $v_i^{(n)}=1$ or 0), the distance measure is preferably a percent disagreement defined by:

$$I_{i,j} = \frac{(\text{No. of } v_i^{(n)} \neq v_j^{(n)})}{n} \quad (7)$$

In another, particularly preferred embodiment, the distance is defined as $I_{ij}=1-r_{ij}$, where $r_{ij}$ is the "correlation coefficient" or normalized "dot product" between the response vectors $v_i$ and $v_j$. In particular, $r_{ij}$ is defined by $$r_{i,j} = \frac{v_i \cdot v_j}{|v_i||v_j|} \quad (8)$$

wherein the dot product $v_i \cdot v_j$ is defined by $$v_i \cdot v_j = \sum_n (v_i^{(n)} \times v_j^{(n)}) \quad (9)$$

and $|v_i|=(v_i \cdot v_i)^{1/2}$; $|v_j|=(v_j \cdot v_j)^{1/2}$.

In still other embodiments, the distance measure may be the Chebychev distance, the power distance, and percent disagreement, all of which are well known in the art. Most preferably, the distance measure is appropriate to the biological questions being asked, e.g., for identifying co-varying and/or co-regulated cellular constituents including co-varying or co-regulated genes. For example, in a particularly preferred embodiment, the distance measure $I_{i,j}=1-r_{i,j}$ with the correlation coefficient which comprises a weighted dot product of the response vector $v_i$ and $v_j$. Specifically, in this preferred embodiment, $r_{ij}$ is preferably defined by the equation $$r_{i,j} = \frac{\sum_n \frac{v_i^{(n)} v_j^{(n)}}{\sigma_i^{(n)} \sigma_j^{(n)}}}{\left[ \sum_n \left(\frac{v_i^{(n)}}{\sigma_i^{(n)}}\right)^2 \sum_n \left(\frac{v_j^{(n)}}{\sigma_j^{(n)}}\right)^2 \right]^{1/2}} \quad (10)$$

where $\sigma_i^{(n)}$ and $\sigma_j^{(n)}$ are the standard errors associated with the measurement of the i'th and j'th cellular constituents, respectively, in experiment n.

The correlation coefficients of Equations 8 and 10 are bounded between values of +1, which indicates that the two response vectors are perfectly correlated and essentially identical, and −1, which indicates that the two response vectors are "anti-correlated" or "anti-sense" (i.e., are opposites). These correlation coefficients are particularly preferable in embodiments of the invention where cellular constituent sets or clusters are sought of constituents which have responses of the same sign.

Figure 6:
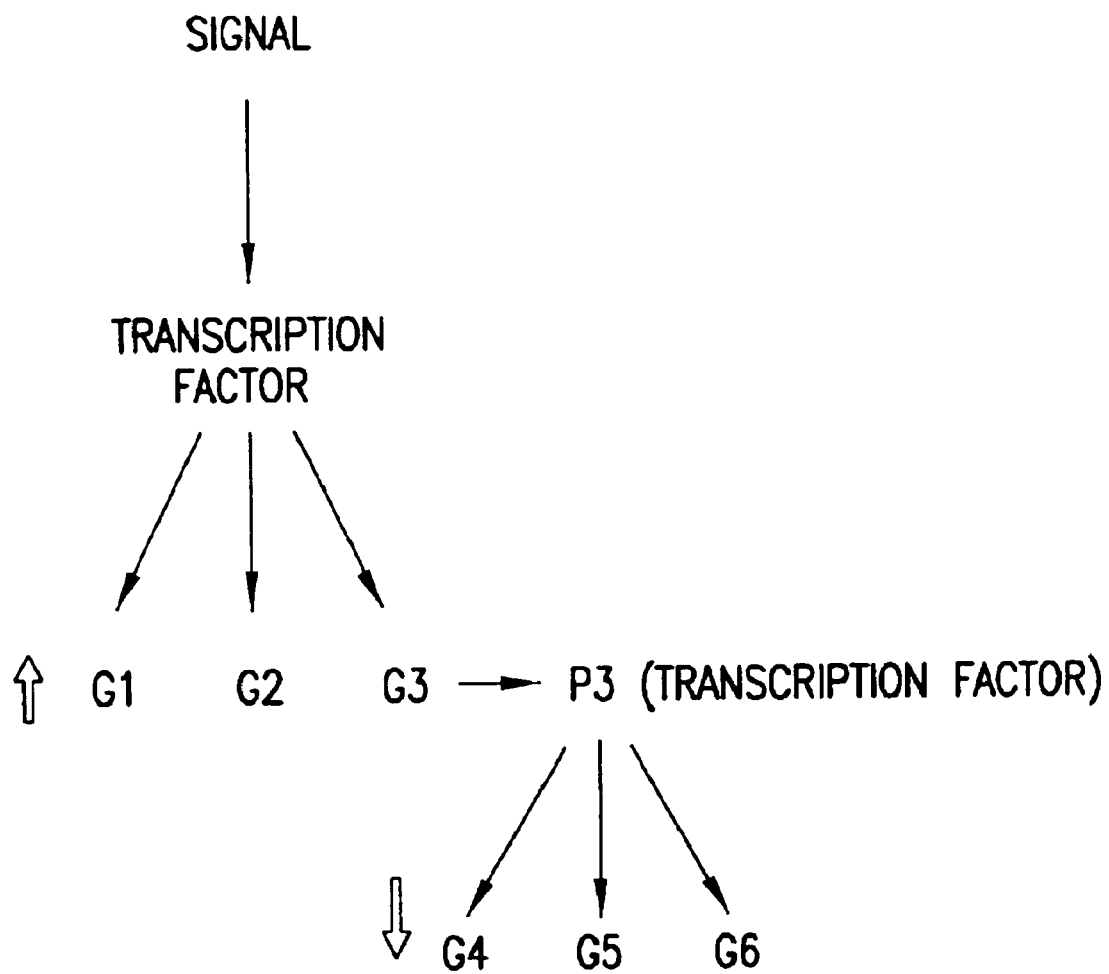
FIG. 6 illustrates an exemplary signaling cascade which includes a group of up-regulated genes (G1, G2, and G3) and a group of down-regulated genes (G4, G5, and G6).

In other embodiments, it is preferable to identify cellular constituent sets or clusters which are co-regulated or involved in the same biological responses or pathways, but which comprise similar and anti-correlated responses. For example, FIG. 6 illustrates a cascade in which a signal activates a transcription factor which up-regulated several genes, identified as G1, G2, and G3. In the example presented in FIG. 6, the product of G3 is a repressor element for several different genes, e.g., G4, G5, and G6. Thus, it is preferable to be able to identify all six genes G1–G6 as part of the same cellular constituent set or cluster. In such embodiments, it is preferable to use the absolute value of Equation 8 or 10, i.e., $|r_{ij}|$, as the correlation coefficient.

In still other embodiments, the relationships between co-regulated and/or co-varying cellular constituents may be even more complex, such as in instance wherein multiple biological pathways (e.g., signaling pathways) converge on the same cellular constituent to produce different outcomes. In such embodiments, it is preferable to use a correlation coefficient $r_{ij}=r_{ij}^{(change)}$ which is capable of identifying co-varying and/or co-regulated cellular constituents irrespective of the sign. The correlation coefficient specified by Equation 11 below is particularly useful in such embodiments.

$$r_{i,j}^{(change)} = \frac{\sum_n \left(\frac{v_i^{(n)}}{\sigma_i^{(n)}}\right)\left(\frac{v_j^{(n)}}{\sigma_j^{(n)}}\right)}{\left[ \sum_n \left(\frac{v_i^{(n)}}{\sigma_i^{(n)}}\right)^2 \sum_n \left(\frac{v_j^{(n)}}{\sigma_j^{(n)}}\right)^2 \right]^{1/2}} \quad (11)$$

Generally, the clustering algorithms used in the methods of the invention also use one or more linkage rules to group cellular constituents into one or more sets or "clusters." For example, single linkage or the nearest neighbor method determines the distance between the two closest objects (i.e., between the two closest cellular constituents) in a data table. By contrast, complete linkage methods determine the greatest distance between any two objects (i.e., cellular constituents) in different clusters or sets. Alternatively, the unweighted pair-group average evaluates the "distance" between two clusters or sets by determining the average distance between all pairs of objects (i.e., cellular constituents) in the two clusters. Alternatively, the weighted pair-group average evaluates the distance between two clusters or sets by determining the weighted average distance between all pairs of objects in the two clusters, wherein the weighing factor is proportional to the size of the respective clusters. Other linkage rules, such as the unweighted and weighted pair-group centroid and Ward's method, are also useful for certain embodiments of the present invention (see, e.g., Ward, 1963, *J. Am. Stat. Assn* 58:236; Hartigan, 1975, *Clustering Algorithms*, New York: Wiley).

Figure 7:
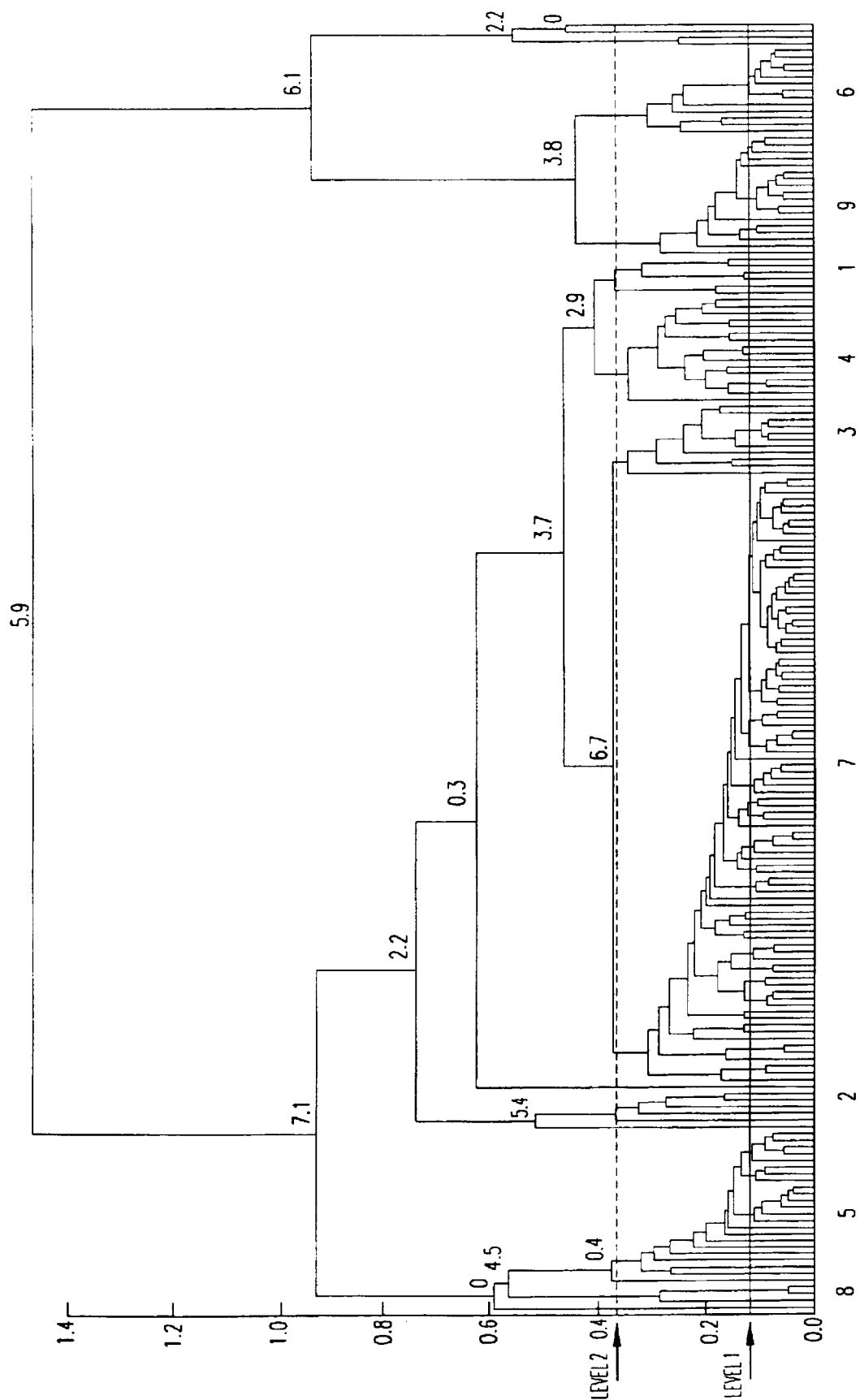
FIG. 7 is the clustering tree, obtained by the hclust clustering algorithm, for the 34 experiments illustrated in FIGS. 2 and 3.

Once a clustering algorithm has grouped the cellular constituents from the data table into sets or cluster, e.g., by application of linkage rules such as those described supra, a clustering "tree" may be generated to illustrate the clusters of cellular constituents so determined. FIG. 7 illustrates an exemplary clustering tree generated by the hclust clustering algorithm upon analysis of the 34×185 table of response profile data illustrated in FIG. 2A (see Section 5.2 above), and using the distance metric $I_{i,j}=1-r_{i,j}$. The measured response data $\{v_i^{(n)}\}$ comprise the logarithm to the base 10 of the ratio between abundances of each transcript i in the pair of conditions (i.e., perturbation and no perturbation) comprising each differential experiment n.

Genesets may be readily defined based on the branchings of a clustering tree such as the one illustrated in FIG. 7. In particular, genesets may be defined based on the many smaller branchings of a clustering tree, (e.g., at LEVEL 1 indicated in FIG. 7), or, optionally, larger genesets may be defined corresponding to the larger branches of a clustering tree (e.g., at LEVEL 2 in FIG. 7). Preferably, the choice of branching level at which genesets are defined matches the number of distinct response pathways expected. In embodiments wherein little or no information is available to indicate the number of pathways, the genesets should be defined according to the branching level wherein the branches of the clustering tree are "truly distinct."

"Truly distinct," as used herein, may be defined, e.g., by a minimum distance value between the individual branches. For example, in FIG. 7 the distance between truly distinct genesets is the vertical coordinate of the horizontal connector joining two branches. Typically, the distance values between truly distinct genesets are in the range of 0.2 to 0.4, where a distance of zero corresponds to perfect correlation and a distance of unity corresponds to no correlation. However, distances between truly distinct genesets may be larger in certain embodiments, e.g., wherein there is poorer quality data or fewer experiments n in the response profile data. Alternatively, in other embodiments, e.g., having better quality data or more experiments n in the profile dataset, the distance between truly distinct genesets may be less than 0.2.

For example, if the horizontal cut indicated by the dotted line in FIG. 7 is used, and only those branches having two or more cellular constituents below the cut are accepted as genesets, nine genesets are obtained. These nine genesets in fact reflect pathways involving the calcineurin protein, the PDR gene, the Gcn4 transcription factor, RNR (a DNA repair gene), and cellular stress responses. Thus, the genesets identified in FIG. 7, and genesets identified by cluster analysis in general, have an underlying biological significance.

Statistical Significance

Preferably, truly distinct cellular constituent sets are defined by means of an objective test of statistical significance for each bifurcation in the clustering tree. For example, in one aspect of the invention, truly distinct cellular constituent sets arc defined by means of a statistical test which uses Monte Carlo randomization of the experiment index n for the responses of each cellular constituent across the set of experiments. For example, in one preferred embodiment, the experiment index n of each cellular constituent's response $v_i^{(n)}$ is randomly permutated, as indicated by $$v_i^{(n)} \to v_i^{\Pi(n)} \tag{12}$$

More specifically, a large number of permutations of the experiment index n is generated for each cellular constituent's response. Preferably, the number of permutations is from about 50 to about 1000, more preferably from about 50 to about 100. For each branching of the original clustering tree, and for each permutation of the experiment index:

(1) hierarchical clustering is performed on the permutated data, preferably using the same clustering algorithm as used for the original unpermuted data (e.g., hclust for the clustering tree in FIG. 7); and (2) the fractional improvement f in the total scatter is computed with respect to the cluster centers in going from one cluster to two clusters.

In particular, the fractional improvement f is computed according to $$f = 1 - \frac{\sum D_i^{(1)}}{\sum D_i^{(2)}} \tag{13}$$

wherein $D_i$ is the square of the distance measure for cellular constituent i with respect to the center (i.e., the mean) of its assigned cluster. The superscripts (1) and (2) indicate whether the square of the distance measure $D_i$ is made with respect to (1) the center of its entire branch, or (2) the center of the appropriate cluster out of the two clusters. The distance function $D_i$ in Equation 13 may be defined according to any one of several embodiments. In particular, the various embodiments described supra for the definition of $I_{ij}$ may also be used to define $D_i$ in Equation 13.

The distribution of fractional improvements obtained from the above-described Monte Carlo methods provides an estimate of the distribution under the null hypothesis, i.e., the hypothesis that a particular branching in a cluster tree is not significant or distinct. A significance can thus be assigned to the actual fractional improvement (i.e., the fraction improvement of the unpermuted data) by comparing the actual fractional improvement to the distribution of fractional improvements for the permuted data. Preferably, the significance is expressed in terms of the standard deviation of the null hypothesis distribution, e.g., by fitting a log normal model to the null hypothesis distribution obtained from the permuted data. For example, the numbers displayed at the bifurcations in FIG. 7 are the significance, in multiples of the standard deviation of the null hypothesis distribution, of each bifurcation. Numbers greater than about 2, for example, indicate that the branching is significant at the 95% confidence level.

In more detail, an objective statistical test is preferably employed to determine the statistical reliability of the grouping decisions of any clustering method or algorithm. Preferably, a similar test is used for both hierarchical and non-hierarchical clustering methods. More preferably, the statistical test employed comprises (a) obtaining a measure of the compactness of the clusters determined by one of the clustering methods of this invention, and (b) comparing the obtained measure of compactness to a hypothetical measure of compactness of cellular constituents regrouped in an increased number of clusters. For example, in embodiments wherein hierarchical clustering algorithms, such as hclust, are employed, such a hypothetical measure of compactness preferably comprises the measure of compactness for clusters selected at the next lowest branch in a clustering tree (e.g., at LEVEL 1 rather than at LEVEL 2 in FIG. 7). Alternatively, in embodiments wherein non-hierarchical clustering methods or algorithms are employed, e.g., to generate N clusters, the hypothetical measure of compactness is preferably the compactness obtained for N+1 clusters by the same methods.

Cluster compactness may be quantitatively defined, e.g., as the mean squared distance of elements of the cluster from the "cluster mean," or, more preferably, as the inverse of the mean squared distance of elements from the cluster mean. The cluster mean of a particular cluster is generally defined as the mean of the response vectors of all elements in the cluster. However, in certain embodiments, e.g., wherein the absolute value of Equation 8 or 10 is used to evaluate the distance metric (i.e., $I_{ij}=1-|r_{ij}|$) of the clustering algorithm, such a definition of cluster mean is problematic. More generally, the above definition of mean is problematic in embodiments wherein response vectors may be in opposite directions such that the above defined cluster mean could be zero. Accordingly, in such embodiments, it is preferable to chose a different definition of cluster compactness, such as, but not limited to, the mean squared distance between all pairs of elements in the cluster. Alternatively, the cluster compactness may be defined to comprise the average distance (or more preferably the inverse of the average distance) from each element (e.g., cellular constituent) of the cluster to all other elements in that cluster.

Preferably, Step (b) above of comparing cluster compactness to a hypothetical compactness comprises generating a non-parametric statistical distribution for the changed compactness in an increased number of clusters. More preferably, such a distribution is generated using a model which mimics the actual data but has no intrinsic clustered structures (i.e., a "null hypothesis" model). For example, such distributions may be generated by (a) randomizing the perturbation experiment index n for each actual perturbation vector $v_i^{(n)}$, and (b) calculating the change in compactness which occurs for each distribution, e.g., by increasing the number of clusters from N to N+1 (non-hierarchical clustering methods), or by increasing the branching level at which clusters are defined (hierarchical methods).

Figure 8:
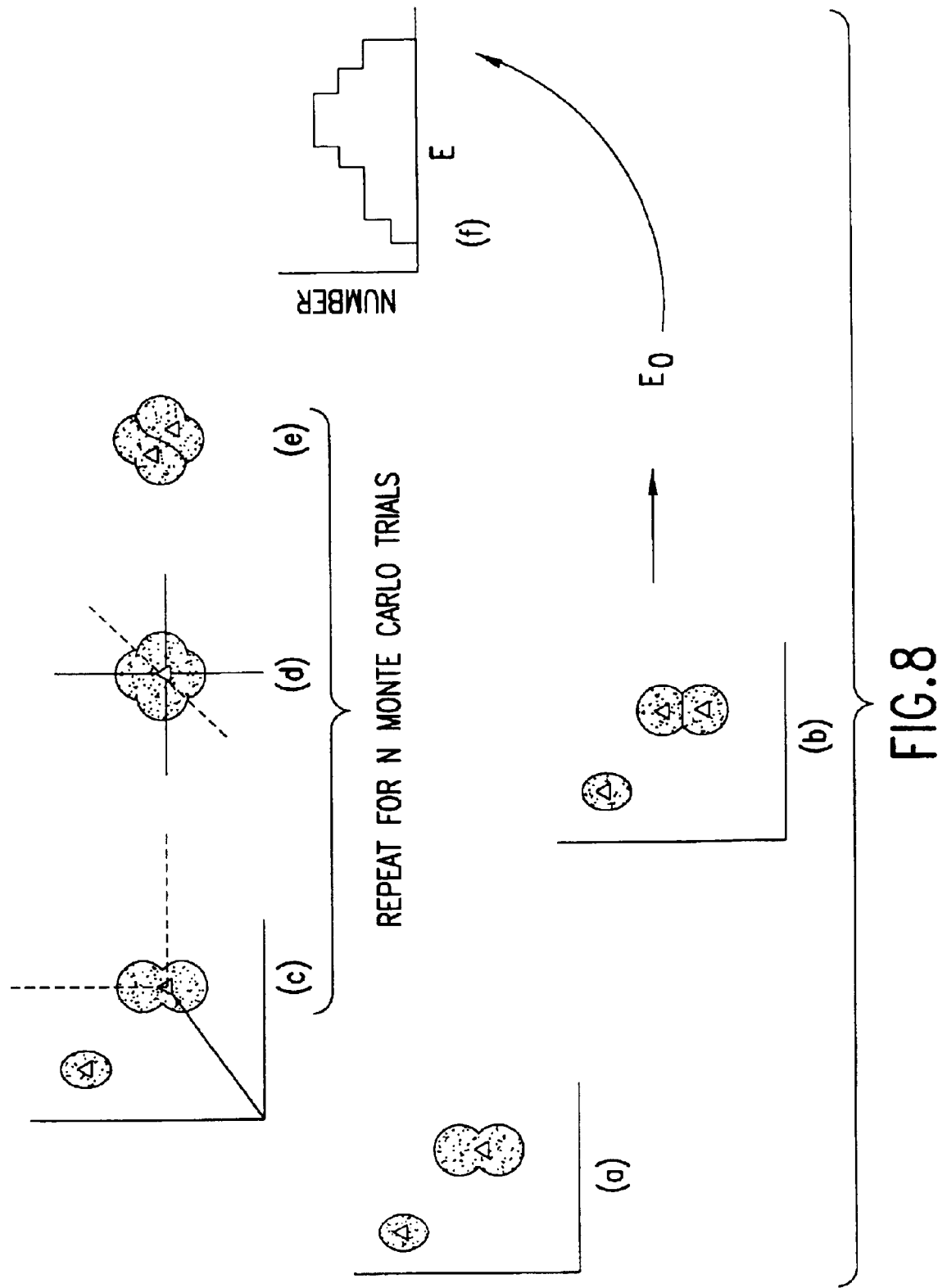
FIG. 8 illustrates an exemplary, two-dimensional embodiment of the Monte Carlo method for assigning significance to cluster subdivisions.

Such a process is illustrated in FIG. 8 for an exemplary, non-hierarchical embodiment of the clustering methods wherein the response vectors are two-dimensional (i.e., there are two perturbation experiments, n=1, 2) and have lengths $|v_i|=2$. Their response vectors are therefore displayed in FIG. 8 as points in two-dimensional space. In the present example, two apparent clusters can be distinguished. These two clusters are shown in FIG. 8A, and comprise a circular cluster and a dumbbell-shaped cluster. The cluster centers are indicated by the triangle symbol (▲). As is apparent to one skilled in the art, the distribution of perturbation vectors in FIG. 8 could also be divided into three clusters, illustrated in FIG. 8B along with their corresponding centers. As will also be apparent to one skilled in the art, the two new clusters in FIG. 8B are each more compact than the one dumbbell shaped cluster in FIG. 8A. However, such an increase in compactness may not be statistically significant, and so may not be indicative of the actual or unique cellular constituent sets. In particular, the compactness of a set of N clusters may be defined in this example as the inverse of the mean squared distance of each element from its cluster center, i.e., as $1/I^{(N)}_{mean}$. In general, $I^{(N-1)}_{mean} < I^{(N)}_{mean}$. Regardless of whether there are additional "real" cellular constituent sets. Accordingly, the statistical methods of this invention may be used to evaluate the statistical significance of the increased compactness which occurs, e.g., in the present example, when the number of clusters is increased from N=2 to N+1=3.

In an exemplary embodiment, the increased compactness is given by the parameter E, which is defined by the formula $$E = \frac{I^{(N)}_{mean} - I^{(N-1)}_{mean}}{I^{(N-1)}_{mean}} \qquad (14)$$

However, other definitions are apparent to those skilled in the art which may also be used in the statistical methods of this invention. In general, the exact definition of E is not crucial provided it is monotonically related to increase in cluster compactness.

The statistical methods of this invention provide methods to analyze the significance of E. Specifically, these methods provide an empirical distribution approach for the analysis of E by comparing the actual increase in compactness, $E_0$ for actual experimental data, to an empirical distribution of E values determined from randomly permuted data (e.g., by Equation 10 above). In the two-dimensional example illustrated in FIG. 8, such a translation comprises, first, randomly swapping the perturbation indices n=1,2 in each perturbation vector with equal probability. More specifically, the coordinates (i.e., the indices) of the vectors in each cluster being subdivided are "reflected" about the cluster center, e.g., by first translating the coordinate axes to the cluster center as shown in FIG. 8C. The results of such an operation are shown, for the two-dimensional example, in FIG. 8D. Second, the randomly permuted data are reevaluated by the cluster algorithms of the invention, most preferably by the same cluster algorithm used to determine the original cluster (s), so that new clusters are determined for the permuted data, and a value of E is evaluated for these new clusters (i.e., for splitting one or more of the new clusters). Steps one and two above are repeated for some number of Monte Carlo trials to generate a distribution of E values. Preferably, the number of Monte Carlo trials is from about 50 to about 1000, and more preferably from about 50 to about 100. Finally, the actual increase in compactness, i.e., $E_0$, is compared to this empirical distribution of E values. For example, if M Monte Carlo simulation are performed, of which x have E values greater than $E_0$, then the confidence level in the number of clusters may be evaluated from 1-x/M. In particular, if M=100, and x=4, then the confidence level that there is no real significance in increasing the number of clusters is 1-4/110=96%.

The above methods are equally applicable to embodiments comprising hierarchical clusters and/or a plurality of elements (e.g., more than two cellular constituents). For example, the cluster tree illustrated in FIG. 7. As noted above, this clustering tree was obtained using the hclust algorithm for 34 perturbation response profiles comprising 185 cellular constituents which had significant responses. Using the clusters defined by the branches at LEVEL 2 of this tree, 100 Monte Carlo simulations were performed randomizing the 34 experimental indices and empirical distributions for the improvements in compactness E were generated for each branching in the tree. The actual improvement in compactness $E_0$ at each branch was compared with its corresponding distribution. These comparisons are shown by the numbers at each branch in FIG. 7. Specifically, these numbers indicate the number of standard deviations in the distribution by which $E_0$ exceed the average value of E. The indicated significance correspond well with the independently determined biological significance of the branches. For example, as noted in Section 5.3.5 below, the main branch indicated in FIG. 7 by the number five (bottom label) comprises genes regulated via the calcineurin protein, whereas the branch labeled number 7 primarily comprises genes regulated by the Gcn4 transcription factor.

Classification Based Upon Mechanisms of Regulation

Cellular constituent sets can also be defined based upon the mechanism of the regulation of cellular constituents. For example, genesets can often be defined based upon the regulation mechanism of individual genes. Genes whose regulatory regions have the same transcription factor binding sites are more likely to be co-regulated, and, as such, are more likely to co-vary. In some preferred embodiments, the regulatory regions of the genes of interest are compared using multiple alignment analysis to decipher possible shared transcription factor binding sites (see, e.g., Stormo and Hartzell, 1989, *Proc. Natl. Acad. Sci.* 86:1183–1187; and Hertz and Stormo, 1995, *Proc. of 3rd Intl. Conf. on Bioinformatics and Genome Research*, Lim and Cantor, eds., Singapore: World Scientific Publishing Co., Ltd., pp.201–216). For example, common promoter sequence responsive to Gcn4 in 20 genes is likely to be responsible for those 20 genes co-varying over a wide variety of perturbations.

Co-regulated and/or co-varying genes may also be in the up- or down-stream relationship where the products of up-stream genes regulate the activity of down-stream genes. For example, as is well known to those of skill in the art, there are numerous varieties of gene regulation networks. Accordingly, and as is also understood by those of skill in the art, the methods of the present invention are not limited to any particular kind of gene regulation mechanism. If it can be derived or determined from their mechanisms of regulation, whatever that mechanism happens to be, that two or more genes are co-regulated in terms of their activity change in response to perturbation, those two or more genes may be clustered into a geneset.

In many embodiments of the present invention, knowledge of the exact regulation mechanisms of certain cellular constituents may be limited and/or incomplete. In such embodiments, it may be preferred to combine cluster analysis methods, described above, with knowledge of regulatory mechanisms to derive better defined, i.e., refined cellular constituent sets. For example, in some embodiments, clustering may be used to cluster genesets when the regulation of genes of interest is partially known. In particular, in many embodiments, the number of genesets may be predetermined by understanding (which may be incomplete or limited) or the regulation mechanism or mechanisms. In such embodiments, the clustering methods may be constrained to produce the predetermined number of clusters. For example, in a particular embodiment promoter sequence comparison may indicate that the measured genes should fall into three distinct genesets. The clustering methods described above may then be constrained to generate exactly three genesets with the greatest possible distinction between those three sets.

Refinement of Cellular Constituent Sets

Cellular constituent sets, such as cellular constituent sets identified by any of the above methods, including combinations thereof, may be refined using any of several sources of corroborating information. Examples of corroborating information which may be used to refine cellular constituent sets include, but are by no means limited to, searches for common regulatory sequence patterns, literature evidence for co-regulations, sequence homology (e.g., of genes or proteins), and known shared function.

Figure 9:
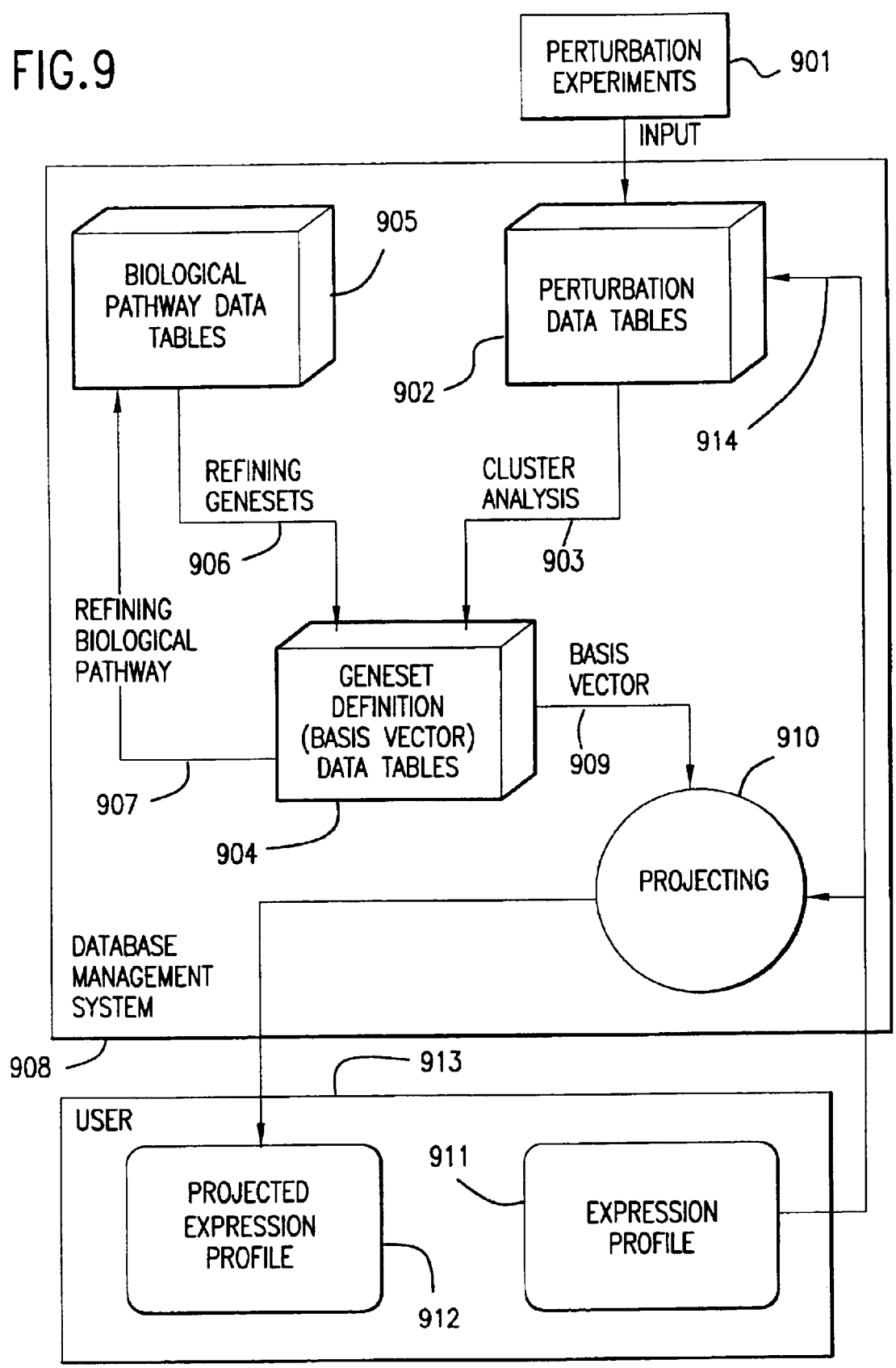
FIG. 9 illustrates an exemplary embodiment of a geneset database management system.
Figure 10A:
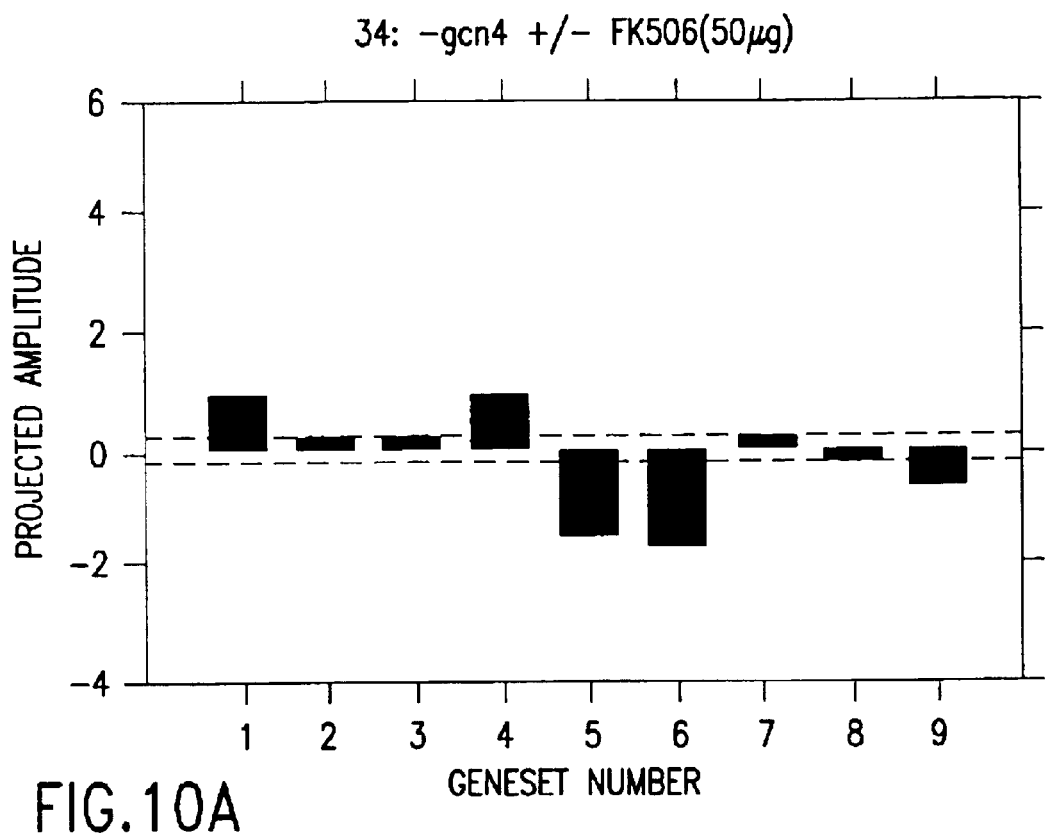
FIGS. 10A–10H show bar charts indicating projected profiles for experiment 15, 18, 28–32, and 34 of FIG. 3.
Figure 10B:
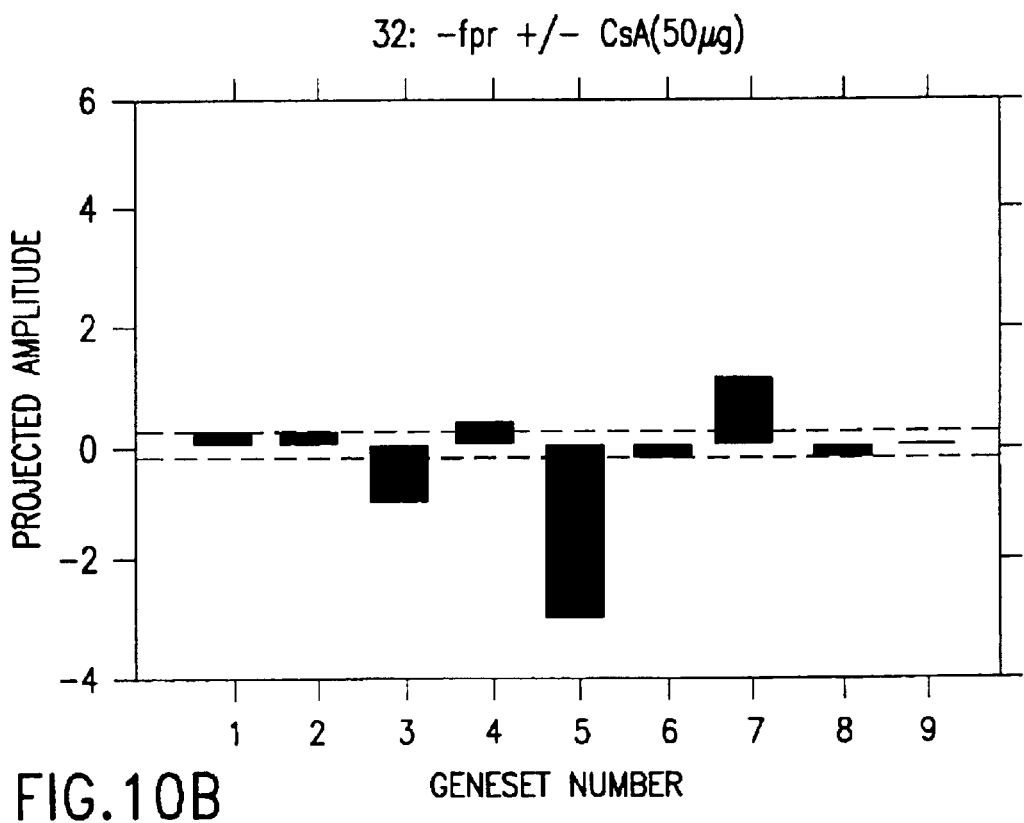
Figure 10C:
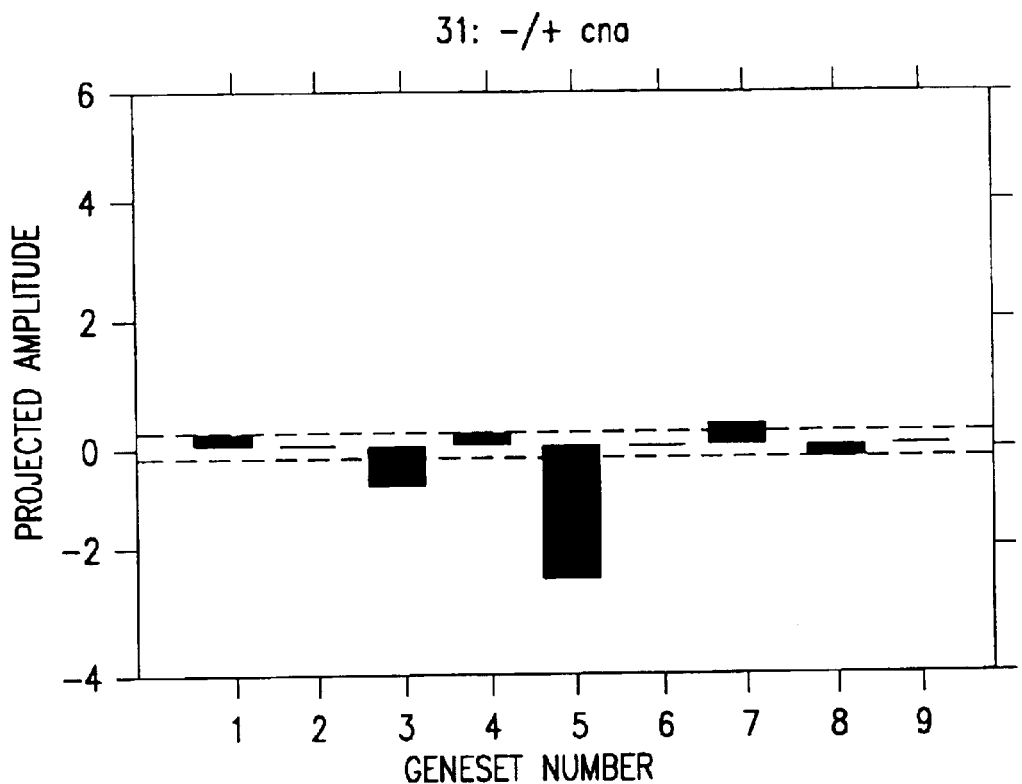
Figure 10D:
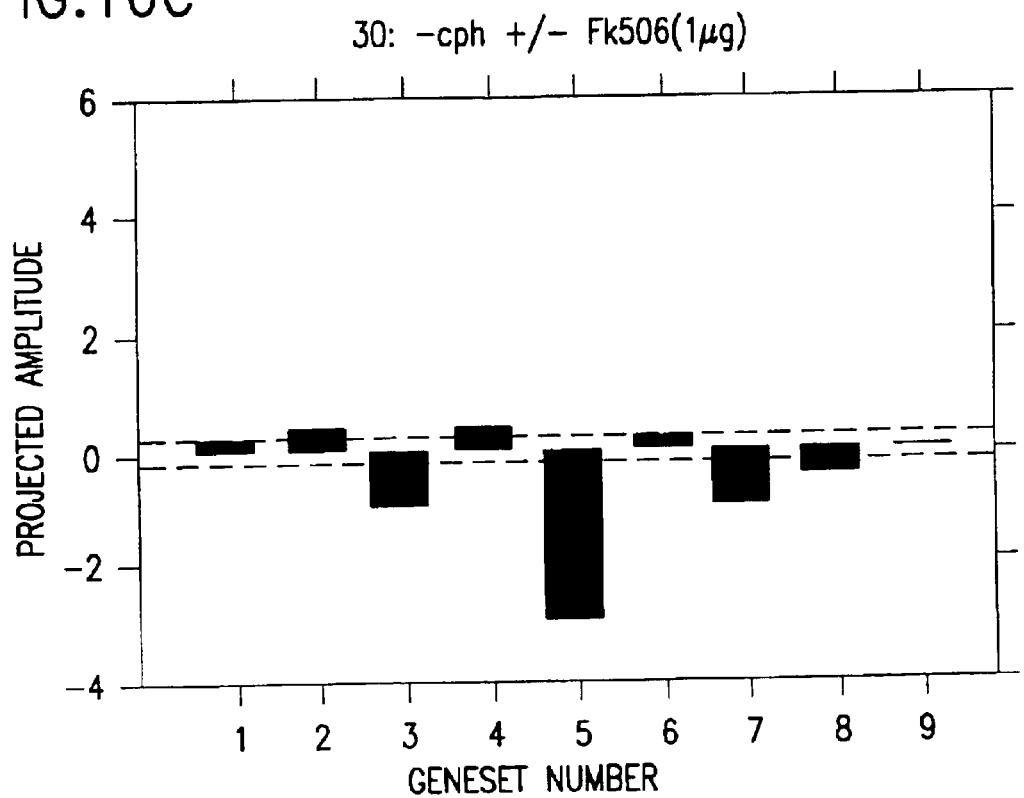
Figure 10E:
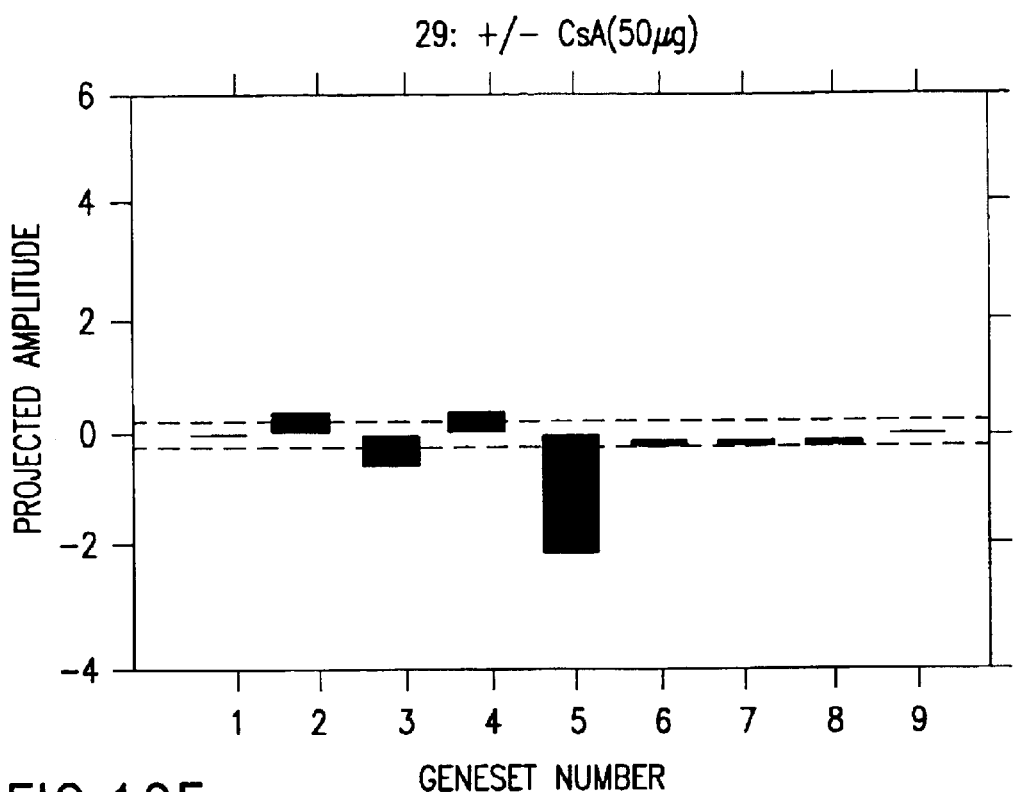
Figure 10F:
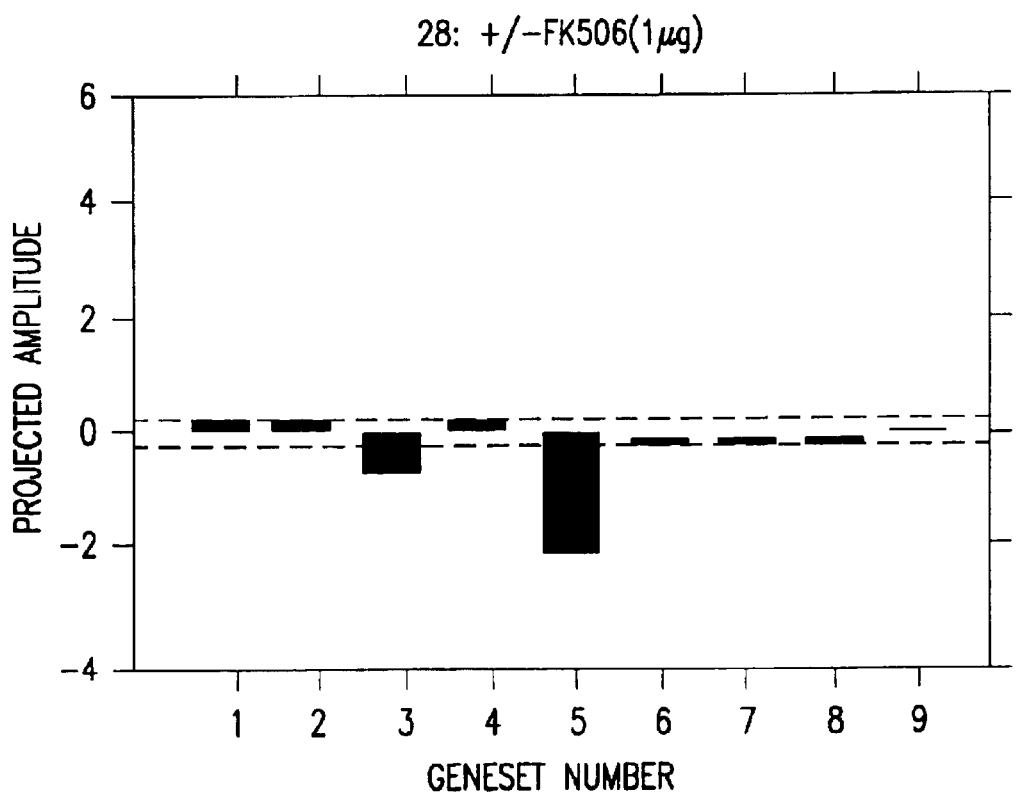
Figure 10G:
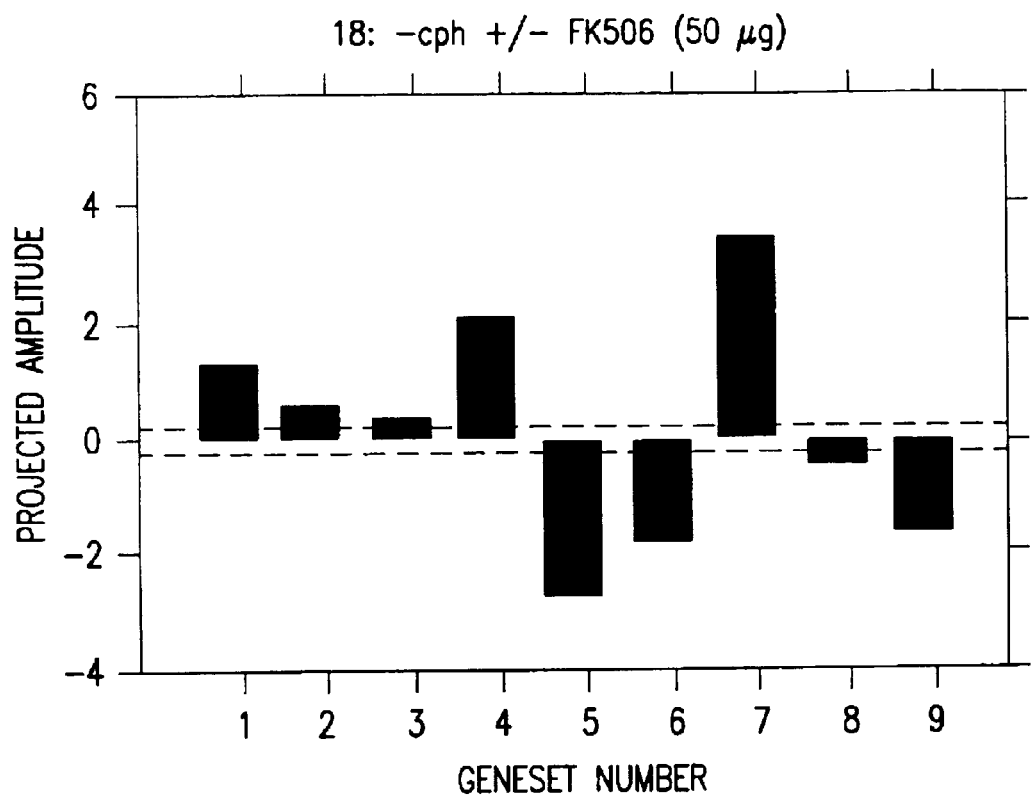
Figure 10H:
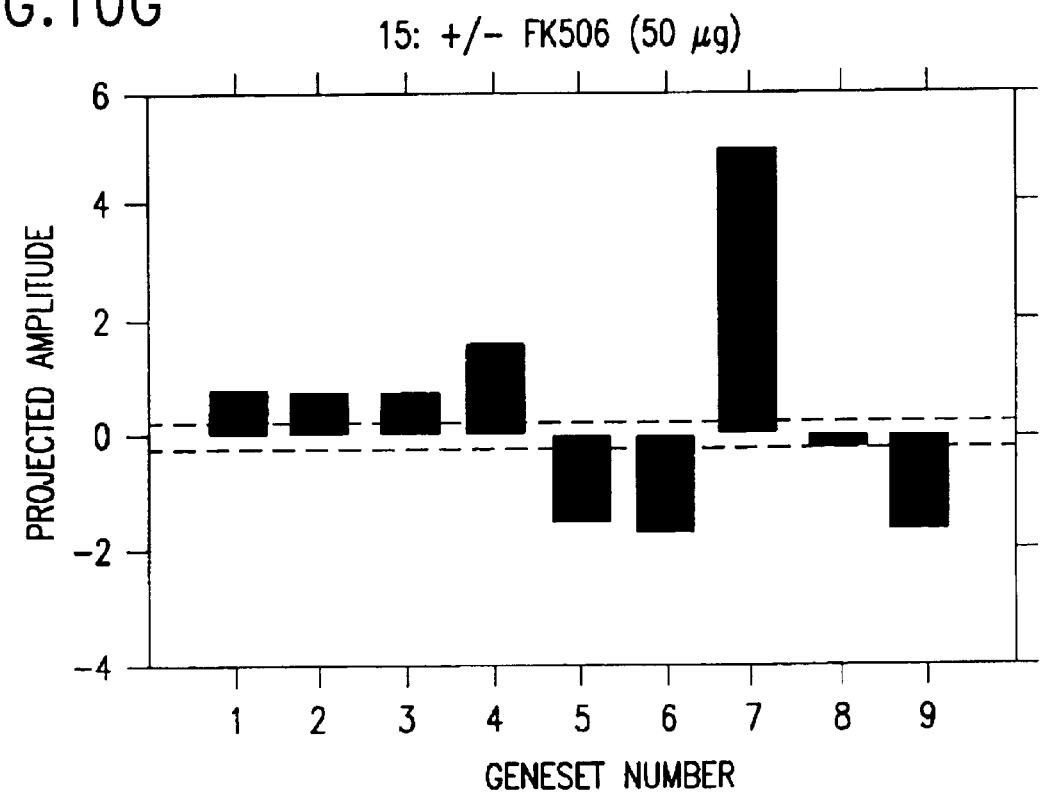

In preferred embodiments, cellular constituent databases are used for the refinement of genesets. In particularly preferred embodiments the database is a "dynamic database." For example, in certain embodiments, a database containing raw data for cluster analysis of cellular constituent sets (e.g., for genesets) is used to continuously update geneset definitions. FIG. 9 shows an exemplary embodiment of such a dynamic geneset database. Data from perturbation experiments (901) are input into data tables (902) in the perturbation database management system (908). Geneset definitions, e.g., in the form of basis vectors, are continuously generated based upon this updated data, using, e.g., cluster analysis methods (903) and/or biological pathway definitions (905 and 906). The resulting geneset definition datatable (904) contains these updated geneset definitions.

The geneset definitions may be used, e.g., for refining biological pathway datatables. The geneset definition tables are preferably accessible by user-submitted projection request. For example, a user (913) may access the database management system by submitting expression profile (911). The database management system may project (910) the expression profile into a projected expression profile (see, e.g., Section 5.3.4 below for a discussion of the projection process). The user-submitted expression profile may also be optionally added to the perturbation data tables (902).

Such a dynamic database is constantly productive in the sense that it provides useful geneset definitions with the first, limited set of perturbation data. As it is updated, the database may continuously refine the geneset definitions to provide more useful geneset definitions as more perturbation data become available.

In certain embodiments of the database, perturbation data and geneset definition data are stored in a series of relational tables in digital computer storage media. Preferably, the database is implemented in distributed system environments with client/server implementation, allowing multiuser and/or remote access. Relational database management systems and client/server environments are well documented in the art (see, e.g., Nath, 1995, *The Guide to SQL Server*, 2nd ed., Addison-Wesley Publishing Co.).

Definition of Basis Vectors

Once cellular constituent sets have been obtained or provided, e.g., by means of a clustering analysis algorithm such as hclust, a set of basis vectors e may be obtained or provided based on those cellular constituent sets. Such basis vectors may be used for the profile projection methods described in Section 5.3.4 below.

Preferably, the set of basis vectors has k×N dimensions, where k is the number of cellular constituents, and N is the number of cellular constituent sets. In particular, the set of basis vectors e obtained or provided from the cellular constituent sets comprises a matrix of basis vectors $$e = [e^{(1)}, \ldots, e^{(q)}, \ldots, e^{(N)}] \tag{15}$$

where each basis vector $e^{(q)}$ may be defined by the column vector $$e^{(q)} = \begin{pmatrix} e_1^{(q)} \\ \vdots \\ e_i^{(q)} \\ \vdots \\ e_k^{(q)} \end{pmatrix} \quad (16)$$

Preferably, the elements $e_i^{(q)}$ of the basis vectors are assigned the values:

$e_i^{(q)} = \pm 1$ if cellular constituent i is a member of cellular constituent set q (wherein the sign is chosen so that constituents which are anti-correlated in their responses across a set of perturbations have opposite signs, and constituents with positive correlation have the same sign); and $e_i^{(q)} = 0$ if cellular constituent i is not a member of cellular constituent set q.

Alternatively, the non-zero elements of $e^{(q)}$ may be given magnitudes which are proportional to the typical response magnitude of that element.

In preferred embodiments, the elements $e_i^{(q)}$ are normalized so that each $e^{(q)}$ has a length equal to unity, e.g., by dividing each element by the square root of the number of cellular constituents in cellular constituent set q (i.e., by the number of elements $e_i^{(q)}$ which are non-zero for a particular cellular constituent set index q. In such embodiments, random measurement errors in profiles project onto the basis vectors in such a way that the amplitudes tend to be comparable for each cellular constituent set. Thus, normalization prevents large cellular constituent sets from dominating the results of calculations involving those sets.

Re-ordering the Cellular Constituent Index

As noted in Section 5.2 above, in preferable embodiments of the present invention, the cellular constituents are re-ordered according the cellular constituent sets or clusters obtained or provided by the above-described methods, and visually displayed. Analytically, such a reordering corresponds to transforming a particular original biological response profile, such as a particular perturbation response profile, e.g., $v^{(n)} = \{v_i^{(n)}\}0$ to the re-ordered profile $\{v_{\Pi(i)}^{(n)}\}$, where i is the cellular constituent index.

An exemplary re-ordering of the cellular constituents is indicated in FIG. 2. In particular, FIG. 2A shows a false color display of a plurality of genetic transcripts (i.e., cellular constituents; horizontal axis) measured in a plurality of experiments wherein cells are exposed to different perturbations (i.e., perturbation response profiles, vertical index). FIG. 2B illustrates a coregulation tree generated by the hclust algorithm from the data in FIG. 2A. FIG. 2C illustrates the visual display of the data in FIG. 2A wherein the transcripts have been re-ordered according to the clusters in the coregulation tree.

5.3.3. Grouping Measured Response Profiles

A third aspect of the analytical methods of the present invention involves methods for grouping or clustering and re-ordering of the perturbation response profiles $v^{(n)}$ into clusters or sets which are associated with similar biological effects of a perturbation. Such methods are exactly analogous to the methods described in Section 5.3.2 above. In particular, the methods and operations described in Section 5.3.2 above which are applied to the cellular constituent index i of the perturbation response profile elements $v_i^{(n)}$ may also be applied to the perturbation index n.

Such an operation is illustrated in FIG. 2. In particular, FIG. 2D illustrates a visual display of the data shown in FIG. 2C wherein the experimental (i.e., perturbation) index n has been reordered according to the clustering and other analysis methods described in Section 5.3.2 above. The result is a visual display in which experiments with similar profiles are place contiguously. Such a display greatly facilitates the identification of co-regulated genesets. In particular, by visually inspecting such a display, a user can readily identify those genesets which co-vary in groups of experiments. Such a display also facilitates the identification of experiments which are associated with similar biological responses.

The analytical methods of this invention thus include methods of "two-dimensional" cluster analysis. Such two-dimensional cluster analysis methods simply comprise (1) clustering cellular constituents into sets that are co-varying in biological profiles, and (2) clustering biological profiles into sets that effect similar cellular constituents (preferably in similar ways). The two clustering steps may be performed in any order and according to the methods described above.

Such two-dimensional clustering techniques are useful, as noted above, for identifying sets of genes and experiments of particular interest. For example, the two-dimensional clustering techniques of this invention may be used to identify sets of cellular constituents and/or experiments that are associated with a particular biological effect of interest, such as a drug effect. The two-dimensional clustering techniques of this invention may also be used, e.g., to identify sets of cellular constituents and/or experiments that are associated with a particular biological pathway of interest. In one preferred embodiment of the invention, such sets of cellular constituents and/or experiments are used to determine consensus profiles for a particular biological response of interest. In other embodiments, identification of such sets of cellular constituents and/or experiments provide more precise indications of groupings cellular constituents, such as identification of genes involved in a particular biological pathway or response of interest. Accordingly, another preferred embodiment of the present invention provides methods for identifying cellular constituents, particularly new genes, that are involved in a particular biological effect, of interest e.g., a particular biological pathway. Such cellular constituents are identified according to the cluster-analysis methods described above. Such cellular constituents (e.g., genes) may be previously unknown cellular constituents, or known cellular constituents that were not previously known to be associated with the biological effect of interest.

The present invention further provides methods for the iterative refinement of cellular constituent sets and/or clusters of response profiles (such as consensus profiles). In particular, dominant features in each set of cellular constituents and or profiles identified by the cluster analysis methods of this invention may be blanked out, e.g., by setting their elements to zero or to the mean data value of the set. The blanking out of dominant features may be done by a user, e.g., by manually selecting features to blank out, or automatically, e.g., by automatically blanking out those elements whose response amplitudes are above a selected threshold. The cluster analysis methods of the invention are then reapplied to the cellular constituent and/or profile data. Such iterative refinement methods may be used, e.g., to identify other potentially interesting but more subtle cellular constituent and/or experiment associations that were not identified because of the dominant features.

5.3.4. Projecting onto Basis Cellular Constituent Sets

A fourth aspect of the analytical methods of the present invention involves methods for representing biological profiles, such as response profiles (including perturbation response profiles), in terms of basis cellular constituent sets. Such methods are commonly known to those skilled in the art as "projection."

In particular, as noted in Section 5.3.2 above, the basis vectors obtained from a set of cellular constituents, such as from a geneset, can be represented as the matrix $$e = [e^{(1)}, \ldots, e^{(q)}, \ldots, e^{(N)}] \quad (17)$$

where each basis vector $e^{(q)}$ is defined by:

$$e^{(q)} = \begin{matrix} e_1^{(q)} \\ \vdots \\ e_i^{(q)} \\ \vdots \\ e_k^{(q)} \end{matrix} \quad (18)$$

where k is the total number of cellular constituents being evaluated, and N is the total number of cellular constituent sets. As noted above, a biological response profile p may also be represented as the vector $$p = [p_1, \ldots, p_i, \ldots p_k] \quad (19)$$

Such a response profile may be, e.g., a particular perturbation response profile $v^{(n)}$ used to determine the cellular constituent sets, or, more typically, a new response profile for some novel experiment not used to determine the cellular constituent sets. The response profile p is preferably represented in terms of the basis vectors as a "projected profile" P by means of the operation:

$$P = p \cdot e \quad (20)$$

Equation 20 above is well known to those skilled in the art as the "matrix dot product" of p and e. As is also recognized by those skilled in the art, the matrix dot product of p and e generates a new vector $$P = [P_1, \ldots P_q, \ldots P_N] \quad (21)$$

wherein the elements $P_q$ of the vector P are specified by $$P_q = p \cdot e^{(q)} = \sum_i p_i \times e_i^{(q)} \quad (22)$$

In other embodiments, the projection of a response profile p onto a basis set of cellular constituents simply comprises the average of the expression value (in p) of the genes within each geneset. In some aspects of such embodiments, the average may be weighted, e.g., so that highly expressed genes do not dominate the average value.

Similarities and differences between two or more projected profiles, for example between $P^{(a)}$ and $P^{(b)}$ are typically more apparent than are similarities between the original profiles, e.g. $p^{(a)}$ and $p^{(b)}$, before projection. Thus it is preferable, in practicing the methods of the present invention, to compare projected response profiles. In particular, measurement errors in extraneous genes are typically excluded or averaged out by projection. Thus, any element of a projected profile, e.g., $P^{(a)}$ or $P^{(b)}$, is less sensitive to measurement error than is the response of a single cellular constituent, i.e., a single element of the corresponding unprojected responses $p^{(a)}$ or $p^{(b)}$. Accordingly, the elements of a projected profile will generally show significant up- or down-regulation at lower levels of perturbation than will the individual elements (i.e., the individual cellular constituents) of the corresponding unprojected response.

Further, as is well known to those skilled in the art, averaging makes a tremendous difference, e.g., in the probabilities of detecting actual events rather than false alarms (see, e.g., Van Trees, H. L., 1968, *Detection, Estimation, and Modulation Theory* Vol. 1, Wiley & Sons). Accordingly, the elements of a projected profile generally also give more accurate (i.e., small fractional error) measures of the amplitude of response at any level of perturbation. Specifically, in most embodiments of the invention there are independent measurement error in the data for each cellular constituent, or such independent errors may be reasonably assumed. In such embodiments, the fractional standard error of the q'th projected profile elements (i.e., of $P_q$) is approximately $M_q^{-1/2}$ times the average fractional 5 error of the individual cellular constituents, where $M^q$ is the number of cellular constituents in the q'th cellular constituent sets. Accordingly, if the average measured up or down regulation of an individual cellular constituent is significant at x standard deviations, the projected profile element will be significant at $M^{q1/2}x$ standard deviations.

Finally, because they are derived from observations of co-variance and/or co-regulation, the basis cellular constituents can frequently be directly associated with the biology, e.g., with the biological pathways, of the individual response profile. Thus, the basis cellular constituents function as matched detectors for their individual response components.

5.3.5. Consensus Profiles

The final aspect of the analytical methods of this invention comprises methods of determining the consensus profiles of the invention, and comparing biological response profiles of interest with such consensus profiles.

Determining Consensus Profiles

In preferred embodiments, the consensus profiles $P^{(C)}$ of the invention are defined as the intersection of the sets of cellular constituents activated (or de-activated) by members of a group of experimental conditions (e.g., a group of perturbations). Such intersections may be identified by either qualitative or quantitative methods.

In one embodiment, the intersections of cellular constituent sets are identified by visual inspection of response profile data for a plurality of perturbations. Preferably, such data is re-ordered, according, e.g., to the methods described in Section 5.3.2 and 5.3.3 above so that co-varying cellular constituents, and similar response profiles may be more readily identified. For example, FIG. 3 shows a false color display of a plurality of genetic transcripts (horizontal axis) measured in a plurality of experiment, i.e., response profiles, wherein cells of *S. cerevisiae* are exposed to the variety of different perturbations indicated on the vertical axis. Both the cellular constituents and the response profile have been grouped and re-ordered according to the methods of Section 5.3.2 and 5.3.3 so the co-varying cellular constituents (i.e., genesets) and similar response profiles can be readily visualized.

An exemplary set of eight experiments (i.e., perturbations) shown in FIG. 3, which are involved in immunosuppression conditions, is first considered:

Row 15: addition of 50 µg/ml of the immunosuppressant drug FK506 to wild-type cells;

Row 18: addition of 50 µg/ml of FK506 to a strain missing the CPH1 gene;

Row 28: addition of 1 µg/ml of FK506 to wild-type cells;

Row 29: addition of 50 µg/ml of Cyclosporin A to wild-type cells;

Row 30: addition of 1 µg/ml of FK506 to a strain missing the CPH1 gene;

Row 31: deletion of the Calcineurin genes CNA1 and CNA2;

Row 32: addition of 50 µg/ml of Cyclosporin A to a strain missing the FPR gene; and Row 34: addition of 50 µg/ml of FK506 to a strain missing the GCN4 gene.

In each of the above experimental conditions, it is expected that the primary immunosuppressant effect via the calcineurin protein will be exhibited (see, e.g., Cardenas et al., 1994, *Perspectives in Drug Discovery and Design* 2:103–126; and Marton et al., 1998, *Nature Medicine*, in press). Indeed, as can bed seen by visual inspection of FIG. 3, the common geneset in all of the above-listed perturbations is geneset no. 5 of FIG. 7, which is associated with the calcineurin protein, the primary target of the above-listed immunosuppressant drugs.

Visual inspection of FIG. 3 also reveals that Rows 28–31 not only share the primary effect of the calcineurin protein (i.e., of geneset no. 5), they also have little additional effect from other genesets. Thus, the consensus profile $P^{(C)}$ for the response shown in Rows 28–31 consist of the geneset associated with the calcineurin protein (i.e., geneset no. 5). This consensus profile may be used, e.g., to evaluate drugs or drug candidates which are intended to specifically affect calcineurin protein levels and/or activity.

By contrast, Rows 15, 18, and 34 show appreciable secondary effects from other genesets. In particular, there is a set of experiments, including Rows 12–18 of FIG. 3, which exhibits a large set of up regulated genes associated with the Gcn4 transcription factor (see, Marton et al., supra). Thus, the consensus profile for these rows consists of both the geneset associated with both the calcineurin protein and the geneset co-regulated by the Gcn4 transcription factor.

In other, more formal quantitative embodiments of the invention, the intersections of cellular constituent sets are preferably identified, e.g., by thresholding the individual response amplitudes of the projected response profiles. An exemplary illustration of such thresholding is shown in FIG. 10 for rows 15, 18, 28–32, and 34 of FIG. 3. Thresholds are indicated by the dashed lines in FIG. 10. In particular, thresholds are set at a detection limit equal to two standard errors of the geneset response, assuming uncorrelated errors in the individual genes, or standard error of ~0.15 in the $\log_{10}$, as observed for the dataset illustrated in FIG. 3. With the preferred normalization of the basis vectors (i.e., with $|e^{(q)}|=1$ for all genesets q), the appropriate threshold for the geneset amplitude is the same as that for individual genes at a particular desired confidence level. Although several genesets other than geneset no. 5 occasionally have amplitudes over the indicated threshold, the intersection of the eight sets of amplitudes that exceed the indicated threshold consists of only geneset no. 5; i.e., geneset no. 5 is the only geneset for which the response amplitude exceeds the threshold in every experiment whose thresholds are plotted in FIG. 10. Thus, the consensus profile $P^{(C)}$ for the immunosuppressants in these experiments is geneset no. 5 (i.e., the calcineurin pathway).

In alternative embodiments, intersections of cellular constituent sets may be identified arithmetically, by replacing significant amplitudes of cellular constituent sets in the projected responses (i.e., those amplitudes which are above the threshold) with values of unity, and replacing amplitudes of cellular constituent sets in the projected responses that are below the threshold with values of zero. The intersection may then be determined by the element-wise product of all project profiles. In particular, in such embodiments the consensus profile consists of those cellular constituent sets whose index is unity after the product operation.

Comparing Responses to Consensus Profiles

Once basis cellular constituent sets have been identified, e.g., according to the methods described in Section 5.3.2 above, projected profiles P may be obtained for any biological response profile p comprising the same cellular constituent as those used to define the basis cellular constituent sets, e.g., according to the methods provided in Section 5.3.4 above. As noted supra, similarities and differences between two or more projected profiles, for example between the projected profile $P^{(a)}$ and $P^{(b)}$, may be readily evaluated. In preferred embodiments, projected profiles are compared by an objective, quantitative similarity metric S. In one particularly preferred embodiment, the similarity metric S is the generalized cosine angle between the two projected profiles being compared, e.g., between $P^{(a)}$ and $P^{(b)}$. The generalized cosine angle is a metric well known to those skilled in the art, and may be defined by the equation $$S_{a,b} = S(P^{(a)}, P^{(b)}) = \frac{P^{(a)} \cdot P^{(b)}}{|P^{(a)}||P^{(b)}|} \tag{23}$$

wherein the dot product, $P^{(a)} \cdot P^{(b)}$, is defined by $$P^{(a)} \cdot P^{(b)} = \sum_q (P_q^{(a)} \times P_q^{(b)}) \tag{24}$$

and $|P^{(a)}|=(P^{(a)} \cdot P^{(a)})^{1/2}$, and $|P^{(b)}|=(P^{(b)} \cdot P^{(b)})^{1/2}$.

In such embodiments, projected profile $p^{(a)}$ is most similar to the projected profile $p^{(b)}$ if $S_{a,b}$ is a maximum. In more detail, $S_{a,b}$ may have a value from −1 to +1. A value of $S_{a,b}=+1$ indicates that the two profiles are essentially identical; the same cellular constituent effected in $P^{(a)}$ are proportionally effected in $P^{(b)}$, although the magnitude (i.e., strength) of the two responses may be different. A value of $S_{a,b}=-1$ indicates that the two profiles are essentially opposites. Thus, although the same cellular constituent sets in $P^{(a)}$ are proportionally effected in $P^{(b)}$, those sets which increase (e.g., are up-regulated) in $P^{(a)}$ decrease (e.g., are down regulated) in $P^{(b)}$ and vice-versa. Such profiles are said to be "anti-correlated." Finally, a value of $S_{a,b}=0$ indicates maximum dissimilarity between the two responses; those cellular constituent sets effected in $P^{(a)}$ are not effected in $P^{(b)}$ and vice-versa.

Projected profiles may also be compared to the consensus profiles $P^{(C)}$ of the present invention. Such comparisons are useful, e.g., to determine whether a particular response profile, e.g., of the biological response to a drug or drug candidate, is consistent with or fall short of the consensus profile, e.g., for a class or type of drugs, or for an "ideal" biological response such as one associated with a desired therapeutic effect. Projected profiles may be compared to the consensus profiles of this invention by means of the same methods described supra for comparing projected profiles generally. Thus a given projected profile $P^{(a)}$ may be compared to a consensus profile $P^{(C)}$, e.g., by evaluating a quantitative similarity metric $S_a^{(C)}=S(P^{(a)}, P^{(C)})$, wherein $S(P^{(a)}, P^{(C)})$ is defined, e.g., according to Equation 23 above.

The statistical significance of any observed similarity $S_{a,b}$ may be assessed, e.g., using an empirical probability of distribution generated under the null hypothesis of no correlation. Such a distribution may be generated by performing projection and similarity calculations, e.g., according to the above described methods and equations, for many random permutations of the cellular constituent index i in the original unprojected response profile p. Mathematically, such a permutation may be represented by replacing the ordered set $\{p_i\}$ by $\{p_{\Pi(i)}\}$, where $\Pi(i)$ denotes a permutation of the index i. Preferably, the number of permutations is anywhere from about 100 to about 1000 different random permutations. The probability that the similarity $S_{a,b}$ arises by chance may then be determined from the fraction of the total permutations for which the similarity $S_{a,b}^{(permuted)}$ exceeds the similarity $S_{a,b}$ determined for the original, unpermuted data.

Clustering Projected Profiles

The present invention also provides methods for clustering and/or sorting projected profiles, e.g., by means of the clustering methods described in Section 5.3.2 and 5.3.3 above, according to their similarity as evaluated, e.g., by a quantitative similarity metric S such as the generalized cosine angle. In a preferred embodiment, the clustering of projected profiles is done using the distance metric $$I_{a,b} = 1 - S_{a,b} \quad (25)$$

In a particularly preferred embodiment of this invention, the projected profiles are clustered or ordered according to their similarity to a consensus profile $P^{(C)}$, e.g., using the distance metric $I = 1 - S^{(C)} = 1 - S(P, P^{(C)})$, where P is a projected response profile to be sorted according to the methods of the present invention.

Such clustering and sorting methods are analogous to the clustering of the original, unprojected response profiles described in Section 5.3.3 above. However, the clustering of projected response profiles has the advantages of reduced measurement error effects and enhanced capture of the relevant biology inherent to the projected response profiles.

5.3.6. Implementation Systems and Methods

The analytic methods described in Sections 5.3.1–5.3.5 above are preferably implemented by means of an automated system, such as a computer system. Accordingly, this section describes exemplary computer systems, as well as methods and programs for operating such computer systems, which may be used to perform the methods of this invention.

Figure 11:
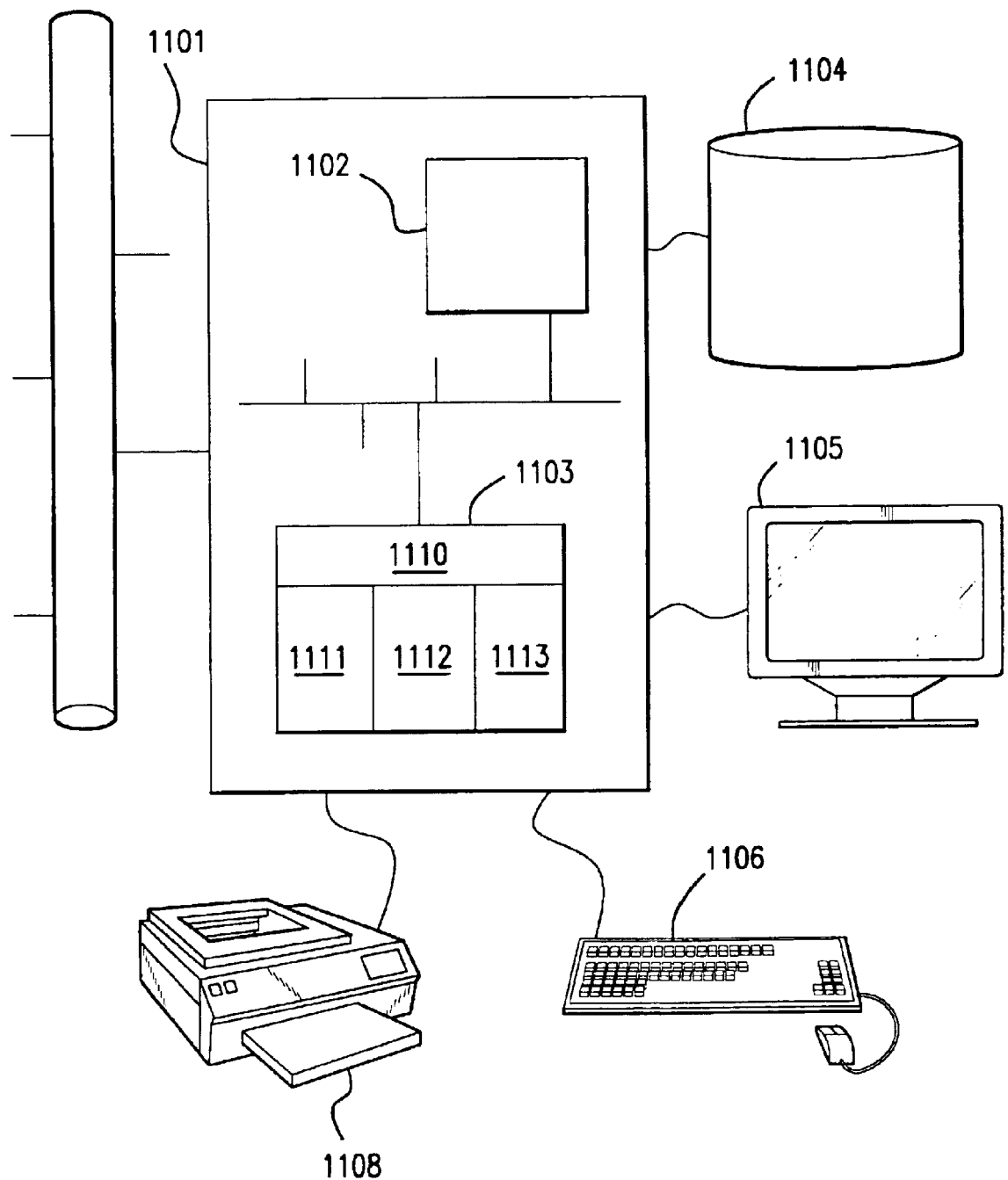
FIG. 11 illustrates an exemplary embodiment of a computer system useful for implementing the methods of this invention.

FIG. 11 illustrates an exemplary computer system suitable for implementing the analytic methods of this invention. Computer system 1101 comprises internal components linked to external components. The internal components of this computer system include a processor element 1102 interconnected with main memory 1103. For example, computer system 1101 can be an Intel Pentium®-based processor of 200 MHz or greater clock rate and with 32 MB or more of main memory.

The external components include mass storage means 1104. This mass storage means can be one or more hard disks (which are typically packaged together with the processor and memory). Such hard disks are typically of 1 GB or greater storage capacity. Other external components may include user interface device 1105, which can be a monitor, together with inputing device 1106, which can be a "mouse," or other graphic input devices (not illustrated) and/or a keyboard. A printing device 1108 can also be attached to the computer system 1101.

Typically, computer system 1101 is also linked to network link 1107, which can be part of an Ethernet link to one or more other local computer systems, to one or more remote computer systems, or to one or more wide area communication networks such as the Internet. The network link allows computer system 1101 to share data and processing tasks with other computer systems.

Loaded into memory during operation of computer system 1101 are several software components which are both standard in the art and special to the instant invention. These software components collectively cause the computer system to function according to the methods of the present invention. These software components are typically stored on mass storage means 1104. For example, software component 1110 represents an operating system which is responsible for managing computer system 1101 and its network interconnections. The operating system 1110 can be, for example, of the Microsoft Windows family, such as Windows 95, Windows98, or WindowsNT.

Software component 1111 represents common language and functions conveniently present on computer system 1101 to assist programs implementing methods specific to this invention. Many high or low level computer languages can be used to program the analytical methods of this invention. Instruction can be interpreted during run-time, or they may be interpreted before run time (i.e., compiled) for later execution. Preferred languages include C, C++, and less preferably JAVA®.

Most preferably, the methods of this invention are programmed in mathematical software packages which allow symbolic entry of equations and high-level specification of processing, including algorithms to be used. Such software packages are preferable since they free a user of the need to procedurally program individual equations or algorithms. Exemplary mathematical software packages which may be used in the computer systems of this invention include Matlab from Mathworks (Natick, Mass.), Mathematica from Wolfram Research (Champaign, Ill.), or S-Plus from Math Soft (Cambridge, Mass.).

Finally, software component 1112 represents the analytical methods of the present invention as programmed, e.g., in a procedural language or symbolic package. In a preferred embodiment, the computer system also contains a database 1113 of perturbation response profiles and/or consensus response profiles.

In certain embodiments software component 1112 includes analytic software 1112a capable of executing the cluster analysis methods of the present invention. Such analytic software is capable, e.g., of causing the processor of the computer system to execute steps of (a) receiving data from one or more perturbation experiments, preferably from a plurality of perturbation experiments; (b) receiving criteria for the selection of cellular constituent sets such as genesets; (c) clustering the perturbation data into a "clustering tree" according to the clustering methods of this invention; and (d) defining cellular constituent sets based upon the clustering tree and the received criteria for selection of cellular constituent sets. The data from perturbation experiments and/or the criteria for selecting cellular constituent sets may be received, e.g., by a user loading such data into the memory. For example, a user may load such data into the memory from monitor 1105 and keyboard 1106, or from other computer systems linked by network connection 1107, or from storage media 1104 including removable storage media such as a CD-ROM or floppy disk (not illustrated).

Preferably, software component 1112 includes analytic software components (1112b) capable of executing the projection methods of the present invention. In particular, analytic software component 1112b preferably comprises components which are capable of determining projected response profiles. Such software an analytic software component preferably causes the processor to execute steps of (a) receiving a definition of cellular constituent sets, such as a geneset definition; (b) receiving one or more expression profiles, and (c) calculating projected profiles based upon the received definition of cellular constituent sets and the received one or more expression profiles.

In a particularly preferred embodiment, the received definition of cellular constituent sets is the definition of cellular constituent sets determined by analytic software component 1112a. In another preferred embodiment, the received definition of cellular constituent sets is obtained from a dynamic database system of cellular constituent sets, such as a dynamic geneset database system. In certain preferred embodiments, the one or more received expression profiles comprise the data from one or more perturbation experiments received by analytical software component 1112a. Thus, in such embodiments, the determined projection response profiles are projected perturbation response profiles. Alternatively, the received definition of cellular constituent sets and/or the received expression profiles may loaded by a user, e.g., by any of the above described means.

In yet another embodiment, software component 1112 includes analytical software 1112c capable of executing the consensus profile determination methods of this invention. In particular, analytical software component 1112c preferably causes the processor component of the computer system to execute steps of (a) receiving data from one or more perturbation experiments, preferably from a plurality of perturbation experiments; (b) receiving a definition of cellular constituent sets, such as a geneset definition; and (c) determining the cellular constituent sets activated (or de-activated) in the received data from one or more perturbation experiments. The received data from one or more perturbation experiments preferably comprise, e.g., data from a particular group of perturbation experiments, such as perturbation of a particular cellular constituent or of a particular biological pathway. The received data from one or more perturbation experiments and/or received definition of cellular constituent sets may be loaded into memory by any of the means discussed above for analytic software components 1112a and 1112b. In certain embodiments, the received data from one or more perturbation experiments are selected from the data from one or more perturbation experiment received by analytical software component(s) 1112a and/or 1112b.

In a final embodiment, software component 1112 also contains analytical Software component 1112d capable of comparing two or more projected response profiles. In particular, analytic software component 1112d preferably causes the processor of the computer system to execute steps of (a) receiving a first projected profile, (b) receiving a second projected profile, and (c) calculating the similarity between the first and second projected profiles. In certain embodiment, either the first or second projected profile received may be a consensus profile. In a preferred embodiment, the received consensus profile is a consensus profile determined, e.g., by analytic software component 1112c. Alternatively, the received consensus profile may be a consensus profile obtained, e.g., from a database of consensus profile wherein each consensus profile of the database is associated with a particular biological response.

Alternative computer systems and software for implementing the analytic methods of this invention will be apparent to one of skill in the art, and are intended to be comprehended within the accompanying claims. In particular, the accompanying claims are intended to include alternative program structures for implementing the methods of the present invention that will be readily apparent to one skilled in the art.

5.4. Measurement Methods

Drug responses are obtained for use in the instant invention by measuring the cellular constituents changed by drug exposure or by pathway perturbation. These cellular characteristics can be of any aspect of the biological state of a cell. They can be, e.g., of the transcription state, in which RNA abundances are measured, the translation state, in which protein abundances are measured, the activity state, in which protein activities are measured. The cellular characteristics can also be of mixed aspects, for example, in which the activities of one or more proteins originating a particular biological pathway are measured along with RNA abundances (gene expression) of cellular constituents in the pathway downstream of the originating protein(s). This section describes exemplary methods for measuring the cellular constituents in drug or pathway responses. This invention is adaptable to other methods of such measurement.

Embodiments of this invention based on measuring the transcriptional state of drug and pathway responses are preferred. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates). Such measurement methods are described in Section 5.4.2.

In various alternative embodiments of the present invention, aspects of the biological state other than the transcriptional state, such as the translational state, the activity state, or mixed aspects can be measured. Details of these embodiments are described in this section. Such measurement methods are described in Section 5.4.3.

5.4.1. Measurement of Drug Response Data

To measure drug response data, cell are exposed to graded levels of the drug or drug candidate of interest. When the cells are grown in vitro, the compound is usually added to their nutrient medium. In the case of yeast, such as *S. cerevisiae*, it is preferably to harvest the cells in early log phase, since expression patterns are relatively insensitive to time of harvest at that time. The drug is added in a graded amount that depends on the particular characteristics of the drug, but usually will be between about 1 ng/ml and 100 mg/ml. In some cases a drug will be solubilized in a solvent such as DMSO.

The biological state of cells exposed to the drug and cells not exposed to the drug is measured according to any of the below described methods. Preferably, transcript or microarrays are used to find the mRNAs with altered expression due to exposure to the drug. However, other aspects of the biological state may also be measured to determine, e.g., proteins with altered translation or activities due to exposure to the drug.

It is preferable for measurements of drug responses, in the case of two-colored differential hybridization described below, to measure also with reversed labeling. Also, it is preferable that the levels of drug exposure used provide sufficient resolution of rapidly changing regions of the drug response, e.g., by using approximately ten levels of drug exposure.

5.4.2. Transcriptional State Measurement

In general, measurement of the transcriptional state can be performed using any probe or probes which comprise a polynucleotide sequence and which are immobilized to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probe may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro, (e.g., by PCR), or non-enzymatically in vitro.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory, Manual,* 2nd ed., Vols. 1–3, Cold Spring Harbor Laboratory, Cold Spring Harbor, N.Y.). Alternatively, the solid support or surface may be a glass or plastic surface.

5.4.2.1. Microarrays Generally

In a particularly preferred embodiment, measurement of the transcriptional state are made by hybridization to microarrays of probes consisting of a solid phase, on the surface of which are immobilized a population of polynucleotides, such as a population of DNA or DNA mimics, or, alternatively, a population of RNA. Specifically, a microarray is an array of less than 6.25 cm$^2$ in size. Microarrays can be employed, e.g., for analyzing the transcriptional state of a cell, such as the transcriptional states of cells exposed to graded levels of a drug of interest.

In preferred embodiments, a microarray comprises a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably, the microarrays are small, usually smaller than 5 cm$^2$, and they are made from materials that are stable under binding (e.g., nucleic acid hybridization) conditions. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence. The position of each probe on the solid surface is preferably known. In one embodiment, the microarray is a high density array, preferably having a density greater than about 60 different probes per 1 cm$^2$. In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to about 75%, more often to at least about 85%, even more often to about 90%, and still more often to at least about 99%. Preferably, the microarray has binding sites for genes relevant to the action of a drug of interest or in a biological pathway of interest. A "gene" is identified as an open reading frame ("ORF") which encodes a sequence of preferably at least 50, 75, or 99 amino acids from which a messenger RNA is transcribed in the organism or in some cell in a multicellular organism. The number of genes in a genome can be estimated from the number of mRNAs expressed by the organism, or by extrapolation from a well characterized portion of the genome. When the genome of the organism of interest has been sequenced, the number of ORF's can be determined and mRNA coding regions identified by analysis of the DNA sequence. For example, the genome of *Saccharomyces cerevisiae* has been completely sequenced, and is reported to have approximately 6275 ORFs longer than 99 amino acids. Analysis of the ORFs indicates that there are 5885 ORFs that are likely to encode protein products (Goffeau et al., 1996, *Science* 274:546–567). In contrast, the human genome is estimated to contain approximately 10$^5$ genes.

5.4.2.2. Preparing Probes for Microarrays

As noted above, the "probe" to which a particular polynucleotide molecule specifically hybridizes according to the invention is usually a complementary polynucleotide sequence. In one embodiment, the probes of the microarray are DNA or DNA "mimics" (e.g., derivatives and analogues) corresponding to at least a portion of each gene in an organism's genome. In another embodiment, the probes of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtain, e.g., by polymerase chain reaction ("PCR") amplicafication of gene segments from genomic DNA, cDNA (e.g., by RT-PCR), or clones sequences. PCR primers are preferably chosen based on known sequences of the genes or cDNA that result in amplification of unique fragments (i.e.g, fragments that do not share more than 10 bases of contiguous identical sequence with any other fragment on the microarray). Computer programs that are well known in the art are useful in the design of primer with the required specificity and optimal amplification properties, such as Oligo version 5.0 (National Biosciences). Typically, each probe of the microarray will be between about 20 bases and about 12,000 bases, and usually between about 300 bases and about 2,000 bases in length, and still more usually between about 300 bases and about 800 bases in length. PCR methods are well known in the art, and are described, for example, in Innis et al., eds., 1990, *PCR Protocols: A Guide to Methods aid Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBrid et al., 1983, *Tetrahedron Lett.* 24:246–248). Synthetic sequences are typically between about 15 and about 500 bases in length, more typically between about 20 and about 50 bases. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.4.2.3. Attaching Probes to the Solid Surface

The probes are attached to a solid support or surface, which may be made, e.g., from glass, plastic (e.g., polypropylene, nylon), polyacrylamide, nitrocellulose, or other materials. A preferred method for attaching the nucleic acids to a surface is by printing on glass plates, as is described generally by Schena et al., 1995, *Science* 270:467–470. This method is especially useful for preparing microarrays of cDNA (See also, DeRisi et al., 1996, *Nature Genetics* 14:457–460; Shalon et al., 1996, *Genome Res.* 6:689–645; and Schena et al., 1995, *Proc. Natl. Acad. Sci. U.S.A.* 93:10539–11286). Blanchard discloses the use of an ink jet printer for oligonucleotide synthesis (U.S. application Ser. No. 09/008,120, filed Jan. 16, 1998).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Please et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 20-mers) of known sequence are synthesized directly on a surface such as a derivatized glass slides. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.* 20:1679–1684), may also be used. In principle, any type of array, for example, dot blots on a nylon hybridization membrane (see Sambrook et al., supra) could be used. However, as will be recognized by those skilled in the art, very small arrays will frequently be preferred because hybridization volumes will be smaller.

5.4.2.4. Target Polynucleotide Molecules

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A) messenger RNA (mRNA), fractions thereof, or RNA transcribed from cDNA. Methods for preparing total and poly(A)$^-$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). Poly (A)$^-$ RNA is selected by selection with oligo-dT cellulose. Cells of interest include, but are by no means limited to, wild-type cells, drug-exposed wild-type cells, modified cells, diseased cells, and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.4.2.5. Hybridization to Microarrays

Nucleic acid hybridization and wash conditions are chosen so that the polynucleotide molecules to be analyzed by the invention "specifically bind" or "specifically hybridize" to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA or DNA) of probe and target nucleic acids. General parameters for specific (i.e., stringent) hybridization conditions are described in Sambrook et al. (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in high stringency wash buffer (0.1×SSC plus 0.2% SDS) (Shena et al., 1996, *Proc. Natl. Acad. Sci. U.S.A.* 93:10614). Useful hybridization conditions are also provided, e.g., Tijessen, 1993, *Hybridization With Nucleic Acid Probes*, Elsevier Science Publishers B. V.; and Kricka, 1992, *Nonisotopic DNA Probe Techniques*, Academic Press, San Diego, Calif.

5.4.2.6. Signal Detection and Data Analysis

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when delectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, *Science* 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

When fluorescently labeled probes are used, the fluorescence emissions at each site of a transcript array can be, preferably, detected by scanning confocal laser microscopy.

In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

5.4.2.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad.*

Sci. U.S.A. 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487).

Such methods and systems of measuring transcriptional state, although less preferable than microarrays, may, nevertheless, be used in the present invention.

5.4.3. Measurements of Other Aspects of Biological State

Although monitoring cellular constituents other than mRNA abundances currently presents certain technical difficulties not encountered in monitoring mRNAs (i.e., the transcriptional state), it will be apparent to those skilled in the art that the use of methods of this invention are applicable to any cellular constituent that can be monitored.

In various embodiments of the present invention, aspects of the biological state other than the transcriptional state, such as the translational state, the activity state, or mixed aspects thereof can be measured in order to obtain drug responses for the present invention. Details of these embodiments are described in this section.

5.4.3.1. Translational State Measurements

Measurements of the translational state may be performed according to several methods. For example, whole genome monitoring of protein (i.e., the "proteome," Goffea et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y.). In a preferred embodiment, monoclonal antibodies are raised against synthetic peptide fragments designed based on genomic sequence of the cell. With such an antibody array, proteins from the cell are contacted to the array, and their binding is assayed with assays known in the art.

Alternatively, proteins can be separated by two-dimensional gel electrophoresis systems. Two-dimensional gel electrophoresis is well known in the art, and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. U.S.A.* 93:1440–1445; Sagliocco et al., 1996, *Yeast* 2:1519–1533; and Lander, 1996, *Science* 274:536–539. The resulting electropherograms can be analyzed by numerous techniques, including mass spectrometric techniques, western blotting, and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.4.3.2. Activity State Measurements

Where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known or measured, the changes in protein activities form the response data analyzed by the foregoing methods of this invention.

5.4.3.3. Mixed Aspects of Biological State

In alternative and non-limiting embodiments, response data may be formed of mixed aspects of the biological state of a cell. Response data can be constructed from combinations of, e.g., changes in certain mRNA abundances, changes in certain protein abundances, and changes in certain protein activities.

5.5. Targeted Perturbation Methods

Methods for targeted perturbation of biological pathways at various levels of a cell are increasingly widely known and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, and so forth) can be employed in performing pathway perturbations. Controllable modifications of cellular constituents consequentially controllably perturb pathways originating at the modified cellular constituents. Such pathways originating at specific cellular constituents are preferably employed to represent drug action in this invention. Preferable modification methods are capable of individually targeting each of a plurality of cellular constituents and most preferably a substantial fraction of such cellular constituents.

The following methods are exemplary of those that can be used to modify cellular constituents and thereby to produce pathway perturbations which generate the pathway responses used in the steps of the methods of this invention as previously described. This invention is adaptable to other methods for making controllable perturbations to pathways, and especially to cellular constituents from which pathways originate.

Pathway perturbations are preferably made in cells of cell types derived from any organism for which genomic or expressed sequence information is available and for which methods are available that permit controllably modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of yeast genes. A preferred strain of yeast is a *S. cerevisiae* strain for which yeast genomic sequence is known, such as strain S288C or substantially isogeneic derivatives of it (see, e.g., Dujon et al., 1994, *Nature* 369:371–378; Bussey et al., 1995, *Proc. Natl. Acad. Sci. U.S.A.* 92:3809–3813; Feldmann et al., 1994, *E.M.B.O.J.* 13:5795–5809; Johnston et al., 1994, *Science* 265:2077–2082; Galibert et al., 1996, *E.M.B.O.J.* 15:2031–2049). However, other strains may be used as well. Yeast strains are available, e.g., from American Type Culture Collection, 10801 University Boulevard, Manassas, Va. 20110–2209. Standard techniques for manipulating yeast are described in C. Kaiser, S. Michaelis, & A. Mitchell, 1994, *Methods in Yeast Generics: A Cold Spring Harbor Laboratory Course Manual*, Cold Spring Harbor Laboratory Press, New York; and Sherman et al., 1986, *Methods in Yeast Genetics: A Laboratory Manual*, Cold Spring Harbor Laboratory, Cold Spring Harbor. N.Y.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

5.5.1. Titratable Expression Systems

Any of the several known titratable, or equivalently controllable, expression systems available for use in the budding yeast *Saccharomyces cerevisiae* are adaptable to this invention (Mumberg et al., 1994, *Nucl. Acids Res.* 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, *Mol Cell. Biol.* 8:1440–1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, *Nucl. Acids. Res.* 14:7861–7871), which is induced by the absence of methionine in the growth medium, and the CUP1 promoter, which is induced by copper (Mascorro-Gallardo et al., 1996, *Gene* 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, *Yeast* 13:837–848). The Tet promoter, adopted from mammalian expression systems (Gossen et al., 1995, *Proc. Nat. Acad. Sci. USA* 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, *Yeast* 13:837–848).

In mammalian cells, several means of titrating expression of genes are available (Spencer, 1996, *Trends Genet.* 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, *Proc. Natl. Acad. Sci. USA* 89:5547–5551; Hoffmann et al., 1997, *Nucl. Acids. Res.* 25:1078–1079; Hofmann et al., 1996, *Proc. Natl. Acad. Sci. USA* 83:5185–5190; Paulus et al., 1996, *Journal of Virology* 70:62–67). Another commonly used controllable promoter system in mammalian cells is the ecdysone-inducible system developed by Evans and colleagues (No et al., 1996, *Proc. Nat. Acad. Sci. USA* 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, *Proc. Nat. Acad. Sci. USA* 93:4604–4607; Spencer, 1996, *Trends Genet.* 12:181–187) and similar systems in yeast. In this system, the gene of interest is put under the control of the CID-responsive promoter, and transfected into cells expressing two different hybrid proteins, one comprised of a DNA-binding domain fused to FKBP 12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, *Development* 122:4149–4157; Spradling et al., 1995, *Proc. Natl. Acad. Sci. USA.* 92:10824–10830; Ramirez-Solis et al., 1993, *Methods Enzymol.* 225:855–878; and Thomas et al., 1987, *Cell* 51:503–512.

5.5.2. Transfection Systems for Mammalian Cells

Transfection or viral transduction of target genes can introduce controllable perturbations in biological pathways in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1 +/− system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation pathway (Anderson et al., 1994, *Adv. Immunol.* 56:171–178). Inhibitors of this enzyme are of interest as potential immunosuppressive drugs (Hanke J H, 1996, *J. Biol Chem* 271(2):695–701). A specific mutant of the Jurkat T cell line (JcaM1) is available that does not express Ick kinase (Straus et al., 1992, *Cell* 70:585–593). Therefore, introduction of the Ick gene into JCaM 1 by transfection or transduction permits specific perturbation of pathways of T cell activation regulated by the Ick kinase. The efficiency of transfection or transduction, and thus the level of perturbation, is dose related. The method is generally useful for providing perturbations of gene expression or protein abundances in cells not normally expressing the genes to be perturbed.

5.5.3. Methods of Modifying RNA Abundances or Activities

Methods of modifying RNA abundances and activities currently fall within three classes, ribozymes, antisense species, and RNA aptamers (Good et al., 1997, *Gene Therapy* 4: 45–54). Controllable application or exposure of a cell to these entities permits controllable perturbation of RNA abundances.

Ribozymes are RNAs which are capable of catalyzing RNA cleavage reactions. (Cech, 1987, *Science* 236:1532–1539; PCT International Publication WO 90/11364, published Oct. 4, 1990; Sarver et al., 1990, *Science* 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, *Nature* 334:585–591; Koizumi et al., 1988, *FEBS Lett.* 228:228–230; Koizumi et al., 1988, *FEBS Lett.* 239:285–288). Ribozyme methods involve exposing a cell to, inducing expression in a cell, etc. of such small RNA ribozyme molecules. (Grassi and Marini, 1996, *Annals of Medicine* 28: 499–510; Gibson, 1996, *Cancer and Metastasis Reviews* 15: 287–299).

Ribozymes can be routinely expressed in vivo in sufficient number to be catalytically effective in cleaving mRNA, and thereby modifying mRNA abundances in a cell. (Cotten et al., 1989, *EMBO J.* 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1 989, *Proc. Natl. Acad. Sci. U.S.A.* 86: 6553–6556; Lemaitre et al., 1987, *Proc. Natl. Acad. Sci. U.S.A.* 84: 648–652; PCT Publication No. WO 88/09810, published Dec. 15, 1988), hybridization-triggered cleavage agents (see, e.g., Krol et al., 1988, *BioTechniques* 6: 958–976) or intercalating agents (see, e.g., Zon, 1988, *Pharm. Res.* 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, $Nucl.$ $Acids$ $Res.$ 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, $Nucl. Acids Res.$ 16: 3209), methylphosphonate oligonucleotides can be prepared by use of controlled pore glass polymer supports (Sarin et al., 1988, $Proc. Natl. Acad. Sci. U.S.A.$ 85: 7448–7451), etc. In another embodiment, the oligonucleotide is a 2'-O-methylribonucleotide (Inoue et al., 1987, $Nucl. Acids Res.$ 15: 6131–6148), or a chimeric RNA-DNA analog (Inoue et al., 1987, $FEBS Lett.$ 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, $Nature$ 290: 304–310), the promoter contained in the 3' long terminal repeat of Rous sarcoma virus (Yamamoto et al., 1980, $Cell$ 22: 787–797), the herpes thymidine kinase promoter (Wagner et al., 1981, $Proc. Natl. Acad. Sci. U.S.A.$ 78: 1441–1445), the regulatory sequences of the metallothionein gene (Brinster et al., 1982, $Nature$ 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, $Gene Therapy$ 4: 45–54) that can specifically inhibit their translation.

5.5.4. Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et al., 1994, $Science$ 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, $Molecular Biology of the Cell$, Chpt. 8, New York: W. H. Freeman and Co.) with a gene coding for the fusion protein Ub-Arg-DHFR$^{ts}$ -P ("Ub" stands for ubiquitin). The N-terminal ubiquitin is rapidly cleaved after translation exposing the N-terminal degron. At lower temperatures, lysines internal to Arg-DHFRLS are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, *Immunology Today* 9:84–86) or transforming hybridoma mRNA encoding a desired antibody into a cell (Burke et al., 1984, *Cell* 36:847–858). In a further technique, recombinant antibodies can be engineered and ectopically expressed in a wide variety of non-lymphoid cell types to bind to target proteins as well as to block target protein activities (Biocca et al., 1995, *Trends in Cell Biology* 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, *Current Opinion in Immunology* 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering*, vol. 2, Borrebaeck ed., IRL Press, pp 295–361). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum. For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, *Immunology Today* 4: 72), and the EBV hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.* 80: 2026–2030), or by transforming human B cells with EBV virus in vitro (Cole et al., 1985, in *Monoclonal Antibodies and Cancer Therapy*, Alan R. Liss, Inc., pp. 77–96). In fact, according to the invention, techniques developed for the production of "chimeric antibodies" (Morrison et al., 1984, *Proc. Natl. Acad. Sci. U.S.A.* 81: 6851–6855; Neuberger et al., 1984, *Nature* 312:604–608; Takeda et al., 1985, *Nature* 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, *J. Biol. Chem.* 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, *EMBO J.* 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946, 778) can be adapted to produce single chain antibodies specific to the target protein. An additional embodiment of the invention utilizes the techniques described for the construction of Fab expression libraries (Huse et al., 1989, *Science* 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the F(ab')$_2$ fragment which can be produced by pepsin digestion of the antibody molecule; the Fab' fragments that can be generated by reducing the disulfide bridges of the F(ab')$_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.5.5. Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, *Nature* 329:219–222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, *Current Opinion in Immunology* 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, *EMBO J.* 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

5.5.6. Drugs of Specific Known Action

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of pathways originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several pathways originating at the target proteins.

6. References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of determining a consensus profile for a first plurality of drug perturbations to a cell type or organism, said method comprising determining, for each of a plurality of sets of cellular constituents in a plurality of response profiles, whether said set of cellular constituents is upregulated or downregulate by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organism, wherein each set of cellular constituents in said plurality of sets of cellular constituents consists of cellular constituents that co-vary in the plurality of response profiles, wherein the cellular constituents which co-vary are identified by cluster analysis of cellular constituents in the plurality of response profiles, wherein the cluster analysis is done by means of the clustering algorithm hclust, wherein said plurality of response profiles comprises at least five response profiles, and wherein said consensus profile for said first plurality of drug perturbations consists of measurements of said set or sets of cellular constituents that are determined in said determining step to be upregulated or downregulate by each of said first plurality of drug perturbations.

2. A method of determining a consensus profile for a first plurality of drug perturbations to a cell type or organism, said method comprising determining, for each of a plurality of sets of cellular constituents in a plurality of response profiles, whether said set of cellular constituents is upregulated or downregulated by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organism, wherein each set of cellular constituents in said plurality of sets of cellular constituents consists of cellular constituents that co-vary in the plurality of response profiles, wherein the cellular constituents which co-vary are identified by cluster analysis of cellular constituents in the plurality of response profiles, wherein said plurality of response profiles comprises at least five response profiles, wherein said cluster analysis is carried out by a hierarchical clustering method, wherein said consensus profile for said first plurality of drug perturbations consists of measurements of said set or sets of cellular constituents that are determined in said determining step to be upregulated or downregulated by each of said first plurality of drug perturbations, wherein a statistical significance for the sets of co-varying cellular constituents is determined by means of an objective statistical test, and wherein the objective statistical test comprises:

(a) determining for each cluster which is generated by said cluster analysis and defines a set of co-varying cellular constituents an actual fractional improvement in the cluster analysis of the cellular constituents based on the unpermuted responses of said cellular constituents, wherein said fractional improvement is an improvement in total scatter with respect to the center of said cluster as compared to total scatter with respect to the respective centers of the two clusters branching out of said cluster;

(b) generating permuted responses of cellular constituents by means of Monte Carlo randomization of perturbation index for the response of each cellular constituent across all perturbations;

(c) performing said cluster analysis on the permuted responses of cellular constituents;

(d) determining for each cluster which is generated in step (c) and defines a set of co-varying cellular constituents the fractional improvement in the cluster analysis of cellular constituents based on the permuted responses of cellular constituents, wherein said fractional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the cellular constituents is obtained for each said cluster which is generated by said cluster analysis and defines a set of co-varying cellular constituents;

wherein the statistical significance of each of said sets of co-varying cellular constituents is determined by comparing the actual fractional improvement for the cluster defining said set to the distribution of fractional improvements for the cluster defining said set.

3. A method of determining a consensus profile for a first plurality of drug perturbations to a cell type or organism, said method comprising determining, for each of a plurality of sets of cellular constituents in a plurality of response profiles, whether said set of cellular constituents is upregulated or downregulated by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organisms, wherein each set of cellular constituents in said plurality of sets of cellular constituents consists of cellular constituents that co-vary under a second plurality of perturbations or that are co-regulated, wherein said plurality of response profiles comprises at least five response profiles, and wherein said consensus profile for said first plurality of drug perturbations consists of measurements of said set or sets of cellular constituents that are determined in said determining step to be upregulated or downregulated by each of said first plurality of drug perturbations;

wherein the one or more sets of cellular constituents are identified by re-ordering the response profiles into sets associated with similar biological effects, wherein the sets of response profiles associated with similar biological effects are identified by cluster analysis of the response profiles done by means of the clustering algorithm hclust.

4. A method of determining a consensus profile for a first plurality of drug perturbations to a cell type or organism, said method comprising determining, for each of a plurality of sets of cellular constituents in a plurality of response profiles, whether said set of cellular constituents is unregulated or downregulate by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organism, wherein each set of cellular constituents in said plurality of sets of cellular constituents consists of cellular constituents that co-vary under a second plurality of perturbations or that are co-regulated, wherein said plurality of response profiles comprises at least five response profiles, and wherein said consensus profile for said first plurality of drug perturbations consists of measurements of said set or sets of cellular constituents that are determined in said determining step to be upregulated or downregulated by each of said first plurality of drug perturbations, wherein the one or more sets of cellular constituents are identified by re-ordering the response profiles into sets associated with similar biological effects, wherein the sets of response profiles associated with similar biological effects are identified by cluster analysis of the response profiles, wherein said cluster analysis is carried out by a hierarchical clustering method, wherein a statistical significance for the sets of response profiles is determined by means of an objective statistical test, and wherein the objective statistical test comprises:

(a) determining for each cluster which is generated by said cluster analysis and defines a set of response profiles an actual fractional improvement in the cluster analysis of the unpermuted response profiles, wherein said fractional improvement is an improvement in total scatter with respect to the center of said cluster as compared to total scatter with respect to the respective centers of the two clusters branching out of said cluster;

(b) generating permuted response profiles by means of Monte Carlo randomization of cellular constituent index for each response profile across the measured cellular constituents;

(c) performing said cluster analysis on the permuted response profiles;

(d) determining for each cluster which is generated in step (c) and defines a set of response profiles the fractional improvement in the cluster analysis of the permuted response profiles, wherein said factional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the response profiles is obtained for each said cluster which is generated by said cluster analysis and defines a set of response profiles;

wherein the statistical significance of each of said sets of response profiles is determined by comparing the actual fractional improvement for the cluster defining said set to the distribution of fractional improvements for the cluster defining said set.

5. A method for grouping measured response profiles in sets which are associated with similar biological effects comprising grouping response profiles among a plurality of response profiles into sets, each of said sets of response profiles consisting of response profiles in which the responses of one or more sets of genes in each response profile are similar among response profiles in the set, each response profile in said plurality of response profiles (i) comprising measurements of transcript levels of a plurality of genes, and (ii) resulting from a different perturbation, wherein each of said sets of genes consists of genes that co-vary under a plurality of perturbations or that are co-regulated, wherein said plurality of response profiles comprises at least five response profiles, wherein the sets of response profiles are identified by cluster analysis of the response profiles done by means of the clustering algorithm hclust.

6. A method for grouping measured response profiles in sets which are associated with similar biological effects comprising grouping response profiles among a plurality of response profile into sets, each of said sets of response profiles consisting of response profiles in which the responses of one or more sets of genes in each response profile are similar among response profiles in the set, each response profile in said plurality of response profiles (i) comprising measurements of transcript levels of a plurality of genes, and (ii) resulting from a different perturbation, wherein each of said sets of genes consists of genes that co-vary under a plurality of perturbations or that are co-regulated, wherein said plurality of response profiles comprises at least five response profiles, wherein the sets of response profiles are identified by cluster analysis of the response profiles, wherein said cluster analysis is carried out by a hierarchical clustering method, wherein a statistical significance for the sets of response profiles is determined by means of an objective statistical test, and wherein the objective statistical test comprises:

(a) determining for each cluster which is generated by said cluster analysis and defines a set of response profiles an actual fractional improvement in the cluster analysis of the unpermuted response profiles, wherein said fractional improvement is an improvement in total scatter with respect to the center of said cluster as compared to total scatter with respect to the respective centers of the two clusters branching out of said cluster, (b) generating permuted response profiles by means of Monte Carlo randomization of gene index for each response profile across the measured genes;

(c) performing said cluster analysis on the permuted response profiles;

(d) determining for each cluster which is generated in step (c) and defines a set of response profiles the fractional improvement in the cluster analysis of the permuted response profiles, wherein said fractional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the response profiles is obtained for each cluster which is generated by said cluster analysis and defines a set of response profiles;

wherein the statistical significance of each of said sets of response profiles is determined by comparing the actual fractional improvement for the cluster defining said set to the distribution of fractional improvements for the cluster defining said set.

7. A method for determining the therapeutic efficacy of a drug or drug candidate comprising identifying one or more groups of sets of cellular constituents in one or more response profiles associated with exposure to the drug or drug candidate, each response profile comprising measurements of a plurality of cellular constituents, wherein each of said groups is indicative of a particular therapeutic effect, and wherein the therapeutic effect of the drug or drug candidate is determined to be the particular therapeutic effect indicated by the identified groups, wherein each of said sets of cellular constituents consists of cellular constituents that co-vary under a plurality of perturbations or that are co-regulated, wherein the sets of cellular constituents are determined by a method comprising performing cluster analysis of the response profiles done by means of the clustering algorithm hclust.

8. A method for determining the therapeutic efficacy of a drug or drug candidate comprising identifying one or more groups of sets of cellular constituents in one or more response profiles associated with exposure to the drug or drug candidate, each response profile comprising measurements of a plurality of cellular constituents, wherein each of said groups is indicative of a particular therapeutic effect, and wherein the therapeutic effect of the drug or drug candidate is determined to be the particular therapeutic effect indicated by the identified groups, wherein each of said sets of cellular constituents consists of cellular constituents that co-vary under a plurality of perturbations or that are co-regulated, wherein the sets of cellular constituents are determined by a method comprising performing cluster analysis of the response profiles, wherein said cluster analysis is carried out by a hierarchical clustering method, wherein a statistical significance for the sets of cellular constituents is determined by means of an objective statistical test, and wherein the objective statistical test comprises:

(a) determining for each cluster which is generated by said cluster analysis and defines a set of cellular constituents an actual fractional improvement in the cluster analysis of cellular constituents based on the unpermuted responses of said cellular constituents, wherein said fractional improvement is an improvement in total scatter with respect to the center of said cluster as compared to total scatter with respect to the respective centers of the two clusters branching out of said cluster;

(b) generating permuted responses of cellular constituents by means of Monte Carlo randomization of the perturbation index for each cellular constituent across all perturbations;

(c) performing said cluster analysis on the permuted responses of cellular constituents;

(d) determining for each cluster which is generated in step (c) and defines a set of cellular constituents the fractional improvement in the cluster analysis of cellular constituents based on the permuted responses of cellular constituents, wherein said fractional improvement is an improvement in total scatter with respect to the center of said cluster as compared to total scatter with respect to the respective centers of the two clusters branching out of said cluster, and (e) repeating steps (b) through (d) so that a distribution of fractional improvements in the cluster analysis of the cellular constituents is obtained for each cluster which is generated by said cluster analysis and defines a set of cellular constituents;

wherein the statistical significance of each of said sets of cellular constituents is determined by comparing the actual fractional improvement for the cluster defining said set to the distribution of fractional improvements for the cluster defining said set.

9. A method of determining a consensus profile for a first plurality of drug perturbations to a cell type or organism, said method comprising determining, for each of a plurality of sets of cellular constituents in a plurality of response profiles, whether said set of cellular constituents is unregulated or downregulated by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organism, wherein each set of cellular constituents in said plurality of sets of cellular constituents consists of cellular constituents that co-vary under a second plurality of perturbations or that are co-regulated, wherein said plurality of response profiles comprises at least five response profiles, and wherein said consensus profile for said first plurality of drug perturbations consists of measurements of said set or sets of cellular constituents that are determined in said determining step to be upregulated or downregulated by each of said first plurality of drug perturbations, wherein said sets of cellular constituents are co-varying cellular constituent sets that are identified by cluster analysis done by means of the clustering algorithm hclust.

10. A method of determining a consensus profile for a first plurality of drug perturbations to a cell type or organism, said method comprising determining, for each of a plurality of sets of cellular constituents in a plurality of response profiles, whether said set of cellular constituents is unregulated or downregulated by each of said first plurality of drug perturbations, each response profile in said plurality of response profiles (i) comprising measurements of a plurality of cellular constituents, and (ii) resulting from a different drug perturbation among said first plurality of drug perturbations to said type of cell or organism, wherein each set of cellular constituents in said plurality of sets of cellular constituents consists of cellular constituents that co-vary under a second plurality of perturbations or that are co-regulated, wherein said plurality of response profiles comprises at least five response profiles, and wherein said consensus profile for said first plurality of drug perturbations consists of measurements of said set or sets of cellular constituents that are determined in said determining step to be unregulated or downregulated by each of said first plurality of drug perturbations, wherein said sets of cellular constituents are co-varying cellular constituent sets that are identified by cluster analysis, wherein said cluster analysis is carried out by a hierarchical clustering method, wherein a statistical significance for the sets of co-varying cellular constituents is determined by means of an objective statistical test, and wherein the objective statistical test comprises:

(a) determining for each cluster which is generated by said cluster analysis and defines a set of co-varying cellular constituents an actual fractional improvement in the cluster analysis of the cellular constituents based on the unpermuted responses of said cellular constituents, wherein said fractional improvement is an improvement in total scatter with respect to the center of said cluster as compared to total scatter with respect to the respective centers of the two clusters branching out of said cluster;

(b) generating permuted responses of cellular constituents by means of Monte Carlo randomization of the perturbation index for response of each cellular constituent across the set of perturbations;

(c) performing said cluster analysis on the permuted responses of cellular constituents;

(d) determining for each cluster which is generated in step (c) and defines a set of co-varying cellular constituents the fractional improvement in the cluster analysis of cellular constituents based on the permuted response responses of cellular constituents, wherein said fractional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the cellular constituents is obtained for each cluster which is generated by said cluster analysis and defines a set of co-varying cellular constituents, wherein the statistical significance of each of said sets of co-varying cellular constituents is determined by comparing the actual fractional improvement for the cluster defining said set to the distribution of fractional improvements for the cluster defining said set.

11. A method for grouping measured response profiles in sets which are associated with similar biological effects comprising grouping response profiles in sets among a plurality of response profiles by cluster analysis of said plurality of response profiles, said sets of response profiles consisting of response profiles having similar responses of a group of cellular constituents, each response profile in said plurality of response profiles (i) comprising measurements of a plurality of cellular constituents, and (ii) resulting from a different perturbation, wherein a statistical significance for the sets of response profiles is determined by means of an objective statistical test, wherein said cluster analysis is carried out by a hierarchical clustering method, and wherein the objective statistical test comprises:

(a) determining for each cluster which is generated by said cluster analysis and defines a set of response profiles an actual fractional improvement in the cluster analysis of the unpermuted response profiles, wherein said fractional improvement is an improvement in total scatter with respect to the center of said cluster as compared to total scatter with respect to the respective centers of the two clusters branching out of said cluster;

(b) generating permuted response profiles by means of Monte Carlo randomization of cellular constituent index for each response profile across the measured cellular constituents;

(c) performing said cluster analysis on the permuted response profiles;

(d) determining for each cluster which is generated in step (c) and defines a set of response profiles the fractional improvement in the cluster analysis of the permuted response profiles, wherein said fractional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the response profiles is obtained for each cluster which is generated by said cluster analysis and defines a set of response profiles;

wherein the statistical significance of each of said sets of response profiles is determined by comparing the actual fractional improvement for the cluster defining said set to the distribution of fractional improvements for the cluster defining said set.

12. A method of determining a consensus profile for a first plurality of perturbations to a cell type or organism, said method comprising determining, for each of a plurality of sets of genes in a plurality of response profiles, whether said set of genes is upregulated or downregulated by each of said first plurality of perturbations, each response profile in said plurality of response profiles (i) comprising measurements of transcript levels for a plurality of genes, and (ii) resulting from a different perturbation among said first plurality of perturbations to said type of cell or organism, wherein each set of genes in said plurality of sets of genes consists of genes having transcripts that co-vary under a second plurality of perturbations or that are co-regulated, and wherein said consensus profile for said first plurality of perturbations consists of measurements of transcript levels for said set or sets of genes that are determined in said determining step to be upregulated or downregulated by each of said first plurality of perturbations, wherein each of the sets of genes consists of genes which co-vary in the plurality of response profiles, wherein the genes which co-vary are identified by cluster analysis of genes in the plurality of response profiles, and wherein the cluster analysis is done by means of the clustering algorithm hclust.

13. A method of determining a consensus profile for a firs plurality of perturbations to a cell type or organism, said method comprising determining, for each of a plurality of sets of genes in a plurality of response profiles, whether said set of genes is upregulated or downregulated by each of sad first plurality of perturbations, each response profile in said plurality of response profiles (i) comprising measurements of transcript levels for a plurality of genes, and (ii) resulting from a different perturbation among said first plurality of perturbations to said type of cell or organism, wherein each set of genes in said plurality of sets of genes consists of genes having transcripts that co-vary under a second plurality of perturbations or that are co-regulated, and wherein said consensus profile for said first plurality of perturbations consists of measurements of transcript levels for sad set or sets of genes that are determined in said determining step to be upregulated or downregulated by each of sad first plurality of perturbations, p1 wherein each of the sets of genes consists of genes which co-vary in the plurality of response profiles, wherein the genes which co-vary are identified by cluster analysis of genes in the plurality of response profiles, wherein said cluster analysis is carried out by a hierarchical clustering method, wherein a statistical significance for the sets of co-varying genes is determined by means of an objective statistical test, and wherein the objective statistical test comprises:

(a) determining for each cluster which is generated by said cluster analysis and defines a set of co-varying genes an actual fractional improvement in the cluster analysis of the genes based on the unpermuted responses of said genes, wherein said fractional improvement is an improvement in total scatter with respect to the center of said cluster as compared to total scatter with respect to the respective centers of the two clusters branching out of said cluster;

(b) generating permuted responses of genes by means of Monte Carlo randomization of perturbation index for the response of each gene across all perturbations;

(c) performing cluster analysis on the permuted responses of genes;

(d) determining for each cluster which is generated in step (c) and defines a set of co-varying genes the fractional improvement in the cluster analysis of genes based on the permuted responses of genes, wherein said fractional improvement is an improvement in total scatter with respect to the center of said cluster as compared to total scatter with respect to the respective centers of the two clusters branching out of said cluster; and (e) repeating steps (b) through (d) so that a distribution of fractional improvements in the cluster analysis of the genes is obtained for each cluster which is generated by said cluster analysis and defines a set of co-varying genes;

wherein the statistical significance of each of said sets of co-varying genes is determined by comparing the actual fractional improvement for the cluster defining said set to the distribution of fractional improvements for the cluster defining said set.

* * * * *